(12) United States Patent
Augeri et al.

(10) Patent No.: US 8,440,652 B2
(45) Date of Patent: May 14, 2013

(54) MST1 KINASE INHIBITORS AND METHODS OF THEIR USE

(75) Inventors: David John Augeri, Princeton, NJ (US); Jeffrey Thomas Bagdanoff, Martinez, CA (US); Simon David Peter Baugh, Ringoes, NJ (US); Marianne Carlsen, Yardley, PA (US); Kenneth Gordon Carson, Princeton, NJ (US); John Anthony Gilleran, Bridgewater, NJ (US); Wei He, Lawrenceville, NJ (US); Tamas Oravecz, The Woodlands, TX (US); Konstantin Salojin, Conroe, TX (US); Leonard Sung, Hopewell, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 13/410,407

(22) Filed: Mar. 2, 2012

(65) Prior Publication Data

US 2012/0225857 A1 Sep. 6, 2012

Related U.S. Application Data

(60) Provisional application No. 61/449,171, filed on Mar. 4, 2011.

(51) Int. Cl.
 *C07D 401/14* (2006.01)
 *C07D 495/04* (2006.01)
 *A61K 31/4418* (2006.01)
 *A61K 31/444* (2006.01)

(52) U.S. Cl.
 USPC ...... 514/211.05; 514/309; 514/352; 514/334; 514/255.05; 514/333; 514/221; 514/301; 514/212.07; 544/405; 546/141; 546/309; 546/257; 546/256; 546/114; 540/504; 540/490

(58) Field of Classification Search ............ 514/211.05, 514/309, 352, 334, 255.05, 333, 221, 301, 514/212.07; 544/405; 546/141, 309, 257, 546/256, 114; 540/504, 490
See application file for complete search history.

(56) References Cited

U.S. PATENT DOCUMENTS

| 8,153,804 B2 * | 4/2012 | Augeri et al. ............... 546/194 |
|---|---|---|
| 2008/0039450 A1 | 2/2008 | Jensen |
| 2009/0197862 A1 | 8/2009 | Steinig |
| 2011/0098325 A1 | 4/2011 | Raynham et al. |
| 2012/0040020 A1 | 2/2012 | Charrier |

FOREIGN PATENT DOCUMENTS

| WO | WO 2007016674 A2 * | 2/2007 |
|---|---|---|
| WO | WO2008025820 | 3/2008 |

OTHER PUBLICATIONS

Hilton et al., *Bioorganic & Med Chem.* 18 (2010) 4591.
Hilton et al., *Bioorganic & Med Chem.* 18 (2010) 707-718.
International Search Report issued in corresponding international application PCT/US2012/027376 and dated Jul. 24, 2012.

* cited by examiner

*Primary Examiner* — Kahsay T Habte
(74) *Attorney, Agent, or Firm* — Max Bachrach

(57) ABSTRACT

Compounds for the inhibition of mammalian Ste20-like kinase 1 (MST1) are disclosed, along with compositions comprising them and methods of their use in the treatment, management or prevention of an inflammatory or autoimmune diseases or disorders. Particular compounds are of the formula:

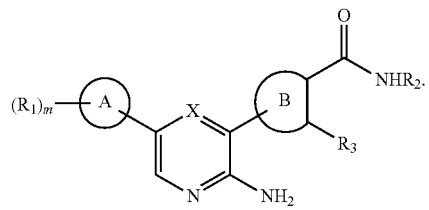

17 Claims, 11 Drawing Sheets

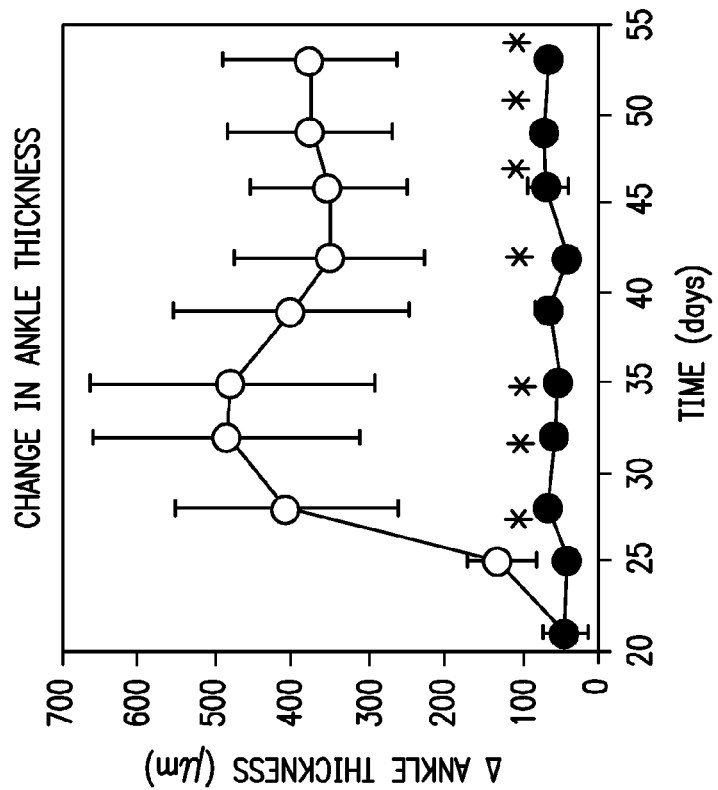
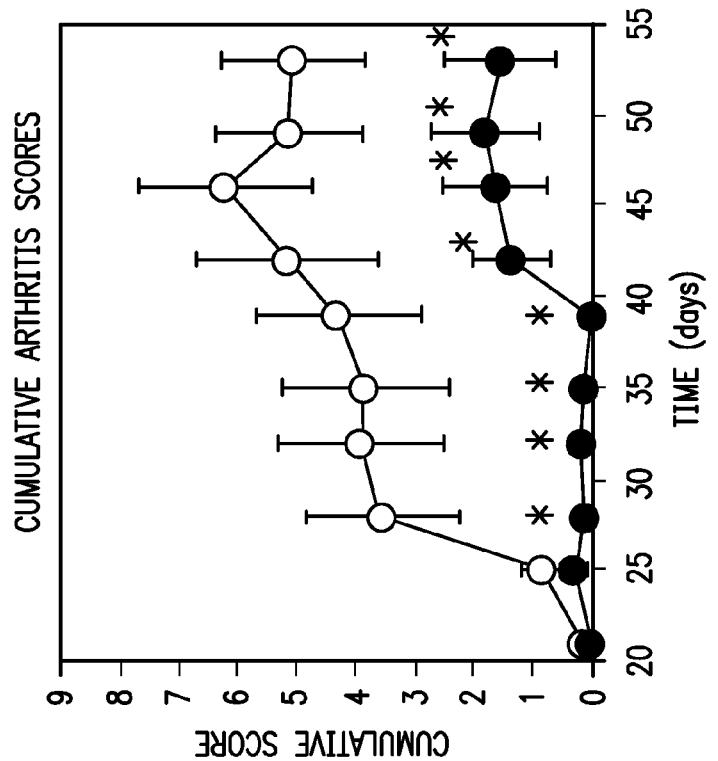
FIG. 1A
FIG. 1B

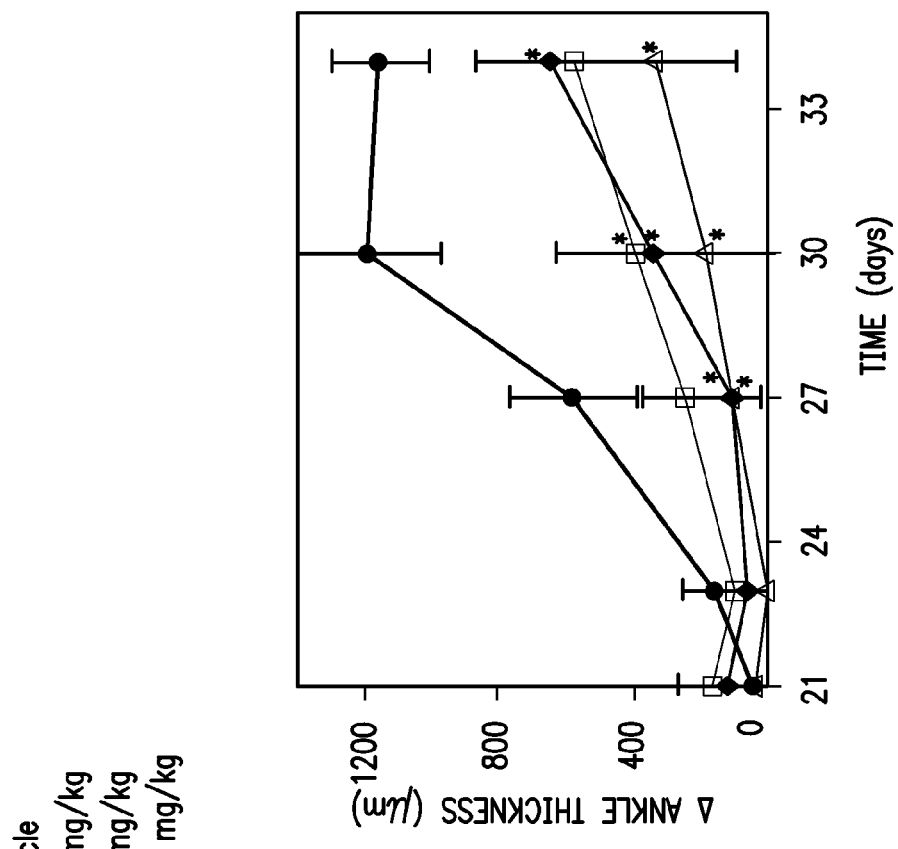
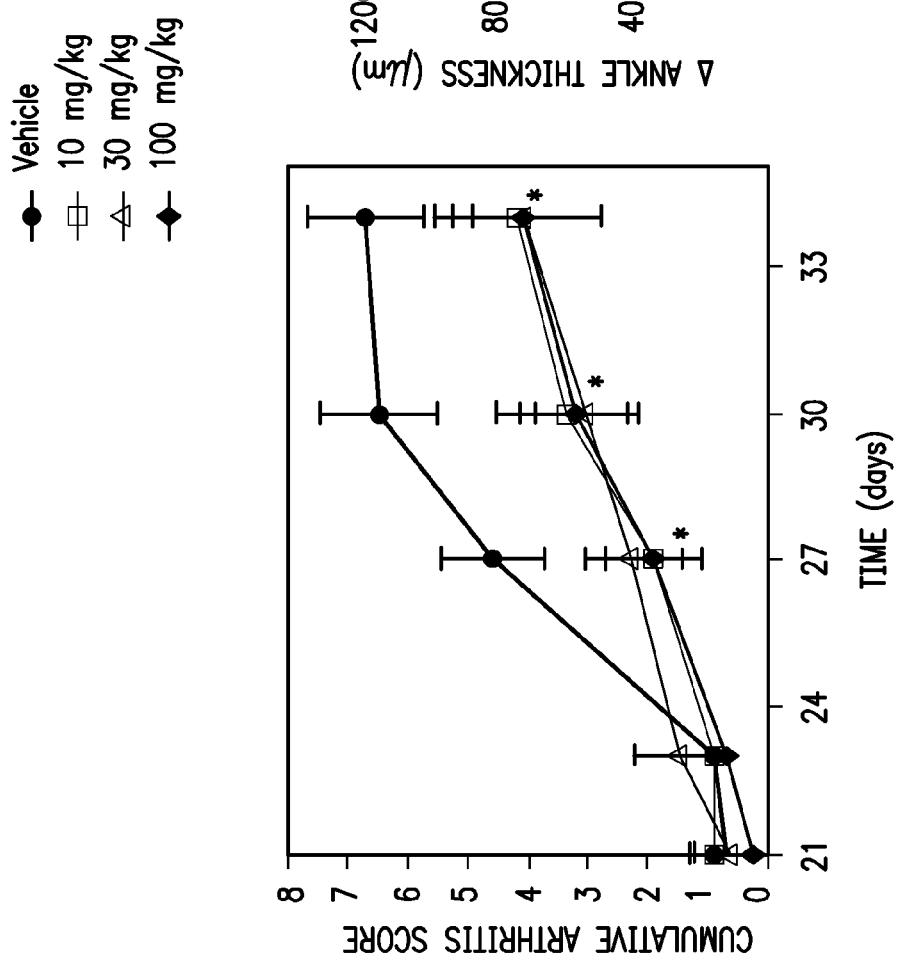
FIG. 4B
FIG. 4A

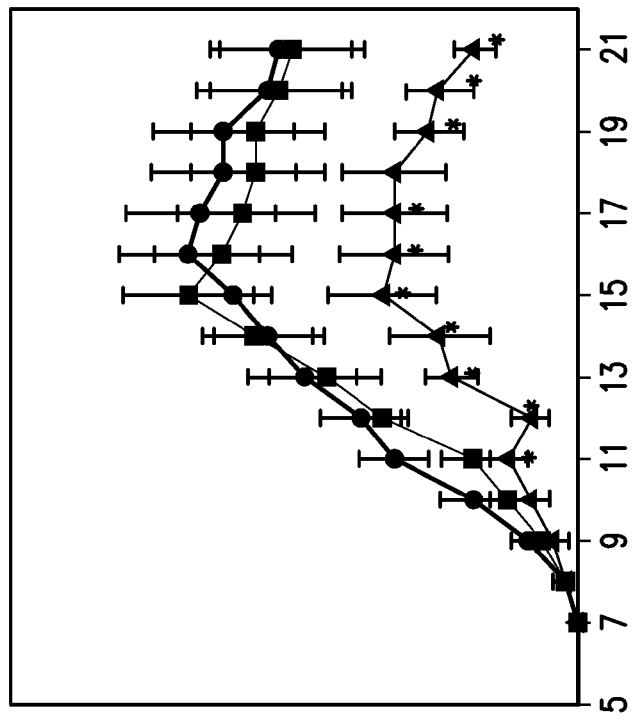
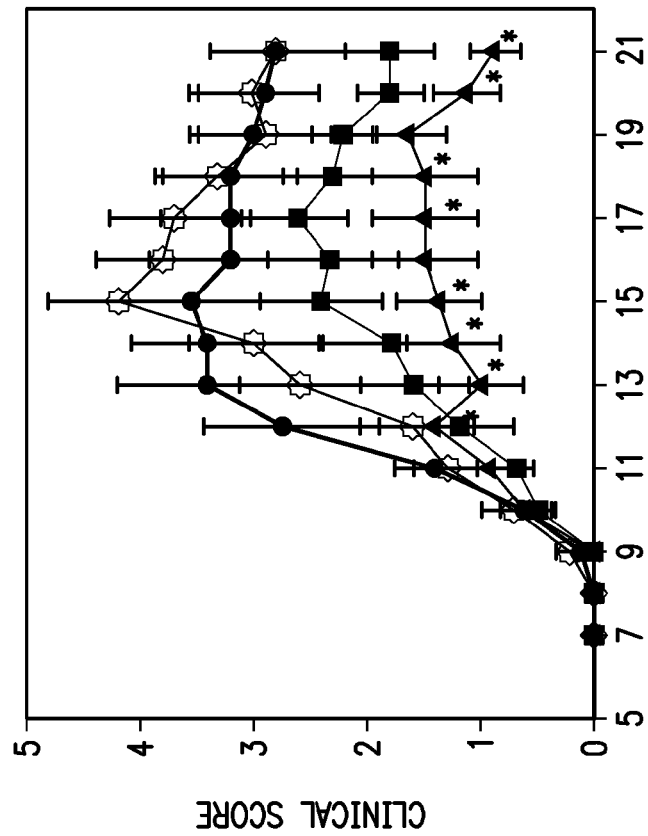
FIG. 9A
FIG. 9B

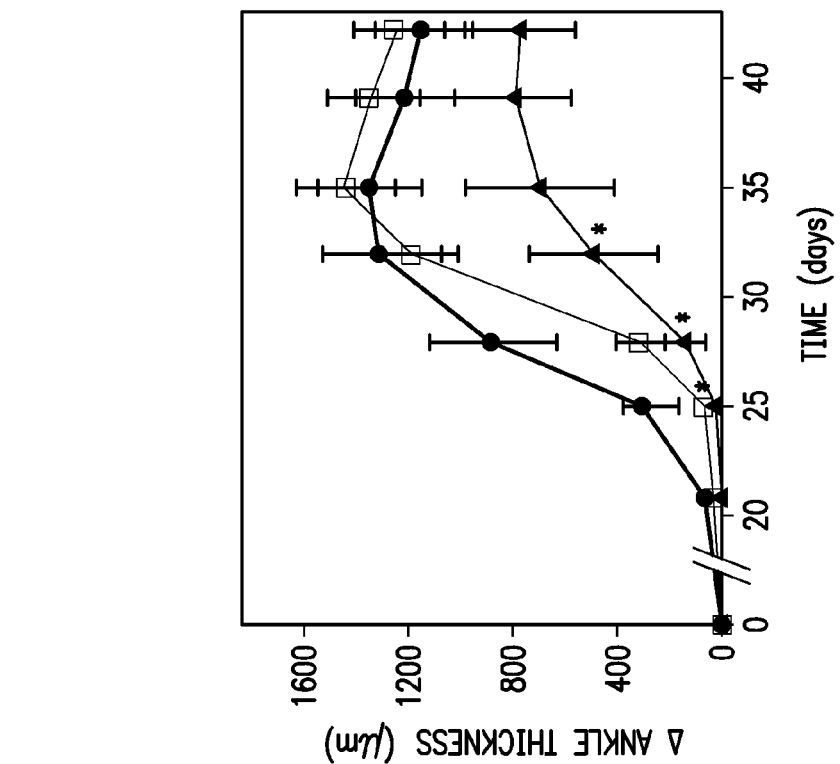
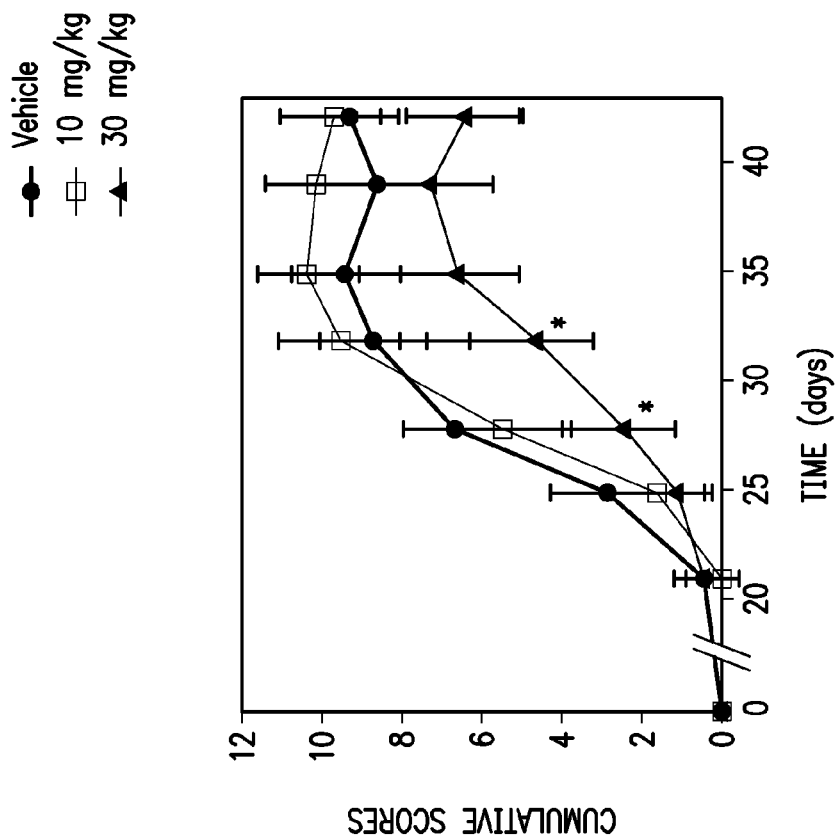
FIG. 10B
FIG. 10A

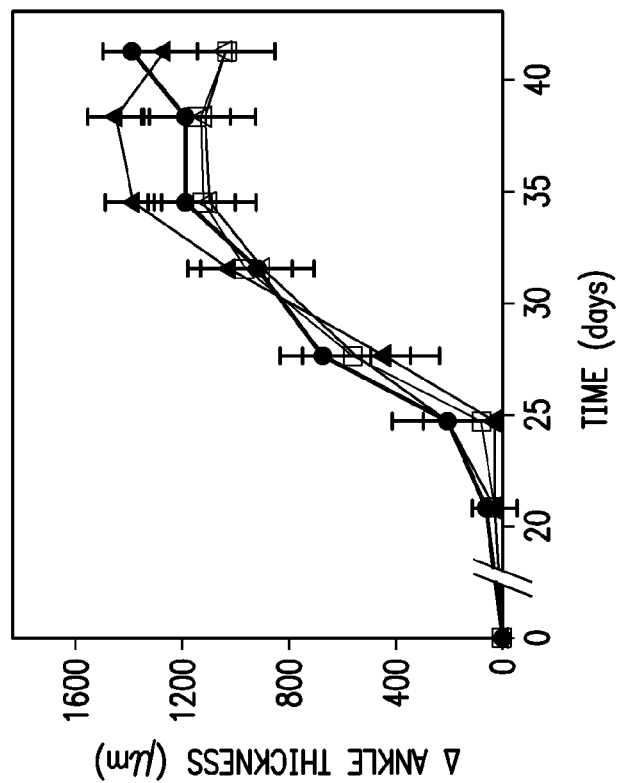
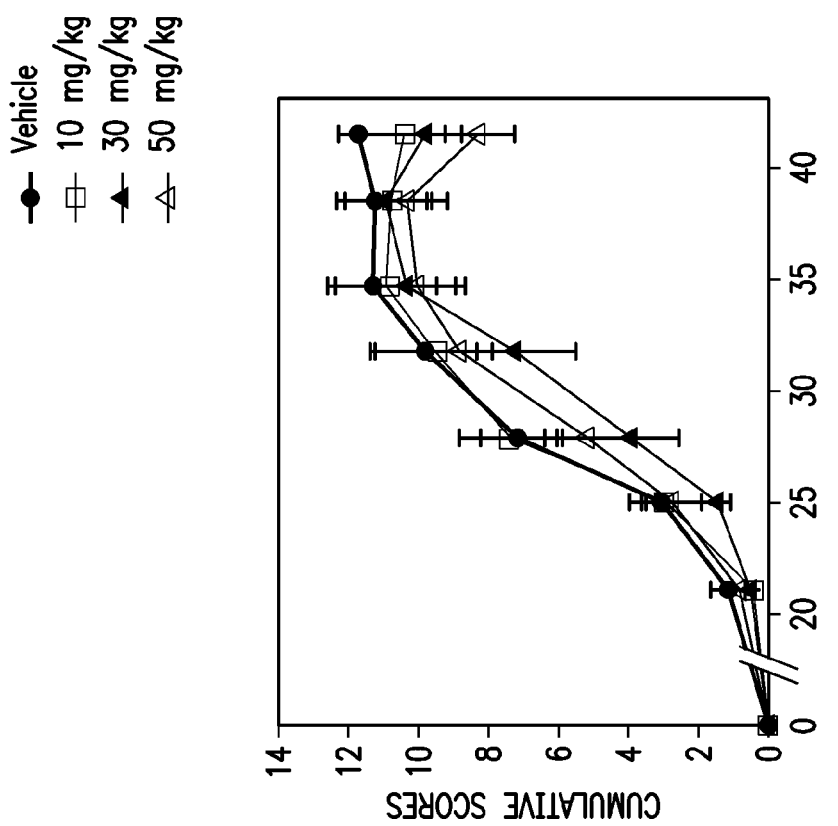
FIG. 10D
FIG. 10C

MST1 KINASE INHIBITORS AND METHODS OF THEIR USE

This application claims priority to U.S. provisional patent application No. 61/449,171, filed Mar. 4, 2011, the entirety of which is incorporated herein by reference.

1. FIELD OF THE INVENTION

This invention is directed to compounds useful as inhibitors of mammalian Ste20-like kinase 1 (MST1), compositions comprising them, and methods of their use.

2. BACKGROUND OF THE INVENTION

Mammalian Ste20-like kinase 1 (MST1) is a component of the "Hippo" signaling pathway, and "has been implicated in regulating the cell cycle, apoptosis and cellular responses to oxidative stress." Choi, J., et al., *Plos One* 4(11):e8011, 1 (2009). MST1-deficient mice reportedly display an accumulation of mature lymphocytes in the thymus and a decrease of lymphocytes in the blood and peripheral lymphoid tissues. Dong, Y., et al., *J. Immunology* 183(6):3865-3872, 3865 (2009). See also, Katagiri, K., et al., *Nat Immunol.* (9):919-28 (2006); Ling, P., et al., *Cell Signal.* 20(7):1237-47 (2008). MST1 is also known as serine/threonine kinase 4 (STK4) and kinase responsive to stress 2 (KRS2).

3. SUMMARY OF THE INVENTION

This invention is directed to compounds useful for the inhibition of MST1. One embodiment of the invention encompasses compounds of the formula:

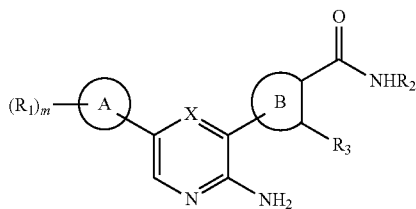

and pharmaceutically acceptable salts thereof, wherein: A is aryl or 4-7-membered heterocycle; B is aryl or 4-7-membered heterocycle; X is N or CH; $Y_1$ and $Y_2$ are each independently S, N or CH, provided that at least one of $Y_1$ and $Y_2$ is N or CH; each $R_1$ is independently $R_{1A}$, $-(R_{1B})_n SO_p R_{1C}$, $-(R_{1B})_n SO_p N(R_{1C})_2$, $-(R_{1B})_n NR_{1C} SO_p R_{1C}$, $-(R_{1B})_n C(O)N(R_{1C})_2$, or $-(R_{1B})_n NR_{1C} C(O) R_{1C}$, or optionally substituted $C_{1-12}$ hydrocarbyl or 2-12-membered heterocarbyl, which optional substitution is with one or more of $R_{1A}$; each $R_{1A}$ is independently amino, alkoxyl, carboxyl, cyano, halo, or hydroxyl; each $R_{1B}$ is independently $C_{1-12}$ hydrocarbyl optionally substituted with one or more of amino, alkoxyl, carboxyl, cyano, halo, or hydroxyl; each $R_{1C}$ is independently hydrogen or optionally substituted $C_{1-12}$ hydrocarbyl or 2-12-membered heterocarbyl, which optional substitution is with one or more of amino, alkoxyl, carboxyl, cyano, halo, or hydroxyl; $R_2$ and $R_3$ are taken together to form a 5-7-membered heterocycle optionally substituted with one or more of $R_{3,4}$, or: $R_2$ is hydrogen or $C_{1-4}$ alkyl; and $R_3$ is hydrogen or optionally substituted $C_{1-12}$ hydrocarbyl or 2-12-membered heterocarbyl, which optional substitution is with one or more of $R_{3,4}$; each $R_{3,4}$ is independently amino, alkoxyl, carboxyl, cyano, halo, or hydroxyl; k is 0 or 1; m is 0-3; n is 0 or 1; and p is 0, 1, or 2;

Another embodiment encompasses formulation comprising a compound of the invention and a pharmaceutically acceptable excipient. Another encompasses a method of using a compound of the invention for the inhibition of MST1.

Another embodiment encompasses a method of using a compound of the invention for the treatment, management or prevention of an inflammatory or autoimmune disease or disorder.

4. BRIEF DESCRIPTION OF THE FIGURES

Certain aspects of the invention may be understood from the attached figures, described below:

FIG. 1 shows the difference between MST1−/− mice (n=13) and their wild-type littermates (n−11) in a collagen-induced arthritis disease model (CIA).

FIG. 4 shows the effect of different doses of a compound of the invention when administered to mice in a CIA disease model. FIG. 4A shows the cumulative arthritis score over the course of the experiment; FIG. 4B shows the change in ankle thickness over the course of the experiment.

Figures 5A, 5B:
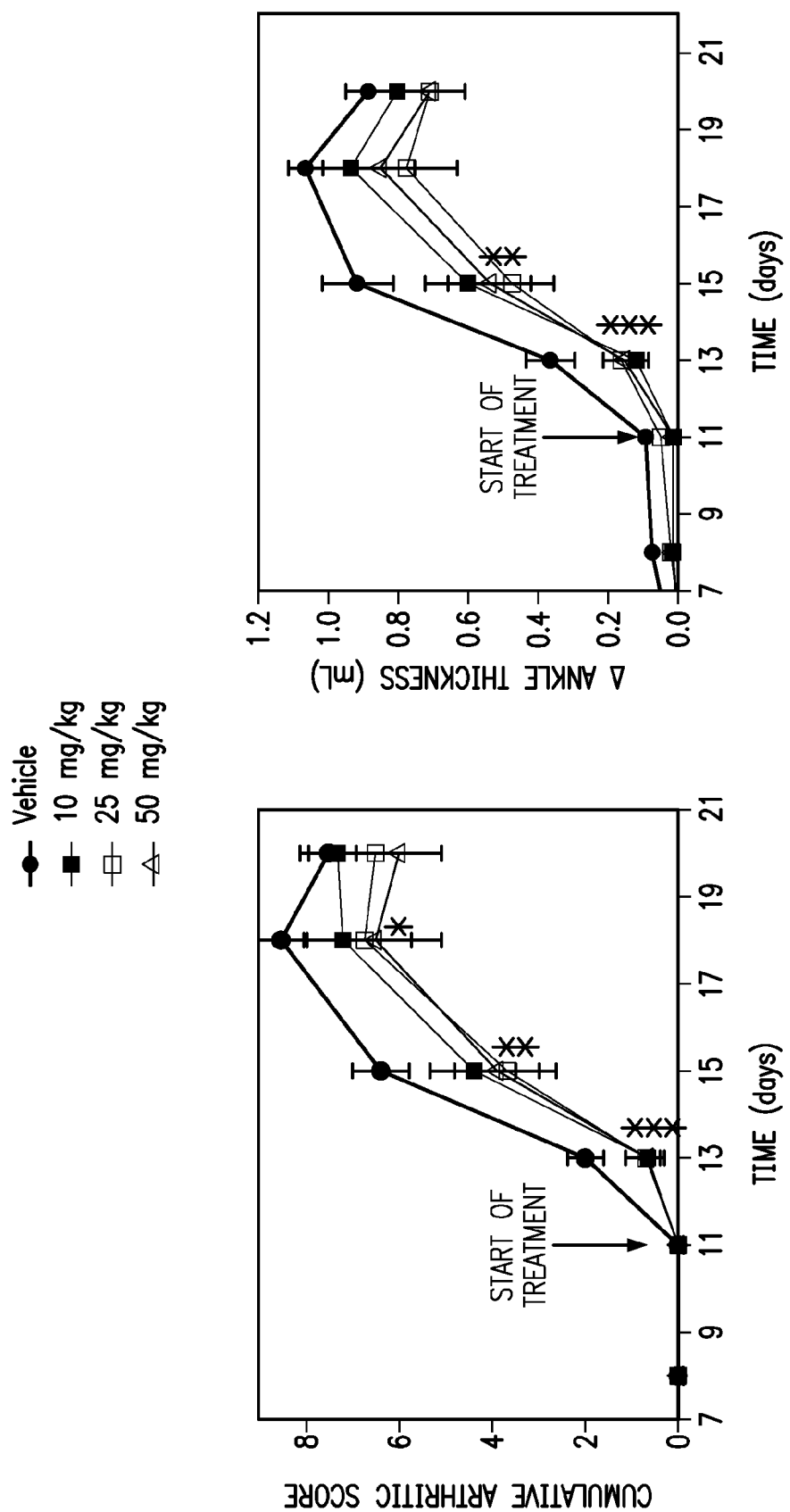

FIG. 5 shows the effect of different doses of a compound of the invention when administered to rats in a CIA disease model. FIG. 5A shows the cumulative arthritis score over the course of the experiment; FIG. 5B shows the change in ankle thickness over the course of the experiment.

Figure 6:
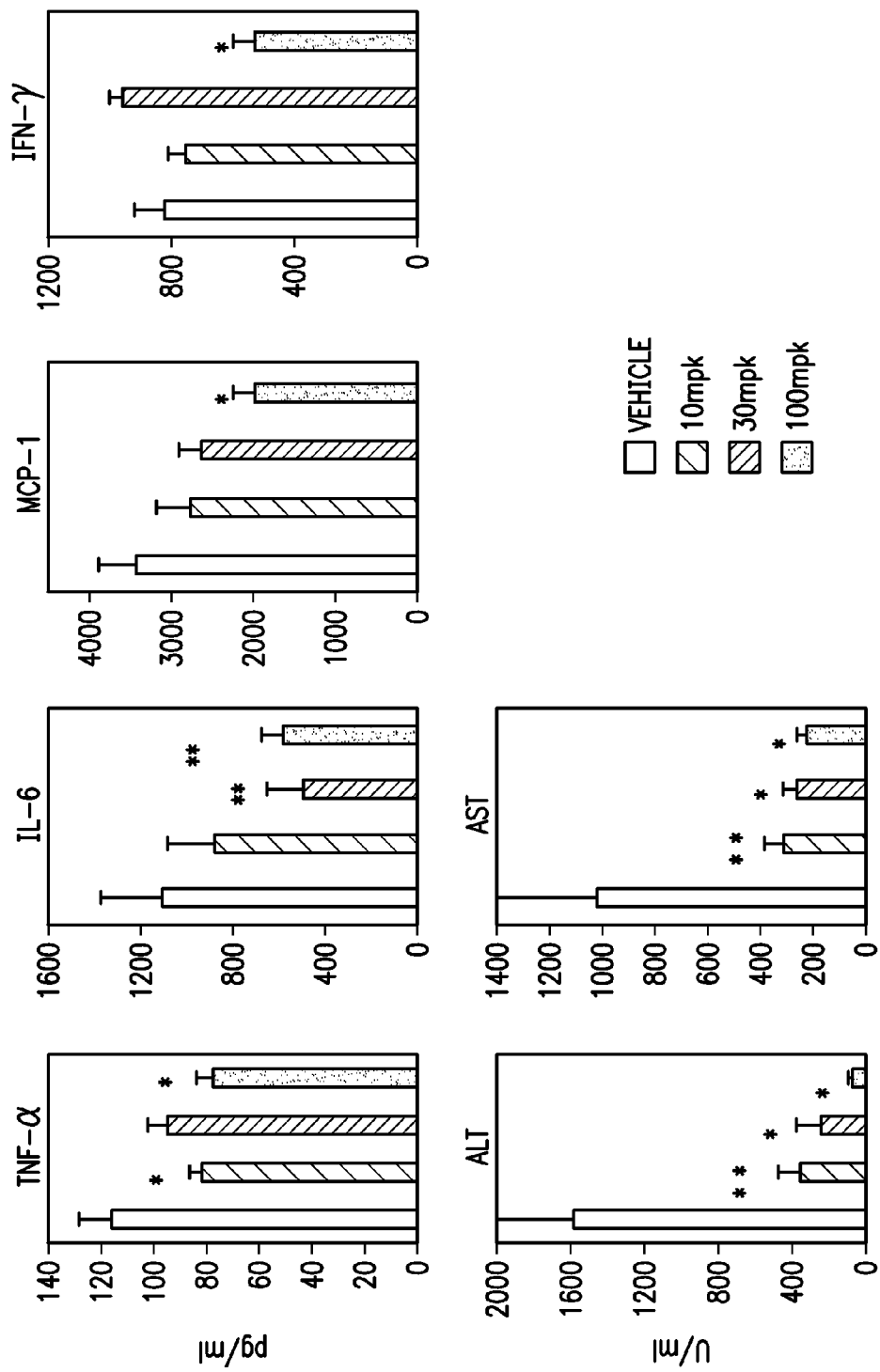

FIG. 6 shows the effect of short-term treatment with a compound of the invention on liver enzymes and cytokine response in mice subjected to a concanavalin A (ConA)-induced hepatitis disease model.

Figure 7:
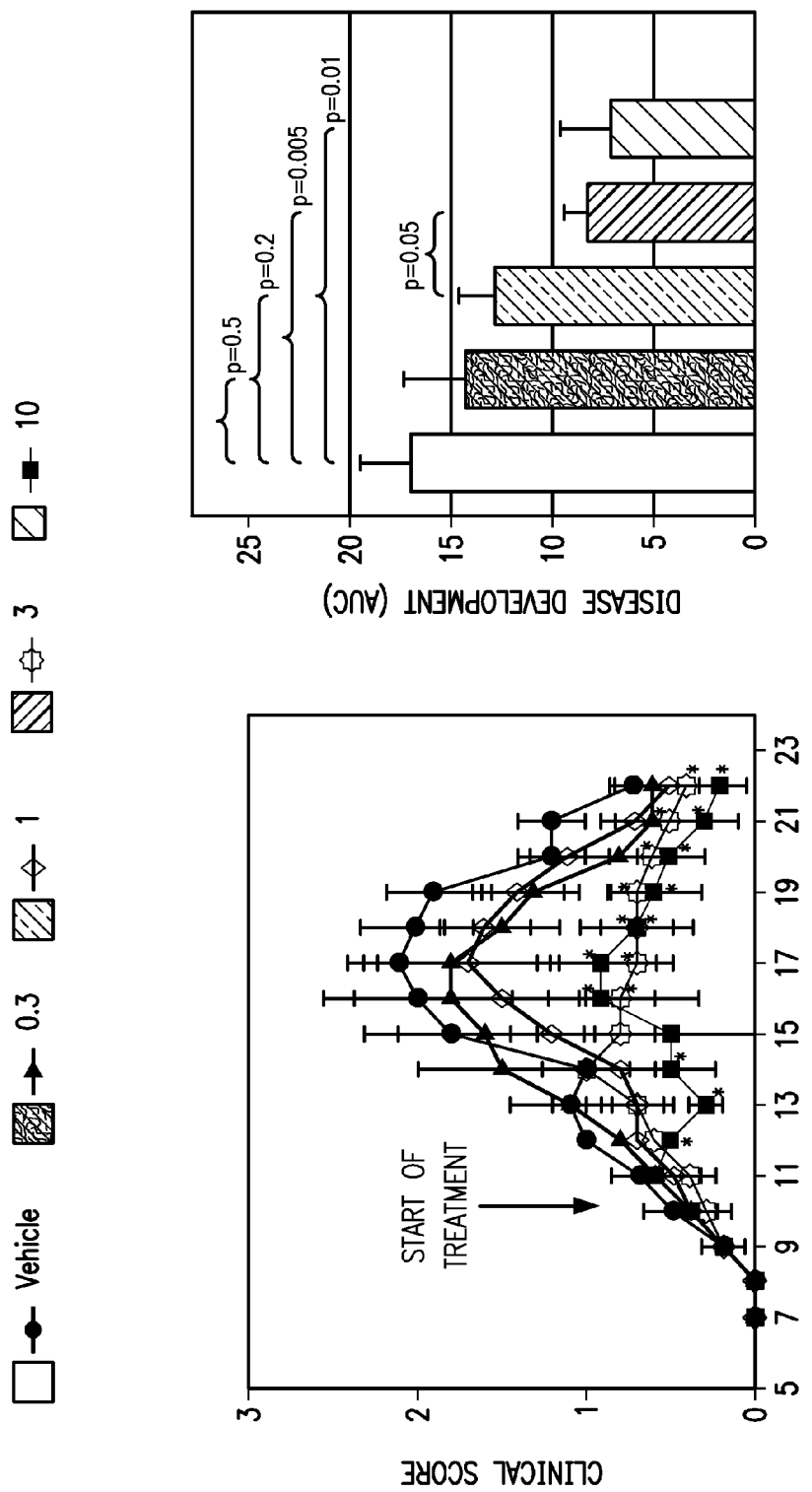

FIG. 7 shows the effect of different doses of a compound of the invention when administered therapeutically to rats in an EAE disease model. FIG. 7A shows the clinical score as a function of time; FIG. 7B shows the disease development as a function of compound dose (or vehicle).

Figure 8:
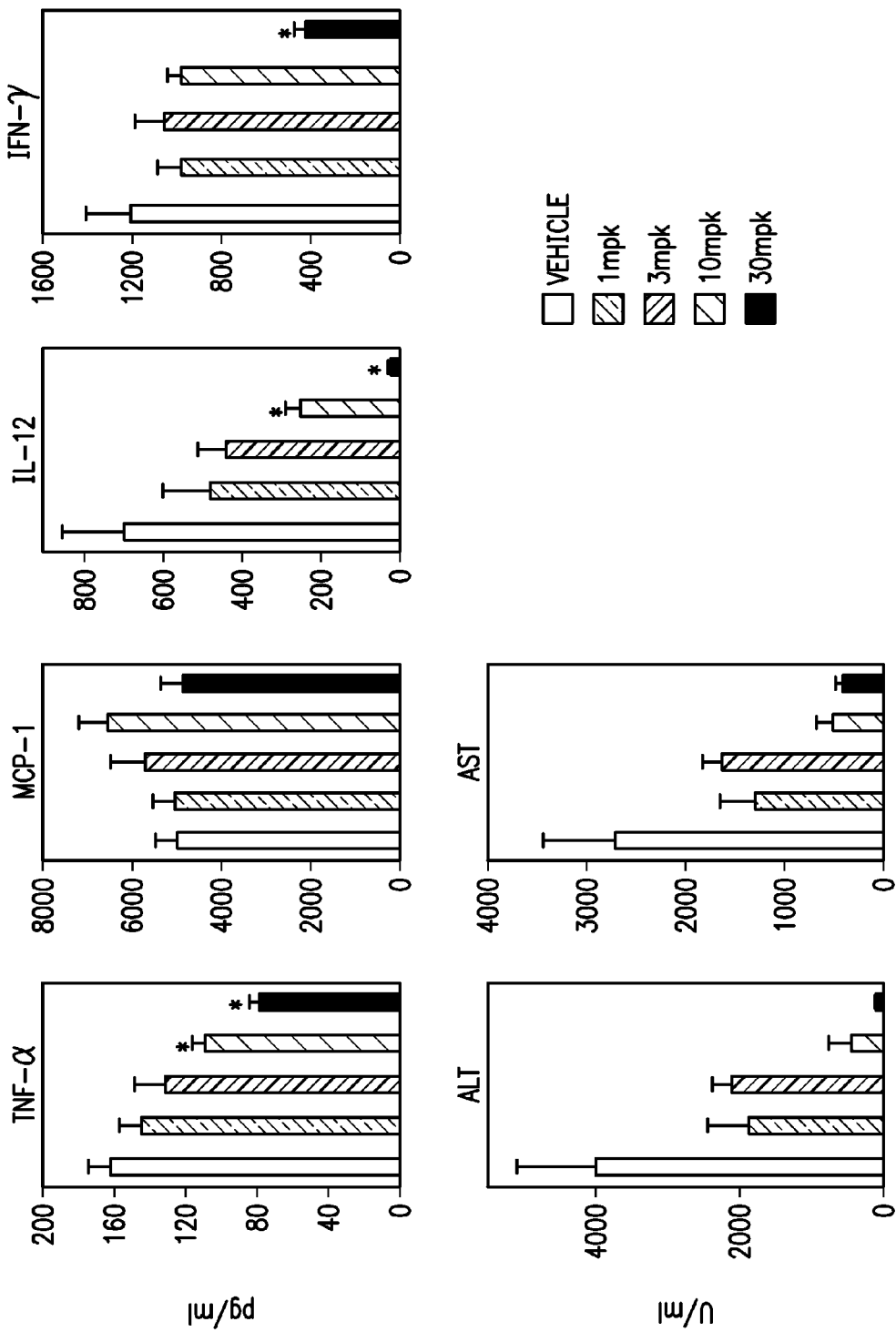

FIG. 8 shows the effect of short-term treatment with a compound of the invention on liver enzymes and cytokine response in mice subjected to a ConA-induced hepatitis disease model.

FIG. 9 shows the effect of different doses of a compound of the invention when administered therapeutically to mice in an EAE disease model. FIG. 9A shows the clinical score as a function of time for mice to whom the compound (and vehicle) were administered subcutaneously; FIG. 9B shows the clinical score as a function of time for mice to whom the compound (and vehicle) were administered orally.

FIG. 10 shows the effect of a compound of the invention in a mouse CIA model as a function of dose and method of delivery. FIGS. 10A and 10B show the effect of the compound on cumulative scores and change in ankle thickness when compound (and vehicle control) were administered subcutaneously. FIGS. 10C and 10D show the results obtained when the compound (and vehicle control) was administered orally.

5. DETAILED DESCRIPTION OF THE INVENTION

This invention is based, in part, on the discovery that MST1 knockout mice are significantly more resistant to animal autoimmune and inflammatory disease models than their wild-type littermates. This finding prompted the discovery of novel compounds that inhibit MST1, the most preferred of which are effective in animal disease models and exhibit desirable toxicological and pharmacokinetic properties.

5.1. Definitions

Unless otherwise indicated, the phrases "compounds of the invention," "compounds of the present disclosure," and the like refer to the compounds disclosed herein, particularly compounds of Formula I and salts thereof.

Unless otherwise indicated, the term "hydrocarbyl" means an aliphatic or alicyclic moiety having an all-carbon backbone and consisting of carbon and hydrogen atoms. Examples of hydrocarbyl groups include those having 1-20, 1-12, 1-6, and 1-4 carbon atoms (referred to as $C_{1-20}$ hydrocarbyl, $C_{1-12}$ hydrocarbyl, $C_{1-6}$ hydrocarbyl, and $C_{1-4}$ hydrocarbyl, respectively). Particular examples include alkyl, alkenyl, alkynyl, aryl, benzyl, cycloalkyl, cycloalkenyl, cycloalkylalkyl, cycloalkenylalkyl, napthyl, phenyl, and phenylethyl.

Examples of alkyl moieties include straight-chain and branched moieties having 1-20, 1-12, 1-6, 1-4 and 1-3 carbon atoms (referred to as $C_{1-20}$ alkyl, $C_{1-12}$ alkyl, $C_{1-6}$ alkyl, $C_{1-4}$ alkyl and $C_{1-3}$ alkyl, respectively). Particular examples include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Examples of alkenyl moieties include straight-chain and branched $C_{2-20}$, $C_{2-12}$ and $C_{2-6}$ alkenyl. Particular examples include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Examples of alkynyl moieties include straight-chain and branched $C_{2-20}$, $C_{2-12}$ and $C_{2-6}$ alkynyl. Particular examples include ethynyl and 2-propynyl (propargyl).

Examples of aryl moieties include anthracenyl, azulenyl, fluorenyl, indan, indenyl, naphthyl, phenyl and phenanthrenyl.

Examples of cycloalkyl moieties include $C_{3-12}$, $C_{3-7}$, $C_{4-6}$ and $C_6$ cycloalkyl. Particular examples include cyclopropyl, cyclobutyl, cyclopentyl, cyclohexyl and adamantyl.

Unless otherwise indicated, the term "halo" encompass fluoro, chloro, bromo, and iodo.

Unless otherwise indicated, the term "heterocarbyl" refers to a moiety having a backbone made up of one or more carbon atoms and one or more heteroatoms. Particular heteroatoms are nitrogen, oxygen and sulfur. A heterocarbyl moieties can be thought of as a hydrocarbyl moiety wherein at least one carbon atom, CH, $CH_2$, or $CH_3$ group is replaced with one or more heteroatoms and the requisite number of hydrogen atoms to satisfy valencies. Examples of heterocarbyl include 2-20, 2-12, 2-8, 2-6 and 2-4 membered heterocarbyl moieties, wherein the number range refers to the sum total of carbon, nitrogen, oxygen, and/or sulfur atoms in the moiety. The term "2-12 membered heterocarbyl" thus refers to a heterocarbyl moiety having a total of 2-12 carbon, nitrogen, oxygen, and/or sulfur atoms. Particular heterocarbyl moeities include straight chain and branched heteroalkyl, heteroalkenyl, and heteroalkynyl, as well as heterocycle and heteroaryl.

Examples of heteroalkyl moieties include 2-8-membered, 2-6-membered and 2-4-membered heteroalkyl moieties. Particular examples include alkoxyl, acyl (e.g., formyl, acetyl, benzoyl), alkylamino (e.g., di-($C_{1-3}$-alkyl)amino), arylamino, aryloxime, carbamates, carbamides, alkylcarbonyl, arylcarbonyl, aminocarbonyl, alkylaminocarbonyl, alkylsulfanyl, arylsulfanyl, alkylsulfinyl, arylsulfinyl, alkylsulfonyl, arylsulfonyl, alkylsulfonylamino, and arylsulfonylamino.

Unless otherwise indicated, the term "heterocycle" refers to a cyclic (monocyclic or polycyclic) heterocarbyl moiety which may be aromatic, partially aromatic or non-aromatic. Heterocycles include heteroaryls. Examples include 4-10-membered, 4-7-membered, 6-membered, and 5-membered heterocycles. Particular examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl. Because the term "heterocycle" refers to a ring, standing alone it does not encompass moieties such as oxazolidinone and imidazolidinone: such moieties are considered substituted heterocycles, viz. heterocycles substituted with oxo.

Examples of heteroaryl moieties include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "MST1 inhibitor" means a compound that inhibits MST1 in vitro with an $IC_{50}$ of less than 1 μm, 0.5 μm or 0.25 μm as determined by the assay described herein.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18th ed. (Mack Publishing, Easton Pa.: 1990) and *Remington: The Science and Practice of Pharmacy*, 19th ed. (Mack Publishing, Easton Pa.: 1995).

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, CONH-alkyl, CONH-aryl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-). In a particular embodiment, the term substituted refers to a derivative of that structure or moiety wherein one or more of its hydrogen atoms is substituted with alcohol, alkoxy, alkyl (e.g., methyl, ethyl, propyl, t-butyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aryl, carbamoyl (—NHC(O)O-alkyl- or —OC(O)NH-alkyl), carbamyl (e.g., CONH$_2$, as well as CONH-alkyl, CONH-aryl), halo, haloalkyl (e.g., —CCl$_3$, —CF$_3$, —C(CF$_3$)$_3$), heteroalkyl, imine (primary and secondary), isocyanate, isothiocyanate, thiol (e.g., sulfhydryl, thioether) or urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. This invention encompasses tautomers and solvates (e.g., hydrates) of the compounds disclosed herein.

5.2. Compounds of the Invention

This invention encompasses compounds of the formula:

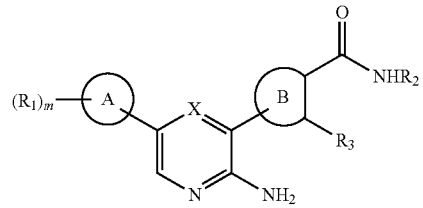

and pharmaceutically acceptable salts thereof, wherein: A is aryl or 4-7-membered heterocycle; B is aryl or 4-7-membered heterocycle; X is N or CH; Y$_1$ and Y$_2$ are each independently S, N or CH, provided that at least one of Y$_1$ and Y$_2$ is N or CH; each R$_1$ is independently R$_{1A}$, —(R$_{1B}$)$_n$SO$_p$R$_{1C}$, —(R$_{1B}$)$_n$SO$_p$N(R$_{1C}$)$_2$, —(R$_{1B}$)$_n$NR$_{1C}$SO$_p$R$_{1C}$, —(R$_{1B}$)$_n$C(O)N(R$_{1C}$)$_2$, or —(R$_{1B}$)$_n$NR$_{1C}$C(O)R$_{1C}$, or optionally substituted C$_{1-12}$ hydrocarbyl or 2-12-membered heterocarbyl, which optional substitution is with one or more of R$_{1A}$; each R$_{1A}$ is independently amino, alkoxyl, carboxyl, cyano, halo, or hydroxyl; each R$_{1B}$ is independently C$_{1-12}$ hydrocarbyl optionally substituted with one or more of amino, alkoxyl, carboxyl, cyano, halo, or hydroxyl; each R$_{1C}$ is independently hydrogen or optionally substituted C$_{1-12}$ hydrocarbyl or 2-12-membered heterocarbyl, which optional substitution is with one or more of amino, alkoxyl, carboxyl, cyano, halo, or hydroxyl; R$_2$ and R$_3$ are taken together to form a 5-7-membered heterocycle optionally substituted with one or more of R$_{3A}$, or: R$_2$ is hydrogen or C$_{1-4}$ alkyl; and R$_3$ is hydrogen or optionally substituted $C_{1-12}$ hydrocarbyl or 2-12-membered heterocarbyl, which optional substitution is with one or more of $R_{3A}$; each $R_{3A}$ is independently amino, alkoxyl, carboxyl, cyano, halo, or hydroxyl; k is 0 or 1; m is 0-3; n is 0 or 1; and p is 0, 1, or 2. Preferred compounds are MST1 inhibitors.

Particular compounds of the invention are of the formula:

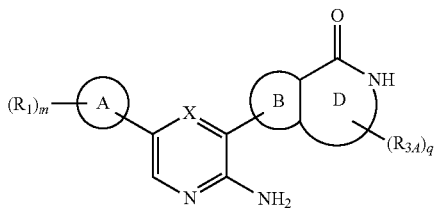

wherein D is a 4-7-membered heterocycle; and q is 0-2.

Particular compounds are of the formula:

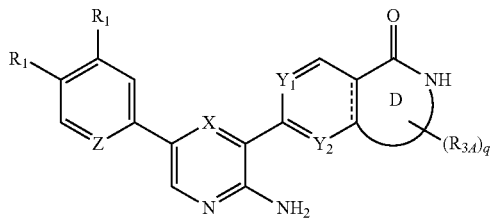

wherein $Y_1$ and $Y_2$ are each independently S, N, NH, CH or $CH_2$.

Particular compounds are of the formula:

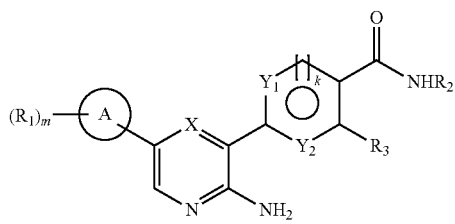

wherein $Y_1$ and $Y_2$ are each independently S, N or CH, provided that at least one of $Y_1$ and $Y_2$ is N or CH; and k is 0 or 1. Particular compounds are such that $R_3$ is not hydrogen when X is CH. More particular compounds are such that $R_3$ is not hydrogen when X is CH, $Y_1$ is CH and $Y_2$ is CH. More particular compounds are such that $R_3$ is not hydrogen when X is CH, $Y_1$ is CH, $Y_2$ is CH, and $R_2$ is hydrogen.

Particular compounds are of the formula:

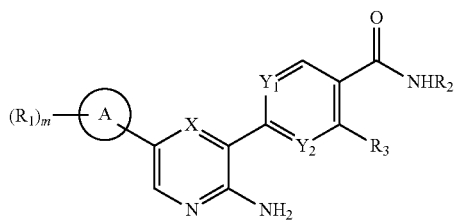

wherein $Y_1$ and $Y_2$ are each independently N or CH.

Other compounds of the invention of the formula:

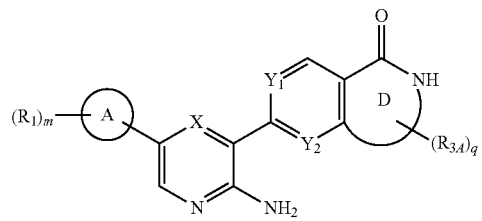

wherein $Y_1$ and $Y_2$ are each independently N or CH. Others are of the formula:

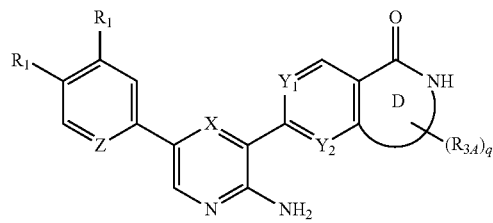

wherein $Y_1$ and $Y_2$ are each independently N or CH; and Z is N or $CR_1$.

Particular compounds of the invention are of the formulae:

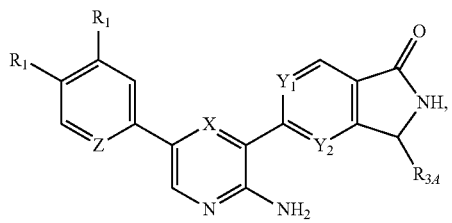

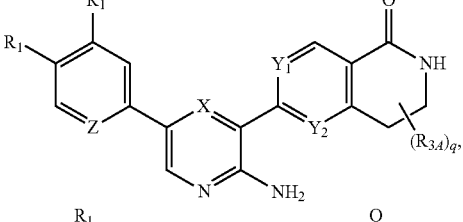

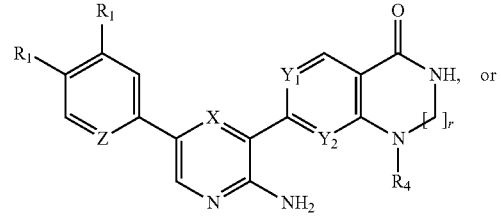

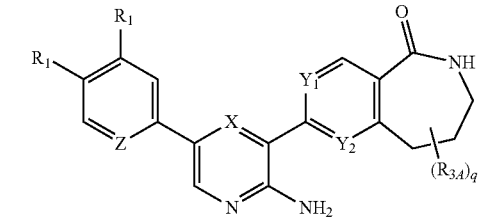

wherein $Y_1$ and $Y_2$ are each independently N or CH; r is 1 or 2, and $R_4$ is hydrogen or alkyl.

Other compounds of the invention are of the formula:

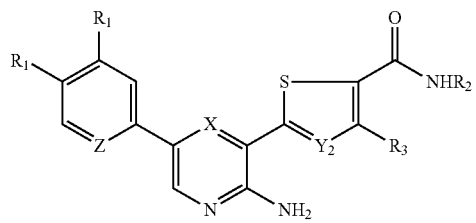

wherein $Y_2$ is N or CH. Others are of the formula:

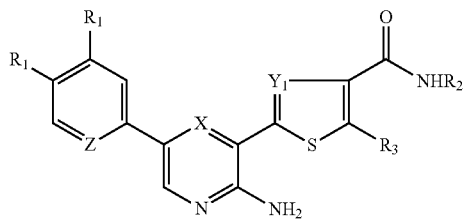

wherein $Y_1$ is N or CH.

Where applicable to the formulae disclosed herein, particular compounds of the invention are such that X is N.

Where applicable to the formulae disclosed herein, particular compounds of the invention are such that $Y_1$ is CH.

Where applicable to the formulae disclosed herein, particular compounds of the invention are such that $Y_2$ is CH.

Where applicable to the formulae disclosed herein, particular compounds of the invention are such that Z is N.

Where applicable to the formulae disclosed herein, particular compounds of the invention are such that Z is $CR_1$.

Where applicable to the formulae disclosed herein, particular compounds of the invention are such that $R_1$ is $-(R_{1B})_nSO_pR_{1C}$, $-(R_{1B})_nSO_pN(R_{1C})_2$, $-(R_{1B})_nNR_{1C}SO_pR_{1C}$, $-(R_{1B})_nC(O)N(R_{1C})_2$, or $-(R_{1B})_nNR_{1C}C(O)R_{1C}$.

Particular compounds of the invention are of the formula:

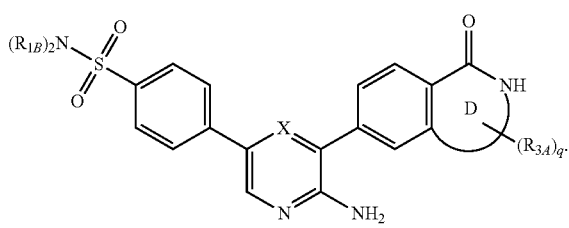

Other compounds are of the formula:

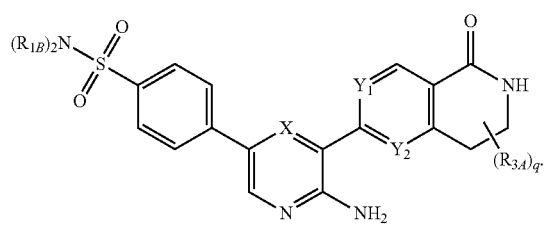

Compounds of the invention can be prepared by methods known in the art and by methods described herein. In general, compounds of the invention can be prepared as shown below:

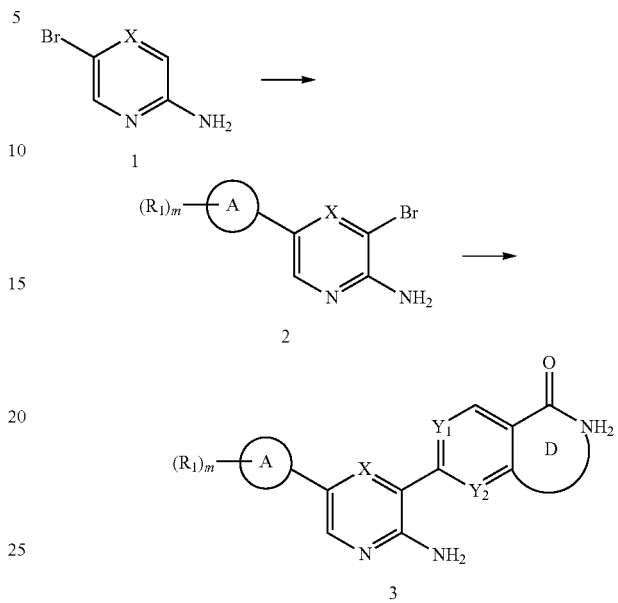

wherein the starting 2-amino heteroaryl bromide 1 is coupled with an appropriate aromatic boronic ester under standard Suzuki coupling conditions to provide, after treatment with an electrophilic brominating reagent, 2-amino hetero-biaryl bromide 2. Subsequent Suzuki coupling of 2 with another aromatic boronic ester displaying an amide functionality provides final product 3.

5.3. Methods of Use

This invention encompasses a method of inhibiting MST1, which comprises contacting MST1 (in vitro or in vivo) with an effective amount of a compound of the invention.

Another embodiment encompasses a method of suppressing immune response in a patient (e.g., a human), which comprises administering to the patient an effective amount of a compound of the invention.

Another embodiment encompasses a method of treating, managing or preventing an autoimmune or inflammatory disease or disorder, which comprises administering to a patient in need thereof a therapeutically or prophylactically effective amount of a compound of the invention. Examples of diseases and disorders include achlorhydra autoimmune, Addison's Disease, ankylosing spondylitis, anti-phospholipid syndrome, asthma (e.g., bronchial asthma), atopic dermatitis, autoimmune atrophic gastritis, Behcet's disease, Celiac Disease, Crohn's Disease, Cushing's Syndrome, dermatomyositis, Goodpasture's Syndrome, graft-vs-host disease, Grave's Disease, Hashimoto's thyroiditis, hepatitis (e.g., inflammatory and alcohol-induced), idiopathic adrenal atrophy, idiopathic thrombocytopenia, Kawasaki syndrome, Lambert-Eaton Syndrome, lupus erythematosus, multiple sclerosis, myasthenia gravis, pemphigoid, pemphigus vulgaris, pernicious anemia, pollinosis, polyarteritis nodosa, primary biliary cirrhosis, primary sclerosing cholangitis, psoriasis, psoriatic arthritis, Raynauds, Reiter's Syndrome, relapsing polychondritis, rheumatoid arthritis, Schmidt's Syndrome, scleroderma, Sjogren's Syndrome sympathetic ophthalmia, Takayasu's Arteritis, temporal arteritis, thyrotoxicosis, transplant rejection (e.g., of organ, cell or bone marrow), type 1 diabetes, ulcerative colitis, uveitis, and Wegener's granulomatosis.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In a particular embodiment, a compound of the invention is administered to a human patient in an amount of about 1-50, 1-25, or 2.5-15, or 5-10 mpk.

Compounds of the invention can be administered in combination with other immunosuppressant or anti-inflammatory drugs. The drugs can be administered at the same or at different times.

Examples of immunosuppressants include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Examples of anti-inflammatory drugs include glucocorticoids and NSAIDs.

Examples of glucocorticoids include aldosterone, beclometasone, betamethasone, cortisone, deoxycorticosterone, dexamethasone, fluorocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

5.4. Pharmaceutical Compositions

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, the oral administration of a compound susceptible to degradation in the stomach may be achieved using an enteric coating. Similarly, a formulation may contain ingredients that facilitate delivery of the active ingredient(s) to the site of action. For example, compounds may be administered in liposomal formulations in order to protect them from degradative enzymes, facilitate transport in circulatory system, and effect their delivery across cell membranes.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol®, and Encapsin™ (see, e.g., Davis and Brewster, *Nat. Rev. Drug Disc.* 3:1023-1034 (2004)), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:cornoil).

The composition, shape, and type of a dosage form will typically vary depending with use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. How to account for such differences will be apparent to those skilled in the art. See, e.g., *Remington's Pharmaceutical Sciences,* 18th ed., Mack Publishing, Easton Pa. (1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

6. EXAMPLES

6.1. Experimental Autoimmune Encephalomyelitis (EAE) Disease Model

Knockout mice and compounds were tested in an EAE disease model, which was generally carried out as described below.

Mouse Model.

Here, an adaptation of the method of Bettelli, et al., *J. Immunol.* 161:3299 (1998) was implemented. Eight to 12 weeks old C57Bl/6-Albino/129SvEv littermates were immunized subcutaneously with a total of 300 µg MOGp35-55 peptide (MEVGWYRSPFSRVVHLYRNGK) emulsified in complete Freund's adjuvant (CFA) containing 250 µg heat-inactivated *Mycobacterium tuberculosis* H37 Ra (Difco Laboratories). The antigen was divided equally across two injection sites in the abdominal flanks. Immediately following the injection of the emulsified antigen (day 0), each mouse received one intravenous injection of 500 ng of Pertussis toxin (List Biological Laboratories). Animal weights were recorded prior to the start of the experiment and monitored throughout the experiment, 2-3 times per week. Disease severity was scored on a scale as follows: 0=asymptomatic, no detectable sign of disease; 1=slight weakness of the tail/floppy tail and/or slumped hindquarters; 2=definite total paralysis of the tail; 3=mild waddle/distorted gait and total paralysis of the tail and/or mild impaired righting reflex; 4=heavy waddle with impaired control-weakness of hind limbs and/or impaired righting reflex; 5=paralysis of one of the hind limbs possibly with mild forelimb weakness; 6=paralysis of both hind limbs and/or moderate to severe forelimb weakness; 7=quadriplegia/paralysis of all limbs—hind and fore; 8=moribund/dead. When the severity of EAE was scored a "2" or greater, an additional water source consisting of Napa Nectar™, and pre-moistened food were placed on the cage floor. Animals with severe onset of the disease were given subcutaneous fluid therapy consisting of 1 cc of normal saline a minimum of once a day. Animals displaying scores of 7-8 without signs of recovery for more than 2 days were sacrificed.

Rat Model.

EAE was elicited in rats according to Mannie, M. D., et al., *Proc Natl. Acad. Sci. U.S.A.* 82:5515-5519 (1985). A synthetic peptide consisting of a sequence analogous to the reported minimal length encephalitogenic determinant of the bovine myelin basic protein (MBP) molecule (MBP68-82: YGSLPQKAQRPQDEN). Lewis rats (150-200 g, female; Charles River Laboratories, Wilmington, Mass.) were injected subcutaneously in both sides of the dorsal tail root with 0.1 ml of an emulsion consisting of 100 µg of encephalitogenic MBP peptide in complete Freund's adjuvant containing 200 µg of *Mycobacterium tuberculosis* H37Rv, Jamaican strain. Immunized animals were monitored daily for disease onset and progression, starting one week after immunization. Disease severity was scored as described above.

Animals displaying scores of 7-8 without signs of recovery for more than 2 days were sacrificed.

6.2. Collagen-Induced Arthritis (CIA) Disease Model

Knockout mice and compounds were tested in a CIA disease model, which was generally carried out as described below.

Mouse Model.

Eight to 16 weeks old DBA/1 mice were immunized intradermally (i.d.) at several sites into the base of the tail with 100 µg of chicken type II collagen (CII; Sigma Chemical Co.) in Freund's complete adjuvant (CFA; Difco, Detroit, Mich.) containing 2.5 mg/ml *M. tuberculosis*, followed by a repeat booster i.d. injection of CII (100 µg emulsified in CFA) given 3 weeks after the primary immunization. Mice were monitored daily for signs of arthritis, and disease severity scores were assessed by a visual scoring of 0 to 4 according to the following scale: 0=no erythema and swelling; 1=erythema and mild swelling of the mid-foot or ankle joint; 2=erythema and mild swelling extending from the ankle to the mid-foot; 3=erythema and moderate swelling extending from the ankle to the metatarsal joints; 4=erythema and severe swelling of the ankle, foot, and digits. Total disease severity scores were recorded as a sum of visual scores for four limbs. In addition to visual scoring, paw thickness was measured with a micrometer caliper.

Rat Model.

CIA was elicited in rats according to Rosloniec, E. F., et al., *Curr Protoc Immunol* Chapter 15: Unit 15, pp. 11-25. Here, Lewis rats (150-200 g, female; Charles River Laboratories, Wilmington, Mass.) were injected intradermally at the base of the tail with a total of 300 µl of a 1:1 emulsion of bovine type II collagen (CII; 150 µg total; Sigma-Aldrich) and incomplete Freund's adjuvant (IFA; 150 µl total; Sigma-Aldrich), followed by a repeat booster injection of the same emulsion 7 days after the primary immunization. Rats were monitored for signs of arthritis by clinical scoring (visual observation) of each rat paw, using the rating scale described above. The extent of swelling was calculated by subtracting the baseline values of the first measurement from the values of subsequent measurements.

6.3. Concanavalin A (ConA)-Induced Hepatitis Disease Model

This model was generally conducted as follows. C57Bl/6-Albino/129SvEv mice were injected intravenously (i/v) via the lateral tail vein with a single sublethal dose of Concanavalin A from *Canavalia ensiformis* (Jack bean, Type IV-S, lyophilized powder, aseptically processed; Sigma) administered at 10-16 mg/kg mouse body weight in a total volume of 0.1-0.3 ml of pyrogen-free PBS. The tail vein injections of mice restrained in a Plexiglas mouse restrainer were performed without anesthesia, using a 1 ml syringe with a 27 gauge needle. At six and 24 hr post-injection, blood samples were collected by retro-orbital bleeding. The animals were sacrificed and sera from the blood samples were analyzed for the presence of IL-12, TNF-α, MCP-1, IFN-γ, IL-10, and IL-6 using a mouse inflammation cytometric bead array (CBA) kit (BD Biosciences, Mountain View, Calif.), according to the manufacturer's instructions. Data were acquired with a FACSCalibur flow cytometer and analyzed with BD CBA Software (BD Biosciences). Biochemical markers of liver failure were assessed by measuring serum liver damage enzymes, aspartate aminotransferase (AST) and alanine aminotransferase (ALT), using a standard clinical biochemical analyzer. Livers of ConA-treated mice were sectioned and stained with H&E to evaluate the degree of T cell-mediated immune inflammation.

6.4. MST1 Knockout Mice

MST1 knockout mice (−/−) and their wild-type (C57Bl/6-Albino/129SvEv) littermates were bred and evaluated in EAE, CIA, and ConA-induced hepatitis disease models.

In the EAE model, eight to 12 week-old MST1−/− and wild-type (+/+) (C57Bl/6-Albino/129SvEv) littermates were tested. In the wild-type mice, EAE began as early as day 8 post-immunization, with a mean onset at day 11.4±0.78 and 12.3±0.9 (experiment #1 and experiment #2, respectively). The onset of disease was significantly delayed in the MST1-deficient animals (day 16.6±1.41 in experiment #1 and day 15.1±1.1 in experiment #2; p=0.005 and 0.06, respectively). In the acute post-immunization phase of EAE (days 7-22), there was a 4- to 6-fold decrease in the mean accumulative disease score in MST1−/− mice compared with their wild-type littermates. During this phase of the disease, the mean clinical score was significantly lower in the MST1−/− mice than in +/+ animals. In addition, the mean peak EAE score observed in the MST1+/+ animals on day 17 post-immunization was significantly higher than the mean peak EAE score in the MST1−/− group. Thus, homozygous deficiency of the MST1 gene significantly delayed the onset of EAE in mice and alleviated the severity of EAE in the acute post-immunization phase. Together, these results demonstrate that MST1−/− mice develop less severe EAE with significantly lower disease scores, and they are less susceptible to disease when compared with their wild-type littermates.

In the CIA model, eight to 16 week old MST1-deficient and wild-type (C57Bl/6-Albino/129SvEv) control mice were tested. As shown in FIG. 1, the MST1-deficient mice displayed a markedly decreased incidence of arthritis when compared with their wild-type littermates (* indicates p<0.03). Joint swelling and clinical signs of inflammation in the ankle and wrist joints were evident in wild-type controls from day 21 after the initial immunization, whereas the first signs of arthritis as measured by arthritis severity scores of 2 in the MST1-deficient mice developed only on day 42. The mean cumulative arthritis scores in the wild-type control group remained higher than 3.5 throughout the experiment. The severity of arthritis was significantly decreased in the MST1-deficient mice with a maximum mean cumulative arthritis score of 1.8 and a maximum mean Δ of ankle thickness of 70 μm reached by day 49, whereas arthritis in the control group began as earlier as at day 25 post-immunization, with a mean cumulative arthritis score of 3.5 at day 28, a maximum mean cumulative arthritis score of 6.2 at day 46 and a maximum mean Δ of ankle thickness of 485 μm reached by day 32. This significant decrease in the severity of arthritis in the MST1−/− mice persisted until day 53 after the first immunization.

In the Con-A hepatitis model, −/− and control wild-type (C57Bl/6-Albino/129SvEv) mice were tested. Analysis of Con A-induced cytokine production revealed that the serum levels of IL-12, TNF-α, and MCP-1 were significantly decreased in MST-1−/− mice compared to wild-type littermates. Similarly, release of liver damage enzymes (ALT and AST) in MST-1−/− mice was lower in MST-1-deficient than wild-type mice in two independent experiments.

6.5. General Synthetic Method A and Synthesis of 4-(6-amino-5-(1-oxo-1,2,3,4-tetrahydroisoquinolin-6-yl)pyridin-3-yl)-N-cyclopropylbenzenesulfonamide The captioned compound was prepared by general method A, represented below:

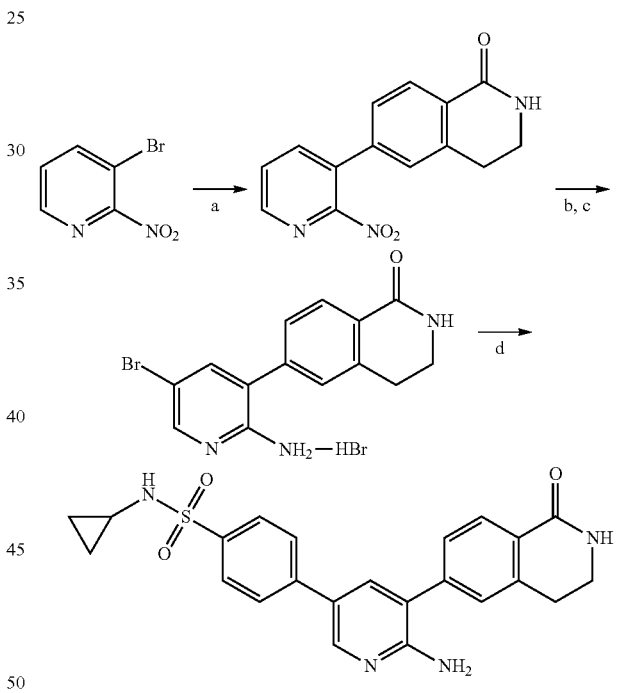

wherein:
a is 1-oxo-1,2,3,4-tetrahydroisoquinolin-6-ylboronic acid, PdCl$_2$dppf-DCM, Cs$_2$CO$_3$, DMF, 100° C.; b is H$_2$, Pd—C, MeOH:DMF (1:2); c is Br$_2$, MeOH; and d is 4-(N-cyclopropylsulfamoyl)phenylboronic acid, Pd(PPh$_3$)$_4$, aq. Na$_2$CO$_3$, n-BuOH, 100° C.

In particular, a room temperature slurry of 3-bromo-2-nitropyridine (6.4 g, 31.57 mmol), 1-oxo-1,2,3,4-tetrahydroisoquinolin-6-ylboronic acid (6.63 g, 34.73 mmol), PdCl$_2$dppf-DCM (1.031 g, 1.26 mmol) and Cs$_2$CO$_3$ (15.43 g, 47.35 mmol) in DMF was sonicated for 20 min while iteratively evacuating the reaction mixture and back-filling with dry N$_2$ to effect degassing. The degassed slurry was then heated to 100° C. and the reaction was monitored by LC/MS. At completion, the reaction was filtered then concentrated under vacuum. The resulting crude material was redissolved in MeOH, treated with silica gel (15 g) then concentrated under vacuum to dryness, then azeotroped with toluene to remove trace methanol. The powder was slurried in DCM, then flashed over a tall plug of silica, eluting with 4-10% MeOH:DCM. Pure fractions were combined and concentrated. The resulting brown solid was slurried in DCM (15 mL), then filtered to remove colored impurities to provide 6-(2-nitropyridin-3-yl)-3,4-dihydroisoquinolin-1(2H)-one as a tan solid (7.4 g, 87% yield). $^1$H NMR (400 MHz, DMSO-$d_6$) δ ppm 8.63 (d, J=4.5 Hz, 1H), 8.23 (d, J=7.8 Hz, 1H), 8.04 (br. s., 1H), 7.86-7.98 (m, 2H), 7.38 (s, 1H), 7.35 (d, J=9.0 Hz, 1H), 3.37-3.44 (m, 2H), 2.95 (t, J=6.3 Hz, 2H); $^{13}$C NMR (101 MHz, DMSO-$d_6$) δ ppm 163.78, 156.77, 148.11, 142.04, 139.99, 137.26, 129.76, 128.46, 128.33, 127.63, 127.02, 126.19, 27.52; MS (EI) m/z: 270 [M+H]$^+$; HRMS calcd for $C_{14}H_{12}N_3O_3$ [M+H]$^+$ 270.0879, found 270.0870.

A solution of 6-(2-nitropyridin-3-yl)-3,4-dihydroisoquinolin-1(2H)-one (7.4 g, 27.50 mmol) in methanol (100 mL) and DMF (200 mL) was degassed by iteratively evacuating the reaction flask and backfilling with dry nitrogen (5×). To the degassed solution was added 10% Pd on carbon (Degussa type, 50 wt % water, 1.5 g). The reaction was charged with hydrogen (~1 atm) by iteratively evacuating the reaction vessel and back-filling with hydrogen (3×). The reaction was maintained at room temperature with vigorous stirring and monitored by LC/MS. At completion, the reaction was degassed and purged with nitrogen as before, then heated to 70° C. and filtered while hot over a pad of celite. The pad was rinsed with DMF (100 mL) that was heated to 120° C. The combined organics were concentrated under vacuum, and azeotroped with toluene (2×150 mL) to remove residual DMF.

The obtained solid was treated with methanol (200 mL) then heated and sonicated to provide milky slurry. The slurry was cooled to 0° C. and treated with bromine (1.48 mL, 28.88 mmol) by careful addition. The reaction was monitored by LC/MS, and, after completion (15 min) was concentrated under vacuum. The resulting material was stored under high vacuum overnight to remove trace bromine to provide 6-(2-amino-5-bromopyridin-3-yl)-3,4-dihydroisoquinolin-1(2H)-one hydrobromide as a brown solid (11.16 g, 100% yield), which was used without further purification. $^1$H NMR (400 MHz, DMSO-$d_6$) δ ppm 8.31 (d, J=2.3 Hz, 1H), 8.03 (br. s., 1H), 8.00 (d, J=2.0 Hz, 1H), 7.95 (d, J=8.3 Hz, 1H), 7.45 (s, 1H), 7.44 (s, 2H), 3.38-3.45 (m, 2H), 2.96 (t, J=6.6 Hz, 2H); $^{13}$C NMR (101 MHz, DMSO-$d_6$) δ ppm 163.89, 151.88, 144.15, 140.08, 137.31, 136.47, 130.22, 128.00, 127.79, 127.10, 126.28, 104.76, 48.52, 27.70; MS (EI) m/z: 318, 320 [M+H]$^+$; HRMS calcd for $C_{14}H_{12}BrN_3O$ [M+H]$^+$ 318.0242, found 318.0234.

A slurry of the aryl bromide 6-(2-amino-5-bromopyridin-3-yl)-3,4-dihydroisoquinolin-1(2H)-one hydrobromide (6.50 g, 16.25 mmol), 4-(N-cyclopropylsulfamoyl)phenylboronic acid (6.57 g, 17.88 mmol), Pd(PPh$_3$)$_4$ (565 mg, 0.49 mmol) and 2.0 M aq Na$_2$CO$_3$ (4.3 g, 48.75 mmol) in n-BuOH (180 mL) was degassed by bubbling a stream of anhydrous nitrogen for 10 min. The reaction mixture was then heated to 100° C. for 3 h. At completion, the hot reaction was diluted with DMF (300 mL) and heated to 125° C. before filtering the hot slurry over a pad of celite dampened with hot DMF. The organics were cooled to room temperature, then treated with silica gel (40 g) and the solvent was removed under vacuum. The dry powder was slurried in DCM and loaded on top of a tall plug of silica gel slurried in DCM and the system was eluted with 10-20% MeOH. The product containing fractions were concentrated, and the resulting solid was slurried in hot DMF, then filtered. The cake was rinsed with MeOH, then dried under vacuum to provide 4-(6-amino-5-(1-oxo-1,2,3,4-tetrahydroisoquinolin-6-yl)pyridin-3-yl)-N-cyclopropylbenzenesulfonamide as a white powder (5.3 g, 75% yield). $^1$H NMR (400 MHz, DMSO-$d_6$) δ ppm 8.62 (d, J=2.0 Hz, 1H), 8.34 (d, J=2.0 Hz, 1H), 8.13 (br. s., 2H), 8.07 (br. s., 1H), 8.04 (d, J=8.6 Hz, 2H), 7.99 (d, J=8.3 Hz, 1H), 7.88 (d, J=8.3 Hz, 2H), 7.57 (s, 1H), 7.56 (s, 2H), 3.43 (t, J=5.7 Hz, 2H), 2.99 (t, J=6.3 Hz, 2H), 2.12 (tt, J=6.8, 3.5 Hz, 1H), 0.44-0.53 (m, 2H), 0.36-0.44 (m, 2H); MS (EI) m/z: 435 [M+H]$^+$.

6.6. General Synthetic Method B and Synthesis of 5-(6-amino-5-(1-oxo-1,2,3,4-tetrahydroisoquinolin-6-yl)pyridin-3-yl)-N-ethylthiophene-2-sulfonamide The captioned compound was prepared by general method B, represented below:

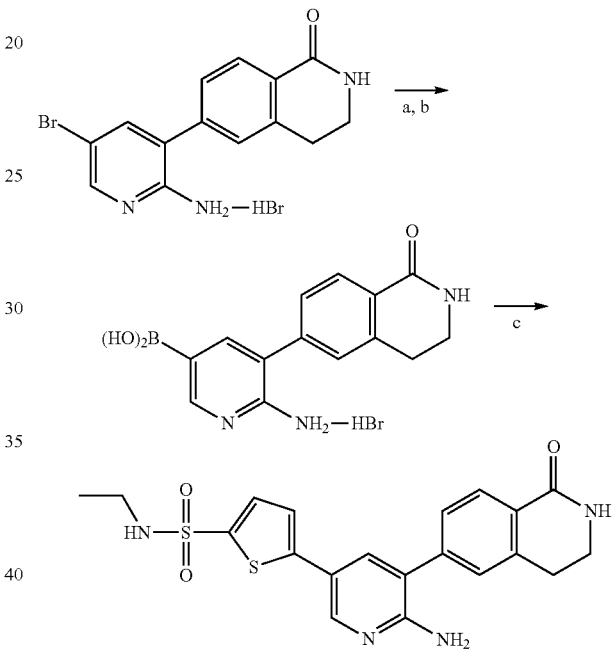

wherein:
a is 1 N NaHCO$_3$:DCM (1:1); b is MeLi, t-BuLi, B(Oi-Pr)$_3$, THF, −78° C. to room temperature; and c is 5-bromo-N-ethylthiophene-2-sulfonamide, PdCl$_2$(PPh$_3$)$_2$, MeCN, 2.0 M aq. Na$_2$CO$_3$, μ-wave at 140° C. for 6 min.

A solution of 6-(2-amino-5-bromopyridin-3-yl)-3,4-dihydroisoquinolin-1(2H)-one hydrobromide (2.00 g, 5.0 mmol), obtained as described in Example 5.2, was cooled to 0° C. in DCM (50 mL) and was slowly treated with a 1 N aq. NaHCO$_3$ solution (25 mL). The cooled solution was stirred vigorously for 5 min, and then the layers were separated. The organic layer was dried over MgSO$_4$, filtered and concentrated then dried thoroughly under vacuum. The resulting tan solid (1.54 g, 5.0 mmol) was dissolved in THF (500 mL), cooled to −78° C. and treated with a 1.6M MeLi solution in Et$_{20}$ (10.3 mL, 16.5 mL). The reaction was maintained for 15 min, before the dropwise addition of 1.7M t-BuLi (8.8 mL, 14.96 mmol) over 10 min. The cooled solution was stirred vigorously for an additional 45 min before the addition of triisopropylborate (5.2 mL, 22.5 mmol). The reaction was allowed to warm to room temperature for 30 min before quenching with sat. aq. NH$_4$Cl (1 mL) followed by water (5 mL). The resulting precipitate was filtered off and washed with cold water, then dried overnight under vacuum to provide (6-amino-5-(1-oxo-1,2,3,4-tetrahydroisoquinolin-6-yl)pyridin-3-yl)boronic acid (1.10 g, 78% yield). $^1$H NMR (400 MHz, DMSO-$d_6$) δ ppm 8.35 (d, J=2.3 Hz, 1H), 7.97 (br. s., 1H), 7.92 (d, J=7.8 Hz, 1H), 7.76 (t, J=5.6 Hz, 1H), 7.67 (d, J=2.5 Hz, 1H), 7.50 (d, J=3.8 Hz, 1H), 7.43-7.47 (m, 2H), 6.21 (s, 2H), 2.96 (t, J=6.4 Hz, 2 H), 2.85-2.92 (m, 2H); MS (EI) m/z: 284 [M+H]$^+$.

A mixture of (6-amino-5-(1-oxo-1,2,3,4-tetrahydroisoquinolin-6-yl)pyridin-3-yl)boronic acid (291 mg, 1.02 mmol), 5-bromo-N-ethylthiophene-2-sulfonamide (278 mg, 1.02 mmol), and PdCl$_2$(PPh$_3$)$_2$ (35 mg, 0.05 mmol) in n-BuOH (3 mL) was treated with 2.0 M aq. Na$_2$CO$_3$ solution (1 mL) then microwave heated at 140° C. for 6 min. The reaction was then filtered, and purified by HPLC to provide 5-(6-amino-5-(1-oxo-1,2,3,4-tetrahydroisoquinolin-6-yl)pyridin-3-yl)-N-ethylthiophene-2-sulfonamide as a white solid after preparatory HPLC purification. $^1$H NMR (300 MHz, MeOH) δ ppm 8.31 (d, J=2.3 Hz, 1H), 8.07 (d, J=8.0 Hz, 1 H), 7.72 (d, J=2.3 Hz, 1H), 7.54 (dd, J=3.8, 2.1 Hz, 1H), 7.52 (d, J=1.7 Hz, 1H), 7.48 (s, 1 H), 7.34 (d, J=3.8 Hz, 1H), 3.57 (dd, J=13.4, 6.5 Hz, 1H), 2.93-3.15 (m, 2H), 1.85-2.03 (m, 3H), 1.13 (dd, J=14.5, 7.2 Hz, 3H); MS (EI) m/z: 429 [M+H]$^+$.

6.7. General Synthetic Method C and Synthesis of 6-(2-amino-5-(4-(ethylsulfonyl)phenyl)pyridin-3-yl)-3,4-dihydroisoquinolin-1(2H)-one The captioned compound was prepared by General Method C, represented below:

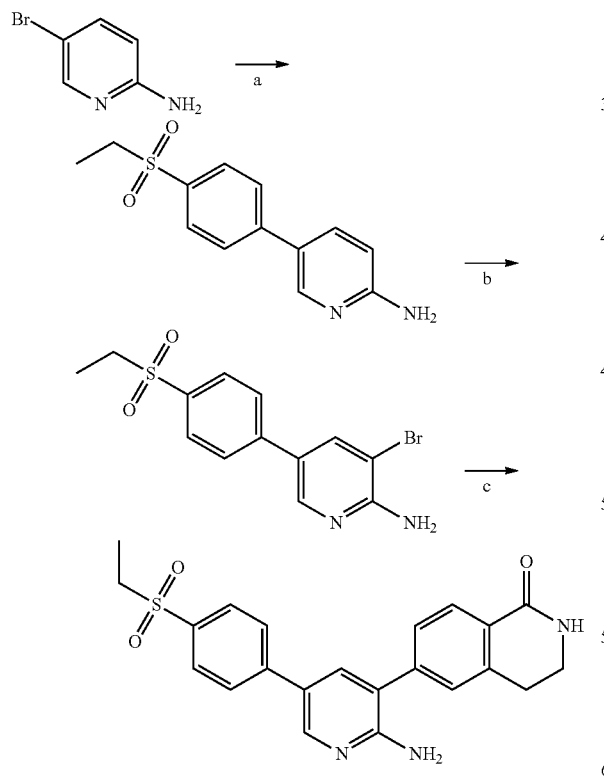

wherein; a is 4-(ethylsulfonyl)phenylboronic acid, Pd(PPh$_3$)$_4$, 2.0 M aq Na$_2$CO$_3$, n-BuOH, reflux; b is DCM, NBS; and c is 1-oxo-1,2,3,4-tetrahydroisoquinolin-6-ylboronic acid, PdCl$_2$(PPh$_3$)$_2$, Na$_2$CO$_2$, MeCN, H$_2$O.

In particular, a slurry of 2-amino-5-bromopridine (1.24 g, 4.67 mmol), 4-(ethylsulfonyl)phenylboronic acid (1.10 g, 5.14 mmol), and Pd(PPh$_3$)$_4$ (0.16 g, 0.13 mmol) in n-BuOH (20 mL) was treated with 2.0 M aq. Na$_2$CO$_3$ (4.5 mL). The reaction was sparged with dry N$_2$ under sonication for 10 min to degas, and then refluxed for 16 h at 100° C. At completion, the reaction was cooled to room temperature and concentrated to dryness. The residue was partitioned between EtOAc (50 mL) and water (30 mL). The layers were separated and the aqueous layer was extracted with EtOAc (2×50 mL). The combined organics were washed with brine (20 mL), dried over Na$_2$SO$_4$ and concentrated. The crude material was purified by flash chromatography over silica gel (30-100% EtOAc:hexane eluent) to provide 5-(4-(ethylsulfonyl)phenyl)pyridin-2-amine as a white solid (0.57 g, 47% yield). $^1$H NMR (300 MHz, MeOH) δ ppm 8.27-8.31 (m, 1H), 7.91-7.98 (m, 2H), 7.79-7.89 (m, 3 H), 6.71 (dd, J=8.7, 0.7 Hz, 1H), 3.30-3.35 (m, 2H), 3.24 (q, J=7.4 Hz, 2H), 1.25 (t, J=7.4 Hz, 3H); MS (EI) m/z: 263 [M+H]$^+$.

A room temperature solution of 5-(4-(ethylsulfonyl)phenyl)pyridin-2-amine (0.56 g, 2.14 mmol) in DCM (15 mL) was treated with NBS (0.42 g, 2.35 mmol) and the reaction was maintained for 1.5 h. At completion, mixture was washed with sat. aq. Na$_2$S$_2$O$_4$ solution (10 mL), followed by sat. aq. NaHCO$_3$ (10 mL) and brine (5 mL). The organic layer was dried over Na$_2$SO$_4$, then filtered and concentrated to 3-bromo-5-(4-(ethylsulfonyl)phenyl)pyridin-2-amine (560 mg, 77% yield) as an orange solid. $^1$H NMR (300 MHz, DMSO-$d_6$) δ ppm 8.37-8.49 (m, 1H), 8.15-8.25 (m, 1H), 7.90-7.96 (m, 2H), 7.85-7.90 (m, 2H), 6.60 (br. s, 2H), 3.34 (q, J=7.4 Hz, 2H), 1.11 (t, J=7.4 Hz, 3H); MS (EI) m/z: 343, 341 [M+H]$^+$.

A mixture of the 3-bromo-5-(4-(ethylsulfonyl)phenyl)pyridin-2-amine (100 mg, 0.29 mmol), 1-oxo-1,2,3,4-tetrahydroisoquinolin-6-ylboronic acid (75 mg, 0.29 mmol), PdCl$_2$(PPh$_3$)$_2$ (7.0 mg, 0.01 mmol) and Na$_2$CO$_3$ in 3:1 MeCN:H$_2$O was microwave heated at 150° C. for 3 min. At completion, the reaction mixture was filtered, then purified by preparatory HPLC to provide 6-(2-amino-5-(4-(ethylsulfonyl)phenyl)pyridin-3-yl)-3,4-dihydroisoquinolin-1(2H)-one as a pale yellow solid (48 mg, 41% yield) after reverse phase preparatory HPLC purification. $^1$H NMR (400 MHz, MeOD) δ ppm 8.37 (d, J=2.5 Hz, 1H), 8.06 (d, J=8.0 Hz, 1H), 7.94 (d, J=8.5 Hz, 2H), 7.89 (d, J=8.5 Hz, 2H), 7.81 (d, J=2.5 Hz, 1H), 7.53 (d, J=7.8 Hz, 1H), 7.49 (s, 1H), 3.56 (t, J=6.7 Hz, 2H), 3.19-3.27 (m, 2H), 3.07 (q, J=6.5 Hz, 2H), 1.25 (t, J=7.3 Hz, 3 H); MS (EI) m/z: 408 [M+H]$^+$.

6.8. Synthesis of 4-(6-amino-5-(1-oxo-1,2,3,4-tetrahydroisoquinolin-6-yl)pyridin-3-yl)-N,N-diethylbenzenesulfonamide

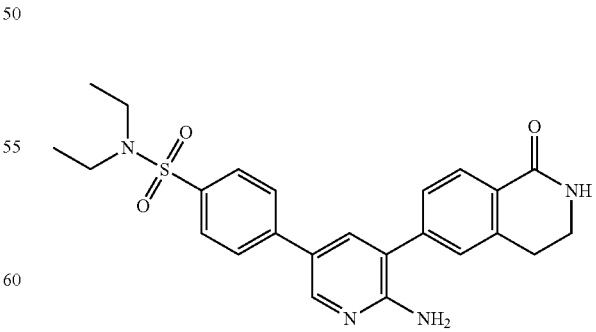

General method A was applied to 4-(N,N-diethylsulfamoyl)phenylboronic acid, providing 4-(6-amino-5-(1-oxo-1,2,3,4-tetrahydroisoquinolin-6-yl)pyridin-3-yl)-N,N-diethylbenzenesulfonamide after preparatory HPLC purification. $^1$H NMR (400 MHz, MeOD) δ ppm 8.33 (d, J=2.3 Hz, 1H), 8.06 (d, J=8.0 Hz, 1H), 7.85 (m, J=8.5 Hz, 2H), 7.76-7.82 (m, 3H), 7.53 (dd, J=8.0, 1.5 Hz, 1H), 7.48 (s, 1H), 4.10 (q, J=7.1 Hz, 4H), 3.56 (t, J=6.7 Hz, 2 H), 3.26 (q, J=7.0 Hz, 6H), 3.07 (t, J=6.7 Hz, 2H); MS (EI) m/z: 451 [M+H]$^+$.

6.9. Synthesis of 4-(6-amino-5-(1-hydroxyisoquinolin-6-yl)pyridin-3-yl)-N-ethylbenzenesulfonamide

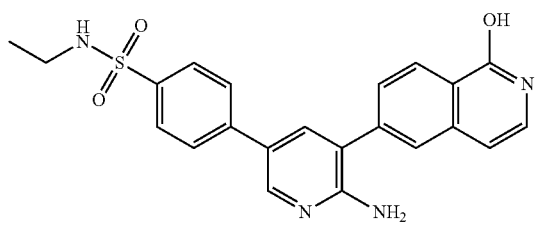 [SMILES: CCNS(=O)(=O)c1ccc(-c2cnc(N)c(-c3ccc4c(O)nccc4c3)c2)cc1]

General method C was applied to 4-(N-ethylsulfamoyl)phenylboronic acid and 6-(4,4,5,5-tetramethyl-1,3,2-dioxaborolan-2-yl)isoquinolin-1-ol to provide 4-(6-amino-5-(1-hydroxyisoquinolin-6-yl)pyridin-3-yl)-N-ethylbenzenesulfonamide. $^1$H NMR (400 MHz, DMSO-d$_6$) δ ppm 11.31 (d, J=5.3 Hz, 1H), 8.47 (d, J=2.3 Hz, 1H), 8.30 (d, J=8.3 Hz, 1H), 8.12 (s, 1H), 7.96 (d, J=8.3 Hz, 2H), 7.80-7.86 (m, 3H), 7.64 (dd, J=8.3, 1.5 Hz, 1H), 7.58 (dd, J=11.3, 5.5 Hz, 1H), 7.23 (dd, J=12.8, 6.8 Hz, 1H), 6.60 (d, J=7.0 Hz, 1H), 2.75-2.84 (m, 2 H), 0.98 (t, J=7.3 Hz, 3H); MS (EI) m/z: 421 [M+H]$^+$.

6.10. Synthesis of 4-(2-amino-5-(4-(N-cyclopropylsulfamoyl)phenyl)pyridin-3-yl)benzamide

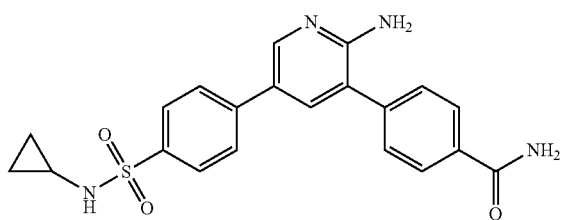 [SMILES: NC(=O)c1ccc(-c2cc(-c3ccc(S(=O)(=O)NC4CC4)cc3)cnc2N)cc1]

General method B was applied to 4-bromo-N-cyclopropylbenzenesulfonamide (41 mg, 0.15 mmol), 6-amino-5-(4-carbamoylphenyl)pyridin-3-ylboronic acid (53 mg, 0.15 mmol), to give 4-(2-amino-5-(4-(N-cyclopropylsulfamoyl)phenyl)pyridin-3-yl)benzamide as a white solid (29 mg, 41% yield). $^1$H NMR (400 MHz, DMSO-d$_6$) δ ppm 8.42 (d, J=2.3 Hz, 1H), 8.03 (br. s., 1H), 7.98 (d, J=8.3 Hz, 2H), 7.90 (d, J=8.5 Hz, 2H), 7.87 (d, J=2.5 Hz, 1H), 7.80 (d, J=8.5 Hz, 2H), 7.76 (d, J=1.5 Hz, 1H), 7.61 (d, J=8.3 Hz, 2H), 7.37 (br. s., 1H), 6.06 (br. s., 2H), 2.06-2.13 (m, 1H), 0.42-0.50 (m, 2H), 0.35-0.42 (m, 2H); MS (EI) m/z: 409 [M+H]$^+$.

6.11. Synthesis of 4-(6-amino-5-(1-oxo-1,2,3,4-tetrahydroisoquinolin-6-yl)pyridin-3-yl)-N-ethylbenzenesulfonamide

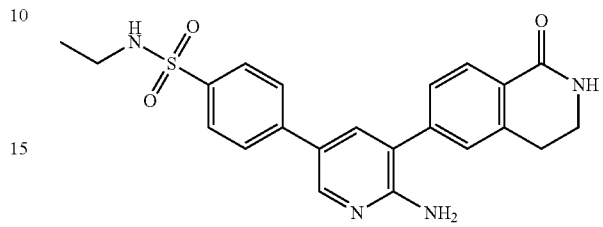

General method B was applied to 4-(6-amino-5-bromopyridin-3-yl)-N-ethylbenzenesulfonamide (50 mg, 0.141 mmol) and 4-(N-ethylsulfamoyl)phenylboronic acid (64 mg, 0.336 mmol) to provide 4-(6-amino-5-(1-oxo-1,2,3,4-tetrahydroisoquinolin-6-yl)pyridin-3-yl)-N-ethylbenzenesulfonamide as a white solid (28 mg, 47% yield) after purification by reverse phase preparatory HPLC. $^1$H NMR (400 MHz, METHANOL-d$_4$) δ ppm 8.35 (d, J=2.3 Hz, 1H), 8.08 (d, J=7.8 Hz, 1H), 7.90 (d, J=8.5 Hz, 2H), 7.79-7.84 (m, 3H), 7.48-7.58 (m, 2H), 3.57 (t, J=6.8 Hz, 2H), 3.08 (t, J=6.8 Hz, 2H), 2.93 (q, J=7.8 Hz, 2H), 1.08 (t, J=7.3 Hz, 3H); MS (EI) m/z: 423 [M+H]$^+$.

6.12. Synthesis of 2'-amino-5'-(4-(N-cyclopropylsulfamoyl)phenyl)-2,3'-bipyridine-5-carboxamide

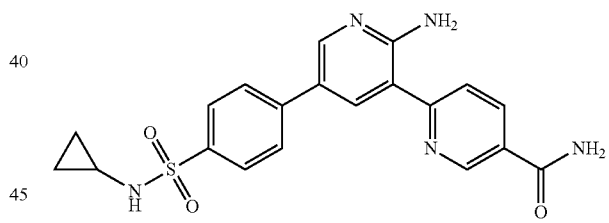

General method B was applied to 4-(6-amino-5-bromopyridin-3-yl)-N-cyclopropylbenzenesulfonamide (112 mg, 0.304 mmol) and 5-carbamoylpyridin-2-ylboronic acid (75 mg, 0.453 mmol) to provide 2'-amino-5'-(4-(N-cyclopropylsulfamoyl)phenyl)-[2,3'-bipyridine]-5-carboxamide as a white solid (35 mg, 28% yield) after purification by reverse phase preparatory HPLC. $^1$H NMR (400 MHz, DMSO-d$_6$) δ ppm 9.07-9.16 (m, 1H), 8.53 (d, J=2.3 Hz, 1H), 8.47 (d, J=2.3 Hz, 1H), 8.32 (dd, J=14.1, 10.8 Hz, 2H), 8.21 (br. s., 1H), 8.01 (d, J=8.5 Hz, 2H), 7.91 (d, J=2.5 Hz, 1H), 7.85 (d, J=8.3 Hz, 2H), 7.79 (br. s., 2H), 7.61 (br. s., 1H), 2.06-2.18 (m, 1H), 0.34-0.55 (m, 4H); MS (EI) m/z: 410 [M+H]$^+$.

6.13. Synthesis of 6-(2-amino-5-(1,1-dioxido-2,3-dihydrobenzo[d]isothiazol-5-yl)pyridin-3-yl)-3,4-dihydroisoquinolin-1(2H)-one The captioned compound was prepared by the method shown below.

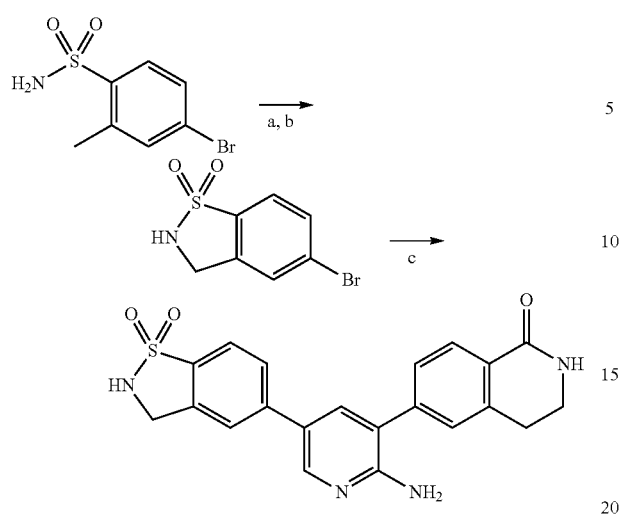

wherein:

a is AIBN, NBS, PhMe, 15 h; b is K₂CO₃, 12 h; c is Pd(PPh₃)₄, Na₂CO₃, (6-amino-5-(1-oxo-1,2,3,4-tetrahydroisoquinolin-6-yl)pyridin-3-yl)boronic acid.

To a solution of 4-bromo-2-methylbenzenesulfonamide (496 mg, 2.0 mmol) in toluene (10 mL) at room temperature was added AIBN (383 mg, 2.20 mmol) and N-bromosuccinimide (389 mg, 2.20 mmol). The mixture was heated to 90° C. for 2 h. At completion, the reaction was cooled to room temperature. Water (20 mL) was added and the layers were separated. The aqueous layer was extracted with EtOAc (3×20 mL). The combined organics were washed with brine (20 mL), dried over Na₂SO₄, and concentrated under reduced pressure to provide a pale yellow solid (170 mg, 26% yield) which was taken up in DMF (5 mL) and treated with K₂CO₃ (196 mg, 2.0 mmol). The reaction was stirred at room temperature overnight. After filtration and concentration, the residue was purified by flash chromatography over silica gel (4-10% MeOH/DCM eluent) to afford 5-bromo-2,3-dihydrobenzo[d]isothiazole 1,1-dioxide as a white solid (108 mg, 85% yield).

General method B was applied to 5-bromo-2,3-dihydrobenzo[d]isothiazole 1,1-dioxide (108 mg, 0.44 mmol) and (140 mg, 0.48 mmol) to provide 6-(2-amino-5-(1,1-dioxido-2,3-dihydrobenzo[d]isothiazol-5-yl)pyridin-3-yl)-3,4-dihydroisoquinolin-1(2H)-one after purification by reverse phase preparatory HPLC. ¹H NMR (400 MHz, METHANOL-d₄) δ ppm 8.35 (br. s, 1 H), 8.05-8.14 (m, 2H), 7.86 (s, 2H), 7.82 (s, 1H), 7.57 (s, 1H), 7.53 (s, 1H), 4.52 (s, 2H), 3.57 (t, J=6.8 Hz, 2H), 3.09 (t, J=6.5 Hz, 2H); MS (EI) m/z=407.5 [M+H]⁺

6.14. General Method D and Synthesis of 6'-amino-N-cyclopropyl-N-methyl-5'-(1-oxo-1,2,3,4-tetrahydroisoquinolin-6-yl)-[2,3'-bipyridine]-5-sulfonamide The captioned compound was prepared by general method D, represented below:

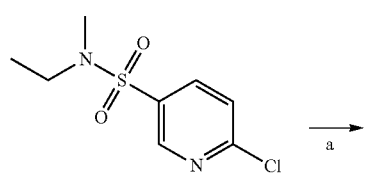

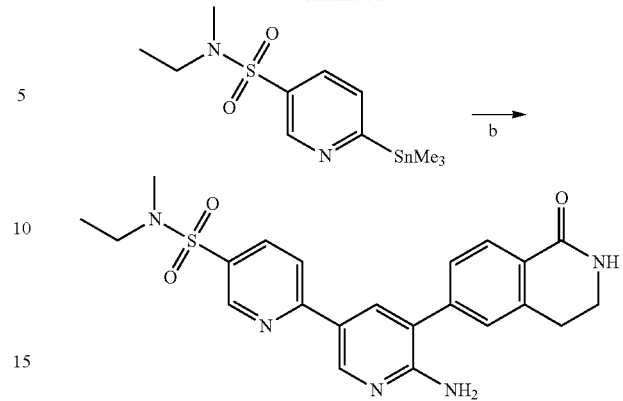

wherein:

a is Sn(Me)₄ and Pd(PPh₃)₄ dioxane, 90° C.; and b is Pd(PPh₃)₄, 6-(2-amino-5-bromopyridin-3-yl)-3,4-dihydroisoquinolin-1(2H)-one, dioxane, 90° C.

6-chloro-N-ethyl-N-methylpyridine-3-sulfonamide (2.34 g, 10.0 mmol), tetramethyl tin (1.08 g, 10.00 mmol) and Pd(PPh₃)₄ (572 mg, 0.50 mmol) were mixed in dioxane (5 mL). After degassing, the mixture was heated to 90° C. At completion, the reaction was cooled to room temperature and concentrated. The residue was then flashed over alumina (20-100% chloroform/hexane eluent) to afford N-ethyl-N-methyl-6-(trimethylstannyl)pyridine-3-sulfonamide (1.46 g, 40% yield).

A mixture of N-ethyl-N-methyl-6-(trimethylstannyl)pyridine-3-sulfonamide (225 mg, 0.6 mmol) and 6-(2-amino-5-bromopyridin-3-yl)-3,4-dihydroisoquinolin-1(2H)-one (190 mg, 0.6 mmol) and Pd(PPh₃)₄ (34 mg, 0.03 mmol) in dioxane (3 mL) was degassed and heated to 90° C. At completion, the reaction was cooled to room temperature and concentrated. The residue was purified by flash chromatography over silica gel to provide 6'-amino-N-ethyl-N-methyl-5'-(1-oxo-1,2,3,4-tetrahydroisoquinolin-6-yl)-[2,3'-bipyridine]-5-sulfonamide as a yellow solid (134 mg, 50% yield). ¹H NMR (400 MHz, DMSO-d₆) δ ppm 8.88 (dd, J=17.9, 2.1 Hz, 2H), 8.17-8.22 (m, 1H), 8.10-8.16 (m, 2H), 7.94 (d, J=7.8 Hz, 2H), 7.43-7.51 (m, 2H), 3.41 (s, 2H), 3.30 (s, 3H), 2.97 (t, J=6.4 Hz, 2H), 0.86 (t, J=7.3 Hz, 3H); MS (EI) m/z=438.5 [M+1]⁺.

6.15. Synthesis of 6-(5-amino-6-(1-oxo-1,2,3,4-tetrahydroisoquinolin-6-yl)pyrazin-2-yl)-N-ethyl-N,4-dimethylpyridine-3-sulfonamide

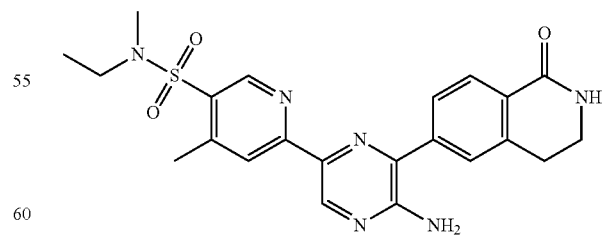

General method D was applied to N-ethyl-N,4-dimethyl-6-(trimethylstannyl)pyridine-3-sulfonamide (233 mg, 0.6 mmol) and 6-(2-amino-5-bromopyridin-3-yl)-3,4-dihydroisoquinolin-1(2H)-one (190 mg, 0.6 mmol) to give 6-(5-amino-6-(1-oxo-1,2,3,4-tetrahydroisoquinolin-6-yl)pyrazin- 2-yl)-N-ethyl-N,4-dimethylpyridine-3-sulfonamide as a yellow solid (41 mg, 33% yield) after purification by preparatory reverse phase HPLC. $^1$H NMR (400 MHz, DMSO-$d_6$) δ ppm 8.96 (s, 1H), 8.84 (s, 1H), 8.14 (s, 1H), 7.93-8.04 (m, 2H), 7.73 (d, J=8.0 Hz, 1H), 7.70 (s, 1H), 3.39-3.47 (m, 2H), 3.23 (q, J=7.3 Hz, 2H), 3.01 (t, J=6.5 Hz, 2H), 2.81 (s, 3 H), 2.61 (s, 3H), 1.09 (t, J=7.2 Hz, 3H); MS (EI) m/z=453 [M+1]$^+$.

6.16. Synthesis of 6'-amino-N-ethyl-N-methyl-5'-(6-oxo-5,6-dihydro-4H-thieno[2,3-c]pyrrol-2-yl)-[2,3'-bipyridine]-5-sulfonamide The captioned compound was prepared by the method shown below:

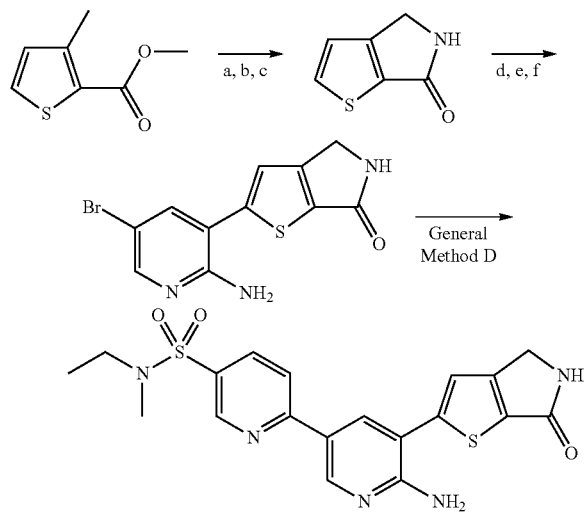

wherein:
a is AIBN, NBS, CCl$_4$; b is NH$_3$, MeOH, DMF; c is K$_2$CO$_3$, MeOH:EtOH (1:1); d is Br$_2$, HOAc, water e is tert-butyl (3-(4,4,5,5-tetramethyl-1,3,2-dioxaborolan-2-yl)pyridin-2-yl)carbamate, Pd(PPh$_3$)$_4$, 2.0 M aq. Na$_2$CO$_3$, n-BuOH (5 mL) and; f is NBS, DMF.

To a solution of methyl 3-methylthiophene-2-carboxylate (10.0 g, 64.0 mmol) in CCl$_4$ (100 mL) was added AIBN (180 mg, 1.1 mmol) and N-bromosuccinimide (11.4 g, 64.0 mmol). The reaction mixture was refluxed for 10 min, and then an additional portion of AIBN (460 mg, 2.8 mmol) was added. This reaction was heated overnight at 90° C. under a reflux condenser. At completion, the reaction was filtered over a short plug of silica gel (100% DCM eluent). The filtrate was concentrated and purified by flash chromatography over silica gel (2% EtOAc/hexane eluent) to afford methyl 3-(bromomethyl)thiophene-2-carboxylate (9.5 g, 63% yield) as a white solid. $^1$H NMR (400 MHz, METHANOL-$d_4$) δ ppm 7.66 (d, J=5.0 Hz, 1H), 7.23 (d, J=5.0 Hz, 1H), 4.95 (s, 2H), 3.89 (s, 3H); MS (EI) m/z=236.1 [M+1]$^+$.

To a solution of 3-(bromomethyl)thiophene-2-carboxylate (9.3 g, 39.6 mmol) in DMF (150 mL) was added 7.0 N NH$_3$ in MeOH (150 mL). After stirring at room temperature for 1 h, the reaction was concentrated and purified by flash chromatography over silica gel (5%-10% MeOH/DCM) to provide methyl 3-(aminomethyl)thiophene-2-carboxylate (4.86 g, 72% yield) as a white solid. $^1$H NMR (400 MHz, METHANOL-$d_4$) δ ppm 7.83 (d, J=5.0 Hz, 1H), 7.28 (d, J=5.0 Hz, 1H), 4.45 (s, 2H), 3.94 (s, 3H); MS (EI) m/z=172.2 [M+1]$^+$.

A mixture of methyl 3-(aminomethyl)thiophene-2-carboxylate (4.5 g, 26.3 mmol) and K$_2$CO$_3$ (3.64 g, 26.3 mmol) in 1:1 MeOH:EtOH (600 mL) was heated overnight under reflux. The reaction was concentrated and purified by flash chromatography over silica gel (50-100% EtOAc/hexane) to yield 4H-thieno[2,3-c]pyrrol-6(5H)-one (2.2 g, 60% yield) as a white solid. $^1$H NMR (400 MHz, METHANOL-$d_4$) δ ppm 7.87 (d, J=4.8 Hz, 1H), 7.17 (d, J=4.8 Hz, 1H), 4.39 (s, 2H); MS (EI) m/z=140.2 [M+1]$^+$.

A solution of 4H-thieno[2,3-c]pyrrol-6(5H)-one (1.0 g, 7.2 mmol) in acetic acid (9 mL) and water (7 mL) was cooled to 0° C. Bromine (407 μL, 7.92 mmol) was added and the reaction was maintained at 0° C. for 1.5 h. At completion, water (30 mL) was added and the mixture was and extracted with EtOAc (2×50 mL). The combined organics were washed with 5% aq. Na$_2$SO$_3$ (30 mL), sat. aq. NaHCO$_3$ (30 mL) and brine (30 mL), then dried over Na$_2$SO$_4$, filtered, concentrated. The crude material was purified by flash chromatography over silica gel (5% MeOH/DCM) to yield 2-bromo-4H-thieno[2,3-c]pyrrol-6(5H)-one (1.3 g, 83% yield) as a white solid. $^1$H NMR (400 MHz, METHANOL-$d_4$) δ ppm 7.28 (s, 1H), 4.39 (s, 3H); MS (EI) m/z=140.2 [M+1]$^+$.

A solution of tert-butyl (3-(4,4,5,5-tetramethyl-1,3,2-dioxaborolan-2-yl)pyridin-2-yl)carba mate (736 mg, 2.3 mmol), 2-bromo-4H-thieno[2,3-c]pyrrol-6(5H)-one (500 mg, 2.3 mmol) and Pd(PPh$_3$)$_4$ (40 mg, 0.035 mmol) in n-BuOH (5 mL) and 2.0 M Na$_2$CO$_3$ (4.6 mL) was degassed and the resulting reaction mixture was refluxed at 110° C. for 2 h. Upon completion, the reaction was cooled to room temperature, filtered, and washed with MeOH (10 mL) and water (2×10 mL). The solid was dried under high vacuum yielding 2-(2-aminopyridin-3-yl)-4H-thieno[2,3-c]pyrrol-6(5H)-one (383 mg, 72% yield) as a light brown solid. $^1$H NMR (400 MHz, DMSO-$d_6$) δ ppm 8.40 (br. s., 1H), 8.00 (dd, J=5.0, 1.8 Hz, 1H), 7.52 (dd, J=7.3, 1.8 Hz, 1H), 7.36 (s, 1H), 6.66 (dd, J=7.4, 4.9 Hz, 1H), 5.99 (s, 2H), 4.32 (s, 2H); MS (EI) m/z=232.3 [M+1]$^+$.

To a solution of 2-(2-aminopyridin-3-yl)-4H-thieno[2,3-c]pyrrol-6(5H)-one (350 mg, 1.52 mmol) in DMF (5 mL) was added NBS (297 mg, 1.67 mmol). At completion, the reaction was concentrated and the residue was taken up in 20% MeOH/DCM (10 mL) then filtered and concentrated. After drying under high vacuum, 2-(2-aminopyridin-3-yl)-4H-thieno[2,3-c]pyrrol-6(5H)-one (313 mg, 66% yield) was isolated as a brown solid. $^1$H NMR (400 MHz, DMSO-$d_6$) δ ppm 8.44 (br. s., 1H), 8.08 (d, J=2.5 Hz, 1H), 7.67 (d, J=2.3 Hz, 1H), 7.39 (s, 1H), 6.27 (br. s., 2H), 4.32 (s, 2H); MS (EI) m/z=311.2 [M+1]$^+$.

General method D was applied to N-ethyl-N-methyl-6-(trimethylstannyl)pyridine-3-sulfonamide (218 mg, 0.6 mmol) and 2-(2-amino-5-bromopyridin-3-yl)-4H-thieno[2,3-c]pyrrol-6(5H)-one (186 mg, 0.6 mmol) to give 6'-amino-N-ethyl-N-methyl-5'-(6-oxo-5,6-dihydro-4H-thieno[2,3-c]pyrrol-2-yl)-[2,3'-bipyridine]-5-sulfonamide as a yellow solid (94 mg, 38% yield) after purification by preparatory reverse phase HPLC. $^1$H NMR (400 MHz, DMSO-$d_6$) δ ppm 8.91 (d, J=1.5 Hz, 1H), 8.87 (d, J=2.3 Hz, 1H), 8.44 (s, 1H), 8.26 (d, J=2.3 Hz, 1H), 8.10-8.20 (m, 2H), 7.43 (s, 1H), 6.65

(s, 2H), 4.35 (s, 2H), 3.30 (s, 4H), 3.09 (dd, J=14.3, 7.0 Hz, 2H), 2.72 (s, 3H), 1.06 (t, J=7.0 Hz, 3H); MS (EI) m/z=430 [M+1]+.

6.17. Synthesis of 1-(4-(5-amino-6-(1-oxo-1,2,3,4-tetrahydroisoquinolin-6-yl)pyrazin-2-yl)phenyl)cyclopentanecarbonitrile

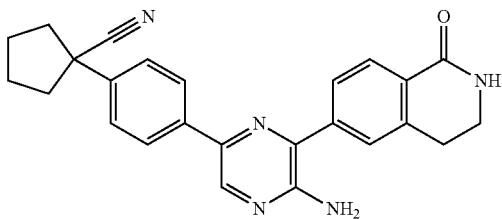 [SMILES: N#CC1(c2ccc(-c3cnc(N)c(-c4ccc5c(c4)CCNC5=O)n3)cc2)CCCC1]

General method A was applied to 1-(4-(4,4,5,5-tetramethyl-1,3,2-dioxaborolan-2-yl)phenyl)cyclopentanecarbonitrile (149 mg, 0.5 mmol) and 6-(3-amino-6-bromopyrazin-2-yl)-3,4-dihydroisoquinolin-1(2H)-one (180 mg, 0.5 mmol) to give 1-(4-(5-amino-6-(1-oxo-1,2,3,4-tetrahydroisoquinolin-6-yl)pyrazin-2-yl)phenyl)cyclopentanecarbonitrile as a yellow solid (89 mg, 0.22 mmol, 44% yield) after purification by preparatory reverse phase HPLC. $^1$H NMR (400 MHz, DMSO-$d_6$) δ ppm 8.60 (s, 1H), 8.02 (d, J=8.3 Hz, 3H), 7.96 (d, J=8.0 Hz, 1H), 7.72-7.78 (m, 1H), 7.70 (s, 1H), 7.57 (m, J=8.5 Hz, 3H), 3.38-3.45 (m, 2H), 2.99 (t, J=6.4 Hz, 2H), 2.37-2.46 (m, 2H), 2.03-2.16 (m, 2H), 1.84-1.94 (m, 4H); MS (EI) m/z=410.5 [M+1]+.

6.18. Synthesis of 6'-amino-N-(cyclopropylmethyl)-N-methyl-5'-(1-oxo-1,2,3,4-tetrahydroisoquinolin-6-yl)-[2,3'-bipyridine]-5-sulfonamide

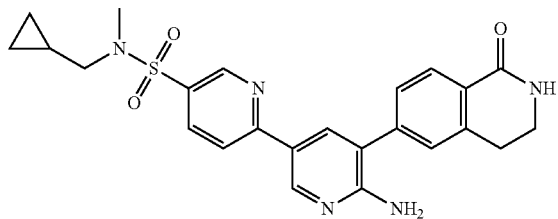 [SMILES: CN(CC1CC1)S(=O)(=O)c1ccc(-c2cnc(N)c(-c3ccc4c(c3)CCNC4=O)c2)nc1]

General method D was applied to N-(cyclopropylmethyl)-N-methyl-6-(trimethylstannyl)pyridine-3-sulfonamide (233 mg, 0.6 mmol) and 6-(2-amino-5-bromopyridin-3-yl)-3,4-dihydroisoquinolin-1(2H)-one (190 mg, 0.6 mmol) to give 6'-amino-N-(cyclopropylmethyl)-N-methyl-5'-(1-oxo-1,2,3,4-tetrahydroisoquinolin-6-yl)-[2,3'-bipyridine]-5-sulfonamide as a yellow solid (127 mg, 0.27 mmol, 46% yield) after purification by reverse phase preparatory HPLC. $^1$H NMR (400 MHz, DMSO-$d_6$) δ ppm 8.87 (d, J=1.5 Hz, 1H), 8.84 (d, J=2.3 Hz, 1H), 8.05-8.19 (m, 3H), 7.90-7.98 (m, 2H), 7.43-7.50 (m, 2H), 6.34 (s, 2H), 3.38-3.45 (m, 2H), 2.97 (t, J=1.0 Hz, 2H), 2.91 (d, J=6.8 Hz, 2H), 2.80 (s, 3H), 0.85-0.96 (m, 1H), 0.43-0.51 (m, 2H), 0.16-0.21 (m, 2H); MS (EI) m/z=464.5 [M+1]+.

6.19. Synthesis of 6'-amino-N-ethyl-N,4-dimethyl-5'-(1-oxo-1,2,3,4-tetrahydroisoquinolin-6-yl)-[2,3'-bipyridine]-5-sulfonamide

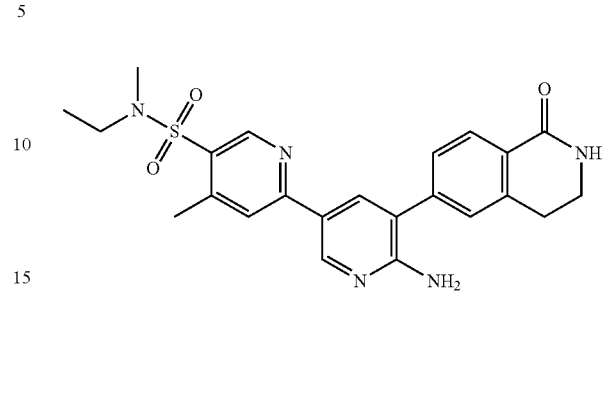

General method D was applied to N-ethyl-N,4-dimethyl-6-(trimethylstannyl)pyridine-3-sulfonamide (226 mg, 0.6 mmol) and 6-(2-amino-5-bromopyridin-3-yl)-3,4-dihydroisoquinolin-1(2H)-one (190 mg, 0.6 mmol) to give 6'-amino-N-ethyl-N,4-dimethyl-5'-(1-oxo-1,2,3,4-tetrahydroisoquinolin-6-yl)-[2,3'-bipyridine]-5-sulfonamide as a yellow solid (41 mg, 33% yield) after purification by reverse phase preparatory HPLC. $^1$H NMR (400 MHz, DMSO-$d_6$) δ ppm 8.84-8.88 (m, 2H), 8.56 (s, 1H), 8.23 (s, 1H), 8.06 (br. s., 1H), 8.00 (d, J=7.8 Hz, 1H), 7.49-7.56 (m, 2H), 3.38-3.48 (m, 2H), 3.23 (q, J=7.0 Hz, 2H), 3.00 (t, J=6.3 Hz, 2H), 2.81 (s, 3H), 2.61 (s, 3H), 1.09 (t, J=7.0 Hz, 3H); MS (EI) m/z=452.5 [M+1]+.

6.20. General Method E and Synthesis of (S)-4-(6-amino-5-(3-methyl-5-oxo-2,3,4,5-tetrahydro-1H-benzo[e]-[1,4]diazepin-8-yl)pyridin-3-yl)-N-cyclopropylbenzenesulfonamide The captioned compound was prepared by general method E, represented below:

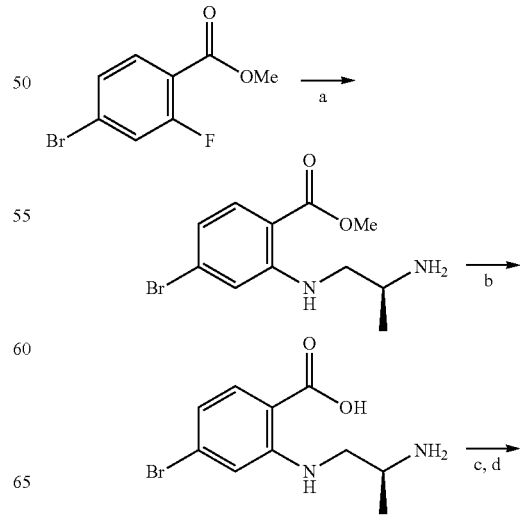

-continued

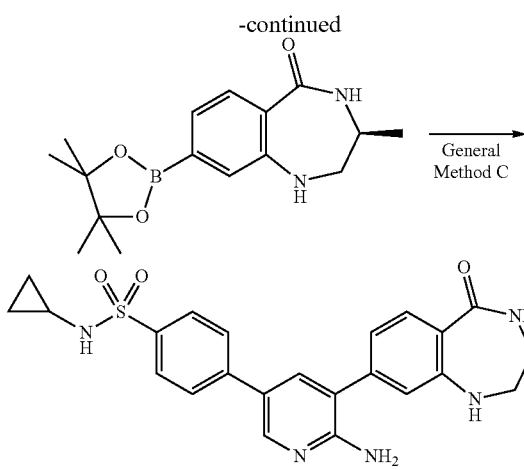

wherein:

a is (S)-propane-1,2-diamine, DMF, microwave heating; b is NaOH, MeOH, 70° C., 2 h; c is HATU, DMF; d is Pd(dba)$_3$, (Bpin)$_2$, 90° C.

A slurry of methyl 4-bromo-2-fluorobenzoate (4.66 mg, 20.0 mmol) (S)-propane-1,2-diamine (2.22 g, 30 mmol) and K$_2$CO$_3$ (2.94 g, 3.0 mmol) was microwave heated at 140° C. for 15 min. After filtration and concentration, the residue was purified by flash chromatography on silica (2-10% MeOH/DCM eluent) to provide (S)-methyl 2-((2-aminopropyl)amino)-4-bromobenzoate (2.66 g, 9.20 mmol) as a white oily solid. This material was dissolved in methanol (160 mL) and treated with NaOH (13.5 g, 200.0 mmol), then heated to 70° C. overnight. At completion, the reaction was neutralized to pH~7 with conc. aq. HCl and the solid was filtered and washed with MeOH. The combined filtrate was concentrated to provide (S)-2-((2-aminopropyl)amino)-4-bromobenzoic acid as a white solid. This solid was used without further purification (2.5 g, 46% yield, 2 steps).

To a solution of the crude (S)-2-((2-aminopropyl)amino)-4-bromobenzoic acid (544 mg, 2.0 mmol) and Et$_3$N (731 mg, 7.24 mmol) in DMF was added HATU (829 mg, 2.18 mmol). After 30 min, the reaction mixture was concentrated and purified by flash chromatography on silica gel (2-10% MeOH/DCM eluent) to provide (S)-8-bromo-3-methyl-3,4-dihydro-1H-benzo[e][1,4]diazepin-5(2H)-one as a white oily solid (464 mg, 91% yield). This material was dissolved in dioxane (20 mL), then treated with Pd2(dba)$_3$ (83 mg, 0.09 mmol), PCy$_3$ (121 mg, 0.43 mmol), diboron pinacol ester (595 mg, 2.35 mmol) and KOAc (532 mg, 5.43 mmol), then heated at 90° C. for 2 h. At completion, the reaction was cooled to room temperature, then filtered and concentrated. The crude material was flashed over silica gel (2-10% MeOH/DCM eluent) to provide (S)-3-methyl-8-(4,4,5,5-tetramethyl-1,3,2-dioxaborolan-2-yl)-3,4-dihydro-1H-benzo[e][1,4]diazepin-5(2H)-one (527 mg, 96% yield) as a yellow solid.

General method C was applied to (S)-3-methyl-8-(4,4,5,5-tetra methyl-1,3,2-dioxaborolan-2-yl)-3,4-dihydro-1H-benzo[e][1,4]diazepin-5(2H)-one (303 mg, 0.7 mmol) and 4-(6-amino-5-bromopyridin-3-yl)-N-cyclopropylbenzenesulfonamide to give (S)-4-(6-amino-5-(3-methyl-5-oxo-2,3,4,5-tetrahydro-1H-benzo[e][1,4]diazepin-8-yl)pyridin-3-yl)-N-cyclopropylbenzenesulfonamide as a yellow solid (180 mg, 33% yield) after purification by reverse phase preparatory HPLC. MS (EI) m/z=464.6 [M+1]$^+$.

6.21. Synthesis of 6'-amino-N-ethyl-N-methyl-5'-(7-oxo-4,5,6,7-tetrahydrothieno[2,3-c]pyridin-2-yl)-[2,3'-bipyridine]-5-sulfonamide The captioned compound was prepared the method shown below:

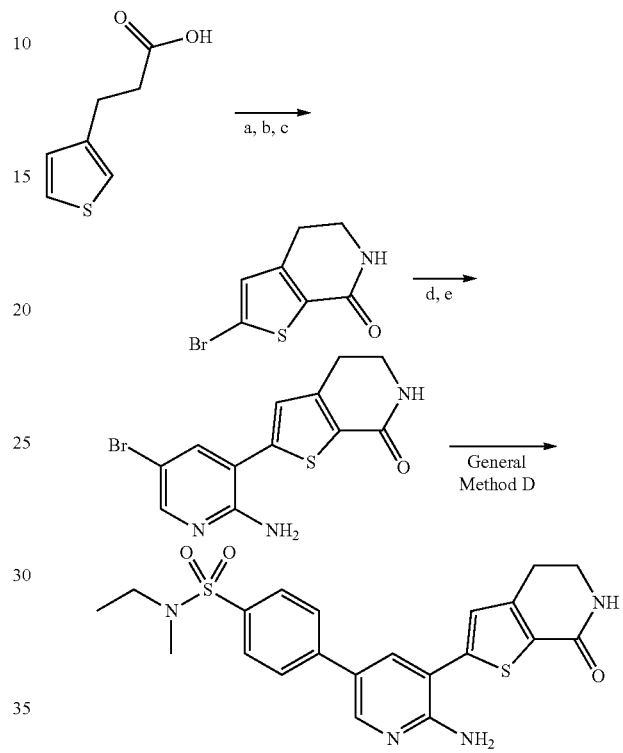

wherein:
a is P$_2$O$_5$, MsOH; b is H$_2$NOH—HCl, NaOAc, MeOH, then PPA, 130° C.; c is Br$_2$, HOAc; d is tert-butyl (3-(4,4,5,5-tetramethyl-1,3,2-dioxaborolan-2-yl)pyridin-2-yl)carbamate, Pd(PPh$_3$)$_4$, aq. Na$_2$CO$_3$, n-BuOH, 100° C.; and e is NBS, DMF.

To a suspension of P$_2$O$_5$ (25.4 g, 179.0 mmol) in methanesulfonic acid (100 mL) was added 3-(thiophen-3-yl)propanoic acid (5.0 g, 32.0 mmol) and the reaction was stirred at room temperature for 1 h. At completion, the reaction was concentrated and the residue was purified by flash chromatography (20-30% EtOAc/hexane eluent) to give 4H-cyclopenta[b]thiophen-6(5H)-one (1.34 g, 30% yield) as a brown solid. $^1$H NMR (300 MHz, MeOH) δ ppm 8.14 (d, J=4.8 Hz, 1H), 7.17 (d, J=4.8 Hz, 1H), 2.94-3.15 (m, 4H); MS (EI) m/z=139.2 [M+1]$^+$.

A solution of 4H-cyclopenta[b]thiophen-6(5H)-one (1.34 g, 9.7 mmol), hydroxylamine HCl (1.45 g, 20.8 mmol) and NaOAc (7.3 g, 89.0 mmol) in MeOH (150 mL) was stirred overnight at room temperature. The reaction was then concentrated under reduced pressure, taken up in EtOAc (100 mL) and filtered over a plug of silica gel, eluting with EtOAc. The filtrate was concentrated, taken up in polyphosphoric acid (100 g) and heated for 2 h at 130° C. Upon completion, the reaction was quenched by pouring over ice water (100 mL). The aqueous mixture was extracted with DCM (2×100 mL) and the combined extracts were washed with 0.1 M NaOH (100 mL), dried over Na$_2$SO$_4$, then filtered and concentrated. 5,6-dihydrothieno[2,3-c]pyridin-7(4H)-one (837 mg, 55% yield) was isolated as a white solid after purification by flash chromatography over silica gel (20-30% EtOAc/hexane eluent). $^1$H NMR (300 MHz, MeOH) δ ppm 7.69 (d, J=5.0 Hz, 1H), 7.06 (d, J=5.0 Hz, 1H), 3.57 (t, J=7.1 Hz, 2H), 2.94 (t, J=7.1 Hz, 2H); MS (EI) m/z=154.2 [M+1]$^+$.

To a 0° C. solution of 5,6-dihydrothieno[2,3-c]pyridin-7 (4H)-one (820 mg, 5.36 mmol) in HOAc (7 mL) and (5 mL) water was added bromine (303 μL, 5.9 mmol) and the reaction was stirred 1.5 h. The reaction was diluted in water (30 mL) and the aqueous mixture was extracted with EtOAc (2×50 mL). The combined organics were washed with 5% aq. Na$_2$SO$_3$ (40 mL), sat. aq. NaHCO$_3$ (40 mL), and brine (40 mL). The organic was dried over Na$_2$SO$_4$, then filtered and concentrated. After purification by flash chromatography over silica gel (50-100% EtOAc/hexane eluent), 2-bromo-5,6-dihydrothieno[2,3-c]pyridin-7(4H)-one (906 mg, 73% yield) was isolated as a white solid. $^1$H NMR (400 MHz, METHANOL-d$_4$) δ ppm 7.10 (s, 1H), 3.55 (t, J=7.0 Hz, 2H), 2.88 (t, J=7.0 Hz, 2H); MS (EI) m/z=233.1 [M+1]$^+$.

A solution of tert-butyl (3-(4,4,5,5-tetra methyl-1,3,2-dioxaborolan-2-yl)pyridin-2-yl)carbamate (416 mg, 1.3 mmol), 2-bromo-5,6-dihydrothieno[2,3-c]pyridin-7(4H)-one (300 mg, 1.3 mmol) and Pd(PPh$_3$)$_4$ (23 mg, 0.02 mmol) in n-BuOH (3 mL) and 2M Na$_2$CO$_3$ (3 mL) was degassed under bubbling nitrogen and the reaction was heated 2 h at 100° C. Upon completion, the reaction was filtered and concentrated under reduced pressure, then partitioned between DCM (10 mL) water (10 mL). The layers were separated and the aqueous layer was extracted with DCM (3×10 mL). The combined organics were dried over Na$_2$SO$_4$ and concentrated. The concentrate was slurried in EtOAc, sonicated and filtered to afford 2-(2-aminopyridin-3-yl)-5,6-dihydrothieno[2,3-c]pyridin-7(4H)-one (281 mg, 88% yield) as a white solid. $^1$H NMR (300 MHz, MeOH) δ ppm 7.99 (dd, J=5.0, 1.3 Hz, 1H), 7.62 (dd, J=7.5, 1.4 Hz, 1H), 7.25 (s, 1H), 6.76 (dd, J=7.5, 5.1 Hz, 1H), 3.61 (t, J=7.0 Hz, 2H), 2.97 (t, J=7.1 Hz, 2H); MS (EI) m/z=246.3 [M+1]$^+$.

To a solution of 2-(2-aminopyridin-3-yl)-5,6-dihydrothieno[2,3-c]pyridin-7(4H)-one (250 mg, 1.02 mmol) in DMF (3 ml) was added NBS (199 mg, 1.12 mmol). The reaction was stirred at room temperature for 1 h, then concentrated and taken up in DCM (10 mL). The organic solution was washed with a sat. aq. Na$_2$S$_2$O$_3$, then dried over Na$_2$SO$_4$, and concentrated to give 2-(2-amino-5-bromopyridin-3-yl)-5,6-dihydrothieno[2,3-c]pyridin-7(4H)-one (320 mg, 97% yield) as an orange solid. $^1$H NMR (400 MHz, DMSO-d$_6$) δ ppm 8.06 (d, J=2.0 Hz, 1H), 7.73 (br. s., 1H), 7.66 (d, J=1.8 Hz, 1H), 7.29 (s, 1H), 6.23 (br. s., 2H), 3.40-3.50 (m, 2H), 2.83 (t, J=6.9 Hz, 2H); MS (EI) m/z=325.2 [M+1]$^+$.

The final step of general method D was applied to N-ethyl-N-methyl-6-(trimethylstannyl)pyridine-3-sulfonamide (233 mg, 0.6 mmol) and 2-(2-amino-5-bromopyridin-3-yl)-5,6-dihydrothieno[2,3-c]pyridin-7(4H)-one (194 mg, 0.6 mmol) to give 6'-amino-N-ethyl-N-methyl-5'-(7-oxo-4,5,6,7-tetrahydrothieno[2,3-c]pyridin-2-yl)-[2,3'-bipyridine]-5-sulfonamide as a yellow solid (140 mg, 0.31 mmol, 53% yield) after purification by reverse phase preparatory HPLC. $^1$H NMR (400 MHz, DMSO-d$_6$) δ ppm 8.91 (d, J=2.0 Hz, 1H), 8.85 (d, J=2.3 Hz, 1H), 8.26 (d, J=2.3 Hz, 1H), 8.10-8.19 (m, 2H), 7.73 (br. s, 1H), 7.33 (s, 1H), 6.62 (s, 2H), 3.44-3.50 (m, 2H), 3.09 (s, 2H), 2.86 (t, J=1.0 Hz, 1H), 2.72 (s, 3H), 1.01-1.09 (m, 3H); MS (EI) m/z=444.5 [M+1]$^+$.

6.22. General Method F and Synthesis of 4-(4-(5-amino-6-(5-oxo-2,3,4,5-tetrahydro-1H-benzo[e][1,4]diazepin-8-yl)pyrazin-2-yl)phenyl)tetrahydro-2H-pyran-4-carbonitrile The captioned compound was prepared by general method F, represented below:

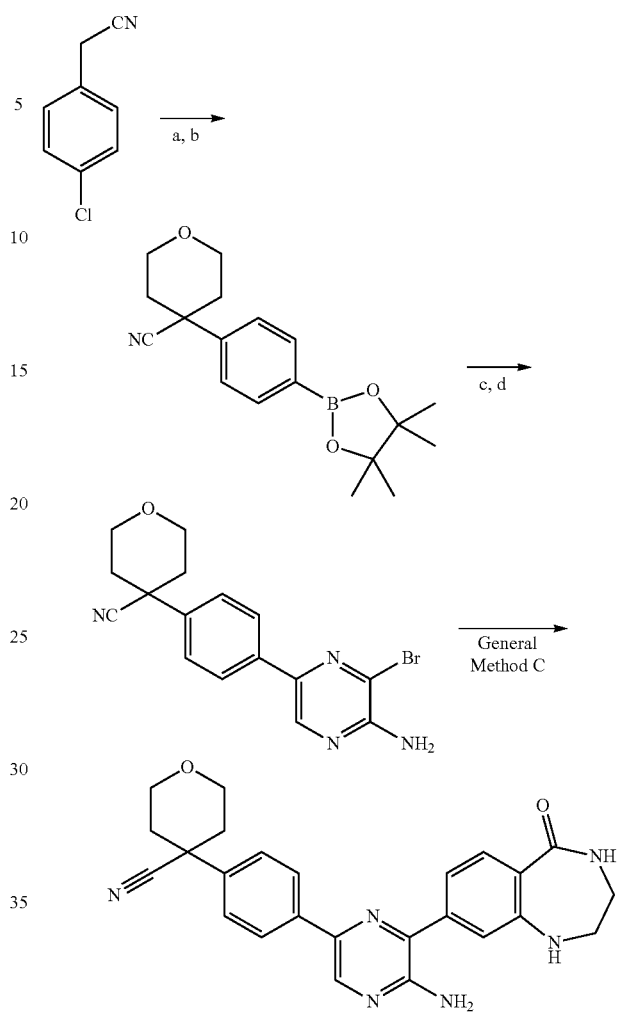

wherein:
a is NaH, ClCH$_2$CH$_2$OCH$_2$CH$_2$Cl,DMSO, 15 h; b is Pd(dppf)Cl$_2$, (BPin)$_2$, KOAc, 90° C., 2 h; c is Pd(PPh$_3$)$_4$, Na$_2$CO$_3$, 2-aminopyrizine, 90° C., 2 h; d is NBS, DMF, rt, 2 h.

To a stirred suspension of 2-(4-chlorophenyl)acetonitrile (3.06 g, 20.3 mmol) at 0° C. in DMSO (200 mL) was added NaH (1.79 g, 60% in mineral oil, 44.6 mmol). The reaction was stirred at 0° C. for 15 min then at room temperature for 30 min, resulting in a dark purple solution. To this solution was added 1-chloro-2-(2-chloroethoxy)ethane (3.18 g, 22.33 mmol) dropwise. The resulting mixture was stirred at room temperature overnight before diluting with 50 mL water and neutralizing to pH~7.0 with 1.0 M aq. HCl. The reaction was extracted with Et$_2$O (3×200 mL) and the combined organics were washed with brine (200 mL), dried over Na$_2$SO$_4$, and concentrated. The residue was purified by flash chromatography on silica gel (10-30% EtOAc/hexane eluent) to provide 4-(4-chlorophenyl)tetrahydro-2H-pyran-4-carbonitrile as a yellow crystalline solid (4.01 g, 89% yield) (Note: This compound does not ionize well on LC/MS. It does not have intense UV absorption at 220 nM. The TLC R$_f$ is 0.6 in 30% EA/Hexane).

A solution of 4-(4-chlorophenyl)tetrahydro-2H-pyran-4-carbonitrile (889 mg, 4.0 mmol), Pd(dba)$_2$ (138 mg, 0.24 mmol), PCy$_3$ (268 mg, 0.96 mmol), diboron pinacol ester (1.21 g, 4.8 mmol) and KOAc (1.18 g, 12.0 mmol) in 16 mL dioxane was microwave heated to 150° C. for 15 min. The resulting mixture was filtered, then concentrated and purified by flash chromatography on silica (2-5% MeOH/DCM eluent) to provide 4-(4-(4,4,5,5-tetramethyl-1,3,2-dioxaborolan-2-yl)phenyl)tetrahydro-2H-pyran-4-carbonitrile as a yellow crystalline solid (1.01 g, 81% yield).

A solution of 4-(4-(4,4,5,5-tetramethyl-1,3,2-dioxaborolan-2-yl)phenyl)tetrahydro-2H-pyran-4-carbonitrile (1.53 g, 4.86 mmol), Pd(PPh$_3$)$_4$ (271 mg, 0.24 mmol), 2.0 M aq. Na$_2$CO$_3$ (4.9 mL) and the 5-bromopyrazin-2-amine (846 mg, 4.86 mmol) were combined in n-BuOH (20 mL). The slurry was degassed for 10 min under a bubbling stream of anhydrous nitrogen, then heated at 90° C. for 2 h. The resulting mixture was filtered, concentrated and purified by flash chromatography on silica (1-5% MeOH/DCM eluent) to provide 4-(4-(5-aminopyrazin-2-yl)phenyl)tetrahydro-2H-pyran-4-carbonitrile (1.08 g, 79% yield).

To a solution of 4-(4-(5-aminopyrazin-2-yl)phenyl)tetrahydro-2H-pyran-4-carbonitrile (1.08 m, 3.84 mmol) in DMF (30 mL) was added N-bromosuccinimide (747 mg, 4.22 mmol) in one portion. The reaction was then stirred at room temperature for 1 h. At completion, the mixture was poured over ice (50 mL) and stirred for 20 min. After filtration and washing with water and drying under vacuum, 4-(4-(5-amino-6-bromopyrazin-2-yl)phenyl)tetrahydro-2H-pyran-4-carbonitrile was obtained as obtained as a dark brown solid (1.37 g, 100% yield).

General method C was applied to 4-(4-(5-amino-6-bromopyrazin-2-yl)phenyl)tetrahydro-2H-pyran-4-carbonitrile (215 mg, 0.6 mmol) and 8-(4,4,5,5-tetra methyl-1,3,2-dioxaborolan-2-yl)-3,4-dihydro-1H-benzo[e][1,4]diazepin-5 (2H)-one (173 mg, 0.6 mmol) to provide 4-(4-(5-amino-6-(5-oxo-2,3,4,5-tetrahydro-1H-benzo[e][1,4]diazepin-8-yl)pyrazin-2-yl)phenyl)tetrahydro-2H-pyran-4-carbonitrile as a yellow solid (87 mg, 33% yield). $^1$H NMR (400 MHz, CHLOROFORM-d) δ ppm 8.47 (s, 1H), 8.14 (d, J=8.3 Hz, 1H), 8.01 (d, J=8.3 Hz, 2 H), 7.58 (d, J=8.3 Hz, 2H), 7.21 (d, J=8.3 Hz, 1H), 7.04 (s, 1H), 6.40 (br. s., 1H), 4.93 (br. s., 2H), 4.57 (br. s., 1H), 4.12 (d, J=8.8 Hz, 2H), 3.94 (t, J=11.7 Hz, 2H), 3.50-3.73 (m, 4 H), 2.02-2.26 (m, 4H); MS (EI) m/z=441.5 [M+1]$^+$.

6.23. Synthesis of 2'-amino-5'-(4-(N-cyclopropylsulfamoyl)phenyl)-[2,3'-bipyridine]-5-carboxamide

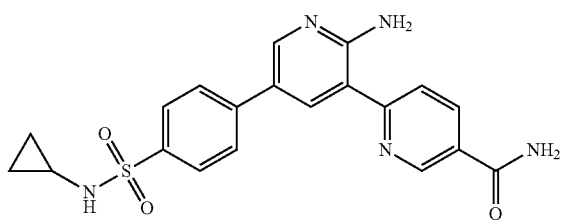 [SMILES: NC(=O)c1ccc(-c2cc(-c3ccc(S(=O)(=O)NC4CC4)cc3)cnc2N)nc1]

A mixture of 2-amino-5-bromopyridine (3.58 g, 20.7 mmol), N-cyclopropyl-4-(4,4,5,5-tetramethyl-[1,3,2]dioxaborolan-2-yl)-benzenesulfonamide (5.00 g, 20.7 mmol), sodium carbonate (3.29 g, 31.05 mmol), and PdCl$_2$(PPh$_3$)$_2$ (0.436 g, 0.62 mmol) in 3:1 acetonitrile:water was microwave heated at 80° C. for 20 min, and then at 100° C. for 15 min. The reaction was then heated in an oil bath at 80° C. for 16 h. The reaction was cooled to room temperature and filtered. The solid was washed with methanol (10 mL), and the combined filtrates were concentrated. The crude material was purified by flash chromatography over silica gel (0-5% MeOH/DCM) to give 4-(6-aminopyridin-3-yl)-N-cyclopropylbenzenesulfonamide (2.08 g, 35% yield). $^1$H NMR (400 MHz, METHANOL-d$_4$) δ ppm 8.27 (d, J=2.01 Hz, 1H), 7.88-7.95 (m, 2H), 7.85 (d, J=2.51 Hz, 1H), 7.81-7.84 (m, 1H), 7.71-7.79 (m, 2H), 6.45-6.88 (m, 1H), 1.89-2.41 (m, 1H), 0.13-0.82 (m, 4H); MS (EI) m/z: 290 [M+H]$^+$. HPLC (Sunfire C18 4.6 mm×50 mm, 10-90% MeCN:10 mM aq. NH$_4$OAc, 2 min gradient) t$_R$=1.34 min, 88% integrated area.

To a solution of 4-(6-amino-pyridin-3-yl)-N-cyclopropyl-benzenesulfonamide (1.04 g, 3.59 mmol) in DCM (12 mL) was added portionwise N-bromosuccinimide (0.64 g, 3.59 mmol). The reaction was stirred for 1 h, then was filtered. The filtrate was washed with sat. aq. Na$_2$S$_2$O$_4$ (20 mL), sat. aq. NaHCO$_3$ (10 mL), then dried over Na$_2$SO$_4$ and concentrated to give 4-(6-amino-5-bromo-pyridin-3-yl)-N-cyclopropyl-benzenesulfonamide (1.07 g, 81% yield). $^1$H NMR (400 MHz, METHANOL-d$_4$) δ ppm 8.30 (d, J=2.01 Hz, 1H), 8.12 (d, J=2.01 Hz, 1H), 7.92 (d, J=8.53 Hz, 2H), 7.76 (d, J=8.53 Hz, 2H), 2.19 (tt, J=6.71, 3.58 Hz, 1H), 0.17-0.83 (m, 4H). MS (EI) m/z: 368, 370 [M+H]$^+$. HPLC (Sunfire C18 4.6 mm×50 mm, 10-90% MeCN:10 mM aq. NH$_4$OAc, 2 min gradient) t$_R$=1.68 min, 90% integrated area.

A mixture of 4-(6-amino-5-bromo-pyridin-3-yl)-N-cyclopropyl-benzenesulfonamide (100 mg, 0.27 mmol), diboron pinacol ester (103 mg, 0.41 mmol), potassium acetate (40 mg, 0.41 mmol), Pd$_2$(dba)$_3$ (8 mg, 0.008 mmol), and PCy$_3$ (5 mg, 0.016 mmol) in 1,4-dioxane (2 mL) was heated at 80° C. to provide 4-[6-amino-5-(4,4,5,5-tetramethyl-[1,3,2]dioxaborolan-2-yl)-pyridin-3-yl]-N-chloropropyl-benzenesulfonamide (112 mg, 100% yield) after purification by preparatory HPLC. This material was combined with 6-chloro nicotinamide (42 mg, 0.27 mmol), Na$_2$CO$_3$ (43 mg, 0.41 mmol), and PdCl$_2$(PPh$_3$)$_4$ (6 mg, 0.008 mmol) in 3:1 acetonitrile:water (2 mL). The reaction mixture was microwave heated at 150° C. for 6 min. At completion, the reaction mixture was concentrated and purified by reverse phase preparatory HPLC to give 2'-amino-5'-(4-(N-cyclopropylsulfamoyl)phenyl)-[2,3'-bipyridine]-5-carboxamide (7 mg, 6% yield). $^1$H NMR (400 MHz, DMSO-d$_6$) δ ppm 9.11 (d, J=1.25 Hz, 1H), 8.53 (d, J=2.26 Hz, 1H), 8.47 (d, J=2.26 Hz, 1H), 8.26-8.39 (m, 2H), 8.21 (br. s., 1H), 8.00 (d, J=8.53 Hz, 3H), 7.91 (d, J=2.51 Hz, 1H), 7.76-7.87 (m, 4H), 7.62 (br. s., 1H), 2.12 (d, J=6.53, 3.51 Hz, 1H), 0.46-0.54 (m, 2H), 0.37-0.45 (m, 2H). MS (EI) m/z: 410 [M+H]$^+$. HPLC (Sunfire C18 4.6 mm×50 mm, 10-90% MeCN:10 mM aq. NH$_4$OAc, 2 min gradient) t$_R$=1.39 min, 96% integrated area.

6.24. Synthesis of 6'-amino-N-cyclopropyl-N-methyl-5'-(1-oxo-1,2,3,4-tetrahydroisoquinolin-6-yl)-[3,3'-bipyridine]-6-sulfonamide

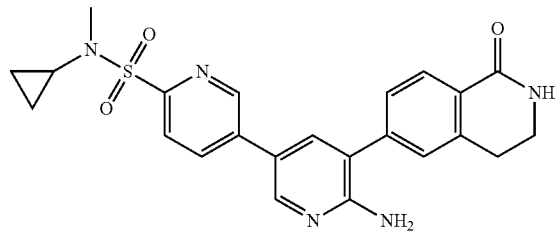 [SMILES: CN(C1CC1)S(=O)(=O)c1ccc(-c2cnc(N)c(-c3ccc4c(c3)CCNC4=O)c2)cn1]

General Method C was applied to 6'-amino-5'-bromo-N-cyclopropyl-[3,3'-bipyridine]-6-sulfonamide (650 mg, 1.76 mmol) and 6'-amino-5'-bromo-N-cyclopropyl-[3,3'-bipyridine]-6-sulfonamide (410 mg, 2.11 mmol) to provide 6'-amino-N-cyclopropyl-N-methyl-5'-(1-oxo-1,2,3,4-tetrahydroisoquinolin-6-yl)-[3,3'-bipyridine]-6-sulfonamide (130 mg, 16% yield) after purification by preparative HPLC. $^1$H NMR (400 MHz, DMSO-$d_6$) δ ppm 9.11 (d, J=1.8 Hz, 1H), 8.51 (d, J=2.3 Hz, 1H), 8.39 (dd, J=8.2, 2.1 Hz, 1H), 7.93 (s, 3H), 7.86 (d, J=2.3 Hz, 1H), 7.46-7.56 (m, 2H), 6.19 (s, 2H), 3.36-3.46 (m, 2H), 2.96 (t, J=6.4 Hz, 2H), 2.88 (s, 3H), 2.23-2.31 (m, 1H), 0.72-0.79 (m, 2H), 0.62-0.69 (m, 2H); MS (EI) m/z=450.5 [M+1]$^+$.

6.25. Synthesis of N-(4-(6-amino-5-(1-oxo-1,2,3,4-tetrahydroisoquinolin-6-yl)pyridin-3-yl)phenyl)ethanesulfonamide

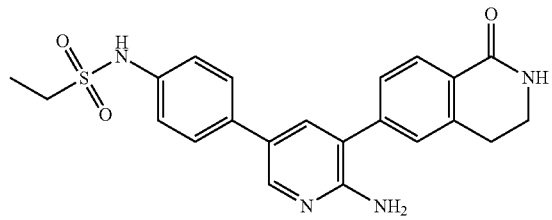 [SMILES: CCS(=O)(=O)Nc1ccc(-c2cnc(N)c(-c3ccc4c(c3)CCNC4=O)c2)cc1]

General method B was applied to 6-(2-amino-5-bromopyridin-3-yl)-3,4-dihydroisoquinolin-1(2H)-one hydrobromide (150 mg, 0.38 mmol) and 4-(ethylsulfonamide)phenylboronic acid (96 mg, 0.42 mmol) to give N-(4-(6-amino-5-(1-oxo-1,2,3,4-tetrahydroisoquinolin-6-yl)pyridin-3-yl)phenyl)ethanesulfonamide (58 mg, 35% yield) after purification by reverse phase preparatory HPLC. $^1$H NMR (400 MHz, DMSO-$d_6$) δ ppm 9.79 (s, 1H), 8.28 (d, J=2.51 Hz, 1H), 7.92 (d, J=8.03 Hz, 2H), 7.58-7.69 (m, 3H), 7.44-7.53 (m, 2H), 7.26 (d, J=8.78 Hz, 2H), 5.96 (br. s., 2H), 3.41 (td, J=6.53, 2.51 Hz, 2H), 3.16 (s, 2H), 3.09 (q, J=7.28 Hz, 2H), 2.96 (t, J=6.40 Hz, 2H), 1.20 (t, J=7.28 Hz, 3H); MS (EI) m/z: 422 [M+H]$^+$. HPLC (Sunfire C18 4.6 mm×50 mm, 10-90% MeOH:10 mM aq. Ammonium formate, 2 min gradient) $t_R$=1.94 min, 97% integrated area.

6.26. Synthesis of 4-(5-amino-6-(1-oxo-1,2,3,4-tetrahydroisoquinolin-6-yl)pyrazin-2-yl)-N-methyl-N-((1R,2R)-2-methylcyclopropyl)benzenesulfonamide The captioned compound was prepared by the method shown below:

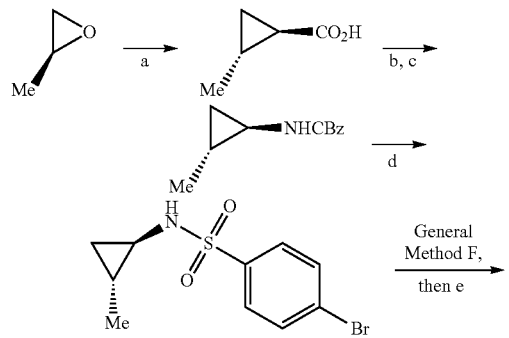

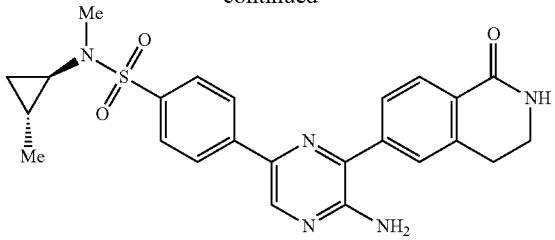

wherein:
a is ethyl 2-(diethoxyphosphoryl)acetate, n-BuLi, MeTHF, 150° C. then aq. NaOH, 100° C.; b is TEA, EtCO$_2$Cl, acetone, then aq NaN$_3$; c is PhMe, 100° C., then benzyl alcohol, CuCl, DMF; d is H$_2$—Pd/C, DCM, then TEA p-bromobenzenesulfonyl chloride; e is Cs$_2$CO$_3$, MeI, DMF.

To a 0° C. solution of ethyl 2-(diethoxyphosphoryl)acetate (16.90 mL, 84.37 mmol) in methyltetrahydrofuran (150 mL) was added n-BuLi (33.0 mL, 82.5 mmol, 2.5 M in hexane). The reaction was maintained at 0° C. for 30 minutes before the addition of (S)-2-methyloxirane. The reaction mixture was then transferred to a teflon lined steel reactor, sealed and heated to 150° C. for 18 h. The reactor was cooled to room temperature, then treated with water:30% aq. NaOH (2:1) and refluxed at 100° C. for 5 h. The biphasic mixture was again cooled to room temperature and transferred to a separatory funnel. The layers were separated and the aqueous phase was acidified with conc. aq. HCl (100 mL) and extracted with isopropyl acetate (3×200 mL) while maintaining the aqueous phase at pH~3. The combined organics were washed with 10% NaCl (2×100 mL), filtered over celite and concentrated to provide (1R,2R)-2-methylcyclopropanecarboxylic acid (7.9 g, 92% yield), which was used directly in the next reaction. $^1$H NMR (400 MHz, CHLOROFORM-d) δ ppm 1.40-1.52 (m, 1H), 1.30-1.39 (m, 1H), 1.20-1.28 (m, 1H), 1.13 (d, J=6.0 Hz, 3H), 0.76 (ddd, J=7.8, 6.5, 4.0 Hz, 1H).

To a 0° C. solution of (1R,2R)-2-methylcyclopropanecarboxylic acid (2.0 g, 20.0 mmol) in anhydrous acetone (100 mL) was added triethylamine (2.87 mL, 20.6 mmol) and ethyl chloroformate (1.96 mL, 20.6 mL). The cold bath was removed and the reaction was allowed to warm to room temperature for 30 min before the addition of sodium azide (1.36 g, 21.00 mmol) in water (20 mL). The reaction was maintained at room temperature for 1 h, then diluted with DCM (300 mL) and water (200 mL). The layers were separated and the organic was washed with water (2×100 mL) and brine (100 mL) then dried over MgSO$_4$ and concentrated to provide (1R,2R)-2-methylcyclopropanecarbonyl azide (1.8 g, 72% yield) which was used directly in the next reaction. $^1$H NMR (400 MHz, CHLOROFORM-d) δ ppm 1.47-1.58 (m, 1H), 1.35-1.42 (m, 1H), 1.28-1.34 (m, 1H), 1.14 (d, J=6.0 Hz, 3H), 0.79-0.87 (m, 1H).

A solution of (1R,2R)-2-methylcyclopropanecarbonyl azide (1.80 g, 14.4 mmol) in toluene (100 mL) was heated to 90° C. for 1 h. After gas evolution had subsided, the solution was cannulated into a flask containing a slurry of benzyl alcohol (4.5 mL, 43.2 mmol) and copper(I) chloride (750 mg, 7.5 mmol) in DMF (100 mL). The reaction was maintained at room temperature for 1 h, then diluted with Et$_2$O (200 mL) then washed with brine, dried over MgSO$_4$ and concentrated. The crude product was purified by flash chromatography over silica gel (20-30% EtOAc/hexane eluent) to provide benzyl ((1R,2R)-2-methylcyclopropyl)-carbamate (1.68 g, 57% yield). $^1$H NMR (400 MHz, CHLOROFORM-d) δ ppm 7.27-7.46 (m, 5 H), 5.11 (br. s., 2H), 4.80-4.99 (m, 1H), 2.28 (d, J=3.0 Hz, 1H), 1.07 (d, J=5.5 Hz, 3H), 0.82-0.97 (m, 1H), 0.67 (ddd, J=9.0, 5.3, 3.8 Hz, 1H), 0.51 (q, J=5.9 Hz, 1H).

A solution of benzyl ((1R,2R)-2-methylcyclopropyl)carbamate (1.68 g, 8.2 mmol) in DCM (55 mL) was charged with 10 wt % Pd/C, then degassed and charged with hydrogen (50 PSI). The reaction was complete after 30 min and so was filtered over celite, rinsing with DCM (15 mL). The liquor was cooled to 0° C., and treated with triethylamine (3.43 mL, 24.6 mmol) and 4-bromobenzene-1-sulfonyl chloride (2.20 g, 8.61 mmol). The cold bath was removed and the reaction was stirred for 1 h. At completion, the reaction was washed with 0.5 M aq. HCl (2×20 mL) and brine (20 mL), dried over MgSO$_4$ and concentrated to provide 4-bromo-N-((1R,2R)-2-methylcyclopropyl)benzenesulfonamide (2.06 g, 87% yield). $^1$H NMR (400 MHz, CHLOROFORM-d) δ ppm 7.74-7.80 (m, 1H), 7.66-7.72 (m, 1H), 4.90 (br. s., 1H), 1.94 (dt, J=3.5, 1.8 Hz, 1H), 1.41 (t, J=7.3 Hz, 1H), 0.89-1.01 (m, 3H), 0.70-0.81 (m, 1H), 0.35-0.45 (m, 1H).

The appropriate procedure specified in general method F was applied to the conversion of 4-bromo-N-((1R,2R)-2-methylcyclopropyl)benzenesulfonamide (2.06 g, 7.1 mmol) to N-((1R,2R)-2-methylcyclopropyl)-4-(4,4,5,5-tetra methyl-1,3,2-dioxaborolan-2-yl)benzenesulfonamide (1.38 g, 58% yield) which was obtained after flash chromatography over silica gel (20-40% EtOAc/hexane eluent). $^1$H NMR (400 MHz, CHLOROFORM-d) δ ppm 7.96 (s, 2H), 7.85-7.92 (m, 2H), 4.75-4.80 (m, 1H), 1.88-1.93 (m, 1H), 1.38 (s, 12H), 1.27 (s, 1H), 0.95 (d, J=1.3 Hz, 3H), 0.70-0.79 (m, 1H), 0.33-0.40 (m, 1H).

The appropriate procedure specified in general method F was applied to the conversion of N-((1R,2R)-2-methylcyclopropyl)-4-(4,4,5,5-tetramethyl-1,3,2-dioxaborolan-2-yl)benzenesulfonamide (676 mg, 1.69 mmol) to 4-(5-amino-6-(1-oxo-1,2,3,4-tetrahydroisoquinolin-6-yl)pyrazin-2-yl)-N-((1R,2R)-2-methylcyclopropyl)benzenesulfonamide hydrochloride after treatment with aq. HCl (350 mg, 45% yield). $^1$H NMR (400 MHz, METHANOL-d$_4$) δ ppm 8.34 (d, J=6.5 Hz, 2H), 8.11-8.16 (m, 1H), 7.97-8.03 (m, 2H), 7.89-7.96 (m, 2H), 7.57-7.61 (m, 1H), 7.54-7.56 (m, 1H), 3.55-3.61 (m, 2H), 3.07-3.14 (m, 2H), 1.84-1.89 (m, 1H), 0.92-0.97 (m, 3H), 0.80-0.89 (m, 1H), 0.64-0.70 (m, 1H), 0.31-0.38 (m, 1H); MS (EI) m/z=450.5 [M+1]$^+$.

To a room temperature slurry of 4-(5-amino-6-(1-oxo-1,2,3,4-tetrahydroisoquinolin-6-yl)pyrazin-2-yl)-N-((1R,2R)-2-methylcyclopropyl)benzenesulfonamide hydrochloride (110 mg, 0.227 mmol) and cesium carbonate (222 mg, 0.681 mmol) was added methyl iodide (16.0 μL, 0.251 mmol). At completion, the reaction was filtered and concentrated, then flashed over silica gel (5-10% MeOH/DCM eluent) to provide 4-(5-amino-6-(1-oxo-1,2,3,4-tetrahydroisoquinolin-6-yl)pyrazin-2-yl)-N-methyl-N-((1R,2R)-2-methylcyclopropyl)-benzenesulfonamide (90 mg, 86% yield). $^1$H NMR (400 MHz, CHLOROFORM-d) δ ppm 8.55 (s, 1H), 8.25 (d, J=7.8 Hz, 1H), 8.16 (d, J=8.5 Hz, 2H), 7.92 (d, J=8.5 Hz, 2H), 7.83 (dd, J=8.0, 1.5 Hz, 1H), 7.70 (s, 1H), 5.95 (br. s, 1H), 5.14 (br. s, 2H), 3.66 (dt, J=7.0, 2.3 Hz, 2H), 3.14 (t, J=7.0 Hz, 2H), 2.76 (s, 3H), 1.48-1.53 (m, 1H), 1.27-1.35 (m, 1H), 1.06 (d, J=6.3 Hz, 3H), 0.96-1.02 (m, 1H), 0.47 (dd, J=12.3, 6.0 Hz, 1H); MS (EI) m/z=464.5 [M+1]$^+$.

6.27. Synthesis of 4-(5-amino-6-(1-oxo-1,2,3,4-tetrahydroisoquinolin-6-yl)pyrazin-2-yl)-N-ethyl-N,2-dimethylbenzenesulfonamide The captioned compound was prepared by the method shown below:

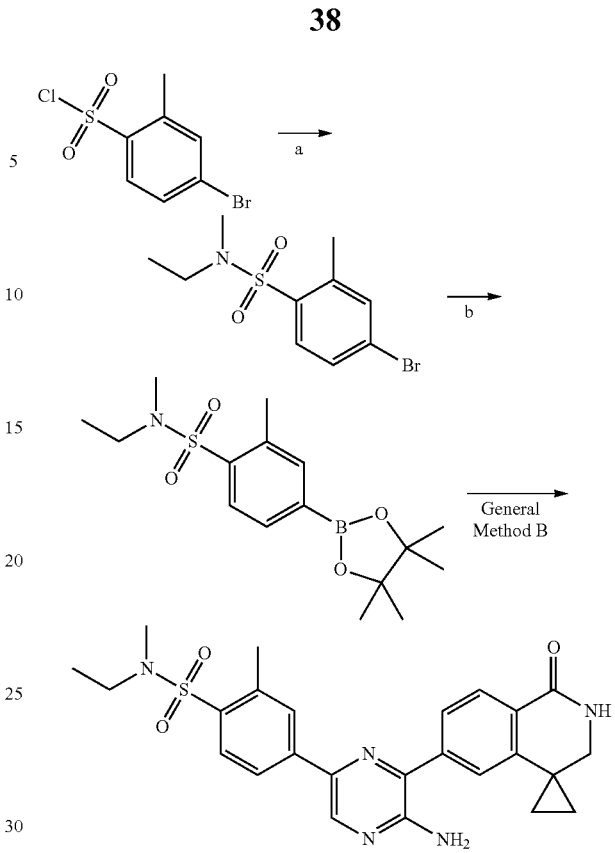

wherein:
a is N-methylethylamine, CH$_2$Cl$_2$, 20° C., 2 h; b is PdCl$_2$(dppf)-CH$_2$Cl$_2$, (BPin)$_2$, 85° C., 2 h.

To a 0° C. solution of 4-bromo-2-methylbenzenesulfonyl chloride (1.00 g, 3.71 mmol) in CH$_2$Cl$_2$ (10 mL) was added N-ethyldiisopropylamine (0.71 mL, 4.31 mmol) and N-methylethylamine (0.96 mL, 11.13 mmol). The cold bath was removed and the reaction was stirred for 2 h. At completion, the reaction was concentrated, and the crude material was dissolved in CH$_2$Cl$_2$ (20 mL). The mixture was washed with 0.5 N aqueous HCl (3×10 mL), sat. aq. NaHCO$_3$ (2×10 mL), water (10 mL), and saturated aqueous NaCl (5 mL), dried (Na$_2$SO$_4$), and concentrated to give 4-bromo-N-ethyl-2,N-dimethyl-benzenesulfonamide (0.91 g, 3.11 mmol, 85% yield). This material was directly dissolved in 1,4-dioxane (10 mL) and treated with bisboron pinacol ester (0.87 g, 3.43 mmol), PdCl$_2$(dppf)-DCM (69 mg, 0.093 mmol), and KOAc (0.92 g, 9.34 mmol). The reaction was heated at 85° C. for 2 h. At completion, the reaction was cooled to room temperature and concentrated. The crude material was treated with CH$_2$Cl$_2$ (30 mL) and water (10 mL). The organic layer was washed with water (2×10 mL) and brine (5 mL), dried over Na$_2$SO$_4$ and concentrated. The crude material was purified by flash chromatography over silica gel (5-20% EtOAc:hexane eluent) to give N-ethyl-2,N-dimethyl-4-(4,4,5,5-tetramethyl-[1,3,2]dioxaborolan-2-yl)-benzenesulfonamide (0.64 g, 60% yield). $^1$H NMR (300 MHz, MeOH) δ ppm 7.80-7.88 (m, 1H), 7.68-7.77 (m, 2H), 3.26 (q, J=7.12 Hz, 2H), 2.83 (s, 3H), 2.61 (s, 3H), 1.37 (s, 12H), 1.17 (t, J=7.15 Hz, 3H). MS (EI) m/z: 340 [M+H]$^+$. HPLC (Sunfire C18 4.6 mm×50 mm, 10-90% MeCN:10 mM aq NH$_4$OAc, 2 min gradient) t$_R$=2.48 min, 91% integrated area.

A solution of N-ethyl-2,N-dimethyl-4-(4,4,5,5-tetramethyl-[1,3,2]dioxaborolan-2-yl)-benzenesulfonamide (140 mg, 0.42 mmol), 6-(3-amino-6-bromopyrazin-2-yl)-3,4-dihydroisoquinolin-1(2H)-one (150 mg, 0.38 mmol) Pd(PPh₃)₄ (13.2 mg, 0.011 mmol) and 2.0 M aq. Na₂CO₃ (0.38 mL) in n-butanol (2 mL) was microwave heated at 150° C. for 10 min to provide 4-(5-amino-6-(1-oxo-1,2,3,4-tetrahydroisoquinolin-6-yl)pyrazin-2-yl)-N-ethyl-N,2-dimethylbenzenesulfonamide (49 mg, 29% yield) after purification by reverse phase preparatory HPLC. ¹H NMR (400 MHz, DMSO-d₆) δ ppm 8.69 (s, 1H), 8.04 (s, 1H), 7.93-8.02 (m, 3H), 7.82 (d, J=8.28 Hz, 1H), 7.67-7.77 (m, 2H), 6.62 (s, 2H), 3.43 (td, J=6.40, 2.51 Hz, 2H), 3.18 (q, J=6.94 Hz, 3H), 3.00 (t, J=6.53 Hz, 2H), 2.76 (s, 3H), 2.59 (s, 3H), 1.08 (t, J=7.15 Hz, 3H). MS (EI) m/z: 452 [M+H]⁺. HPLC (Sunfire C18 4.6 mm×50 mm, 10-90% MeCN:10 mM aq NH₄OAc, 4 min gradient) $t_R$=2.14 min, 100% integrated area.

6.28. Synthesis of 4-(5-amino-6-(1-oxo-1,2,3,4-tetrahydroisoquinolin-6-yl)pyrazin-2-yl)-N-cyclopropyl-N-methylbenzenesulfonamide

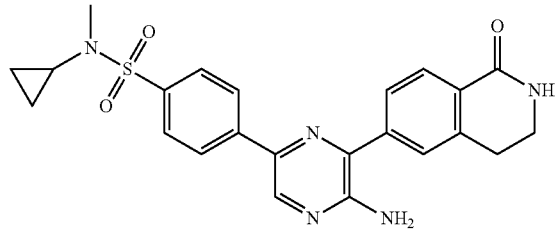 [SMILES: CN(C1CC1)S(=O)(=O)c1ccc(-c2cnc(N)c(-c3ccc4c(c3)CCNC4=O)n2)cc1]

General method C was applied to 4-(5-amino-6-bromopyrazin-2-yl)-N-cyclopropyl-N-methylbenzenesulfonamide (383 mg, 1.00 mmol) and 6-(4,4,5,5-tetramethyl-1,3,2-dioxaborolan-2-yl)-3,4-dihydroisoquinolin-1(2H)-one (300 mg, 1.1 mmol) to provide 4-(5-amino-6-(1-oxo-1,2,3,4-tetrahydroisoquinolin-6-yl)pyrazin-2-yl)-N-cyclopropyl-N-methylbenzenesulfonamide (382 mg, 85% yield) after purification by preparatory HPLC. ¹H NMR (400 MHz, DMSO-d₆) δ ppm 8.73 (s, 1H), 8.26 (d, J=8.5 Hz, 2H), 8.03 (br. s., 1H), 7.97 (d, J=8.0 Hz, 1H), 7.84 (d, J=8.5 Hz, 2H), 7.74 (d, J=8.0 Hz, 1H), 7.70 (s, 1H), 3.42 (t, J=5.3 Hz, 2H), 2.99 (t, J=6.4 Hz, 2H), 2.67 (s, 3H), 1.77-1.86 (m, 1H), 0.61-0.81 (m, 4 H); MS (EI) m/z=450.5 [M+1]⁺.

6.29. Synthesis of 2-(4-(5-amino-6-(1-oxo-1,2,3,4-tetrahydroisoquinolin-6-yl)pyrazin-2-yl)phenyl)-2-methylpropanenitrile

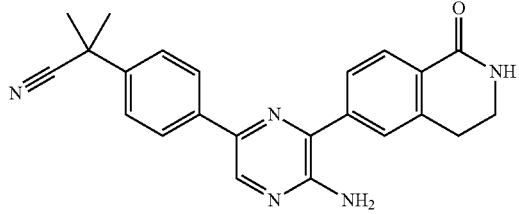 [SMILES: CC(C)(C#N)c1ccc(-c2cnc(N)c(-c3ccc4c(c3)CCNC4=O)n2)cc1]

General method B was applied to 4-(2-cyanopropan-2-yl)phenylboronic acid (79 mg, 0.42 mmol) and 6-(3-amino-6-bromopyrazin-2-yl)-3,4-dihydroisoquinolin-1(2H)-one (150 mg, 0.38 mmol) in n-butanol (2 mL) to give 2-{4-[5-amino-6-(1-oxo-1,2,3,4-tetrahydro-isoquinolin-6-yl)-pyrazin-2-yl]-phenyl}-2-methyl-propionitrile (119 mg, 82% yield) after purification by column chromatography on silica (2-5% MeOH/DCM eluent).

¹H NMR (400 MHz, DMSO-d₆) δ ppm 8.59 (s, 1H), 8.02 (d, J=8.53 Hz, 2H), 7.96 (d, J=8.03 Hz, 2H), 7.75 (dd, J=8.03, 1.25 Hz, 1H), 7.70 (s, 1H), 7.58 (d, J=8.53 Hz, 2H), 6.45 (s, 2H), 3.43 (td, J=6.40, 2.51 Hz, 2H), 2.99 (t, J=6.40 Hz, 2H), 1.71 (s, 6H). MS (EI) m/z: 384 [m+H]⁺. HPLC (Shim-Pack VP ODS 4.6 mm×50 mm, 10-90% 95% MeOH, 5% water with 0.1% TFA, 4 min gradient) $t_R$=3.22 min, 99% integrated area.

6.30. General Method G and Synthesis of 4-(5-amino-6-(1-oxo-2,3,4,5-tetrahydro-1H-benzo[c]azepin-7-yl)pyrazin-2-yl)-N-ethyl-N-methylbenzenesulfonamide The captioned compound was prepared by general method G, represented below:

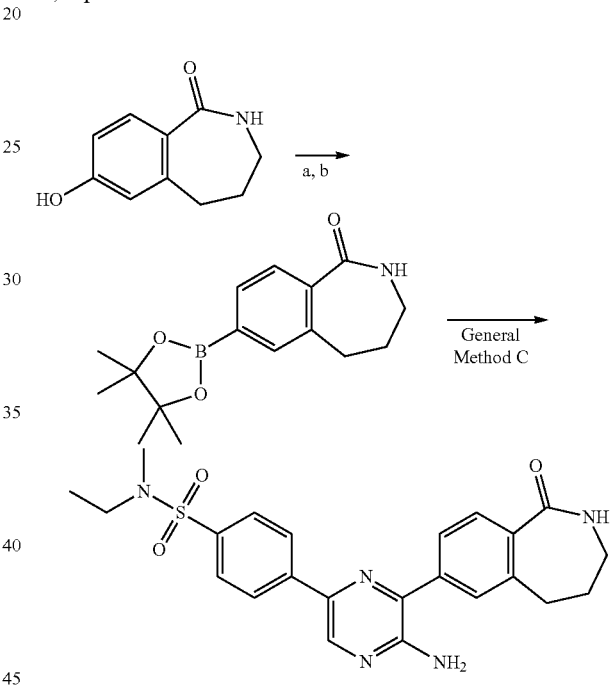

wherein:
a is NaH, (TfO)₂NPh, THF; and b is diboron pinacol ester, Pd(dppf)Cl₂, KOAc, dioxane, 90° C.

To a room temperature solution of 7-hydroxy-2,3,4,5-tetrahydro-1H-benzo[c]azepin-1-one (2.3 g, 12.9 mmol) in THF (100 mL) was added NaH (671 mg, 16.7 mmol), followed by 1,1,1-trifluoro-N-phenyl-N-((trifluoromethyl)sulfonyl)methanesulfonamide (5.98 g, 16.77 mmol). The reaction was stirred at room temperature for 2 h, then quenched with sat. aq. NH₄Cl and extracted with EtOAc (3×50 mL). The combined organics were washed with brine, dried over Na₂SO₄ and concentrated. The crude material was purified by flash chromatography over silica gel (20% EtOAc/hexane eluent) to provide 1-oxo-2,3,4,5-tetrahydro-1H-benzo[c]azepin-7-yl trifluoromethanesulfonate (12.9 mmol, 77% yield) MS (EI) m/z=310 [M+1]⁺.

A degassed slurry of 1-oxo-2,3,4,5-tetrahydro-1H-benzo[c]azepin-7-yl trifluoromethanesulfonate (4.0 g, 12.9 mmol) diboron pinacol ester (9.9 g, 39.0 mmol), KOAc (1.9 g, 19.5 mmol), and Pd(dppf)Cl₂ (963 mg, 1.3 mmol) in dioxane (8 mL) was heated to 90° C. for 1.5 h. At completion, the reaction was filtered and concentrated, then purified by flash chromatography over silica gel (30% EtOAc/hexanes eluent) to provide 7-(4,4,5,5-tetramethyl-1,3,2-dioxaborolan-2-yl)-2,3,4,5-tetrahydro-1H-benzo[c]azepin-1-one (1.5 g, 41% yield). MS (EI) m/z=288 [M+1]⁺.

General method C was applied to 7-(4,4,5,5-tetramethyl-1,3,2-dioxaborolan-2-yl)-2,3,4,5-tetrahydro-1H-benzo[c]azepin-1-one (95 mg, 0.33 mmol) and 4-(5-amino-6-bromopyrazin-2-yl)-N-ethyl-N-methylbenzenesulfonamide (108 mg, 0.29 mmol) to provide 4-(5-amino-6-(1-oxo-2,3,4,5-tetrahydro-1H-benzo[c]azepin-7-yl)pyrazin-2-yl)-N-ethyl-N-methylbenzenesulfonamide (33 mg, 22% yield) after purification by preparatory HPLC. $^1$H NMR (400 MHz, DMSO-$d_6$) δ ppm 8.70 (s, 1H), 8.22 (d, J=8.5 Hz, 2H), 8.12 (t, J=5.8 Hz, 1H), 7.80 (d, J=8.5 Hz, 2H), 7.71 (dd, J=8.0, 1.5 Hz, 1H), 7.62-7.66 (m, 2H), 6.66 (br. s, 2 H), 2.93-3.09 (m, 4H), 2.83 (t, J=1.0 Hz, 2H), 2.67 (s, 3H), 1.94 (dd, J=12.3, 6.0 Hz, 2H), 1.03 (t, J=7.2 Hz, 3H); MS (EI) m/z=452.5 [M+1]⁺.

6.31. Synthesis of 6-(3-amino-6-(4-(1-cyclopropylethoxy)phenyl)pyrazin-2-yl)-3,4-dihydroisoquinolin-1(2H)-one The captioned compound was prepared by the method shown below:

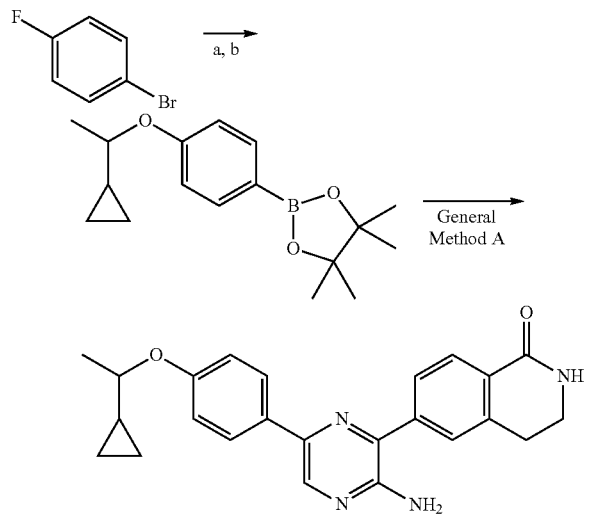

wherein:
a is NaH, 1-cyclopropylethanol, DMF, 100° C.; b is Pd(dppf)Cl$_2$, (BPin)$_2$, KOAc, 90° C., 2 hours.

To a 0° C. slurry of NaH (460 mg, 11.4 mmol, 60 wt % dispersion in mineral oil) in DMF (14 mL) was added 1-cyclopropylethanol (0.79 mL, 7.41 mmol) dropwise. The cold bath was removed for 30 min before the addition of 1-bromo-4-fluorobenzene (1.00 g, 5.7 mmol). The resulting reaction mixture was heated to 100° C. for 3 h. At completion, the reaction was cooled to room temperature and concentrated. The resulting oil was diluted with water (30 mL) and extracted into EtOAc (3×30 mL). The combined organics were washed with brine (20 mL), then dried over MgSO$_4$ and concentrated to provide 1-bromo-4-(1-cyclopropylethoxy)benzene (1.30 g, 95% yield). The resulting oil was used directly without further purification.

A slurry of 1-bromo-4-(1-cyclopropylethoxy)benzene (1.30 g, 5.39 mmol), 4,4,4',4',5,5,5',5'-octamethyl-2,2'-bi(1,3,2-dioxaborolane) (1.77 g, 7.01 mmol), PdCl$_2$dppf-DCM (197 mg, 0.27 mmol), KOAc (1.06 g, 10.78 mmol) in DMF (12 mL) was heated to 100° C. for 2 h. At completion, the reaction was concentrated, then purified by flash chromatography over silica gel (20-40% EtOAc/hexane eluent) to provide 2-(4-(1-cyclopropylethoxy)phenyl)-4,4,5,5-tetramethyl-1,3,2-dioxaborolane (1.38 g, 88% yield).

General method A was applied to 2-(4-(1-cyclopropylethoxy)phenyl)-4,4,5,5-tetramethyl-1,3,2-dioxaborolane (639 mg, 2.00 mmol), providing 6-(3-amino-6-(4-(1-cyclopropylethoxy)phenyl)pyrazin-2-yl)-3,4-dihydroisoquinolin-1(2H)-one (321 mg, 40% yield) after purification by reverse phase preparatory HPLC. $^1$H NMR (400 MHz, DMSO-$d_6$) δ ppm 8.50 (s, 1H), 8.00 (br. s., 1H), 7.95 (d, J=8.0 Hz, 1H), 7.88 (d, J=8.8 Hz, 2H), 7.72-7.77 (m, 1H), 7.70 (s, 1H), 6.97 (d, J=8.8 Hz, 2H), 6.30 (s, 2H), 3.94-4.04 (m, 1H), 3.42 (td, J=6.4, 2.5 Hz, 2H), 2.99 (t, J=6.5 Hz, 2H), 1.29 (d, J=6.0 Hz, 3H), 1.09 (dt, J=8.0, 4.9 Hz, 1H), 0.43-0.53 (m, 2H), 0.25-0.39 (m, 2H); MS (EI) m/z=401.5 [M+1]⁺.

6.32. Synthesis of 6-(2-amino-5-(4-(2-(dimethylamino)propan-2-yl)phenyl)pyridin-3-yl)-3,4-dihydroisoquinolin-1(2H)-one The captioned compound was prepared by the method shown below:

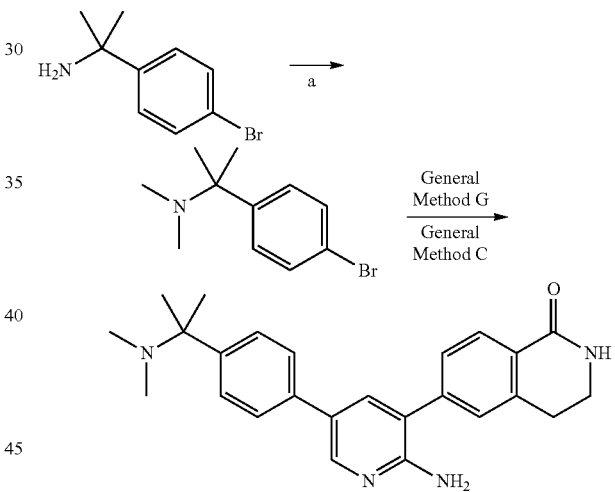

To a solution of 2-(4-bromophenyl)propan-2-amine (500 mg, 2.34 mmol) in DCM (30 mL) was added 37% aqueous formaldehyde (525 μL, 7.0 mmol), Na$_2$SO$_4$ (100 mg) and STAB (2.98 g, 14.0 mmol). After stirring 2 h at room temperature, the reaction was partitioned between sat. aq. NaHCO$_3$ (20 mL) and DCM (20 mL). The layers were separated and the aqueous layer was extracted with DCM (2×30 mL). The combined organics were dried over Na$_2$SO$_4$, filtered and concentrated to provide 2-(4-bromophenyl)-N,N-dimethylpropan-2-amine (464 mg, 82% yield) as a yellow oil. $^1$H NMR (400 MHz, METHANOL-$d_4$) δ ppm 7.45 (d, J=6.0 Hz, 4H), 2.16 (s, 6H), 1.40 (s, 6H); MS (EI) m/z=243.2 [M+1]⁺.

General method G was applied to 2-(4-bromophenyl)-N,N-dimethylpropan-2-amine (450 mg, 1.86 mmol), to provide N,N-dimethyl-2-(4-(4,4,5,5-tetramethyl-1,3,2-dioxaborolan-2-yl)phenyl)propan-2-amine (300 mg, 56% yield) after purification by flash chromatography over silica gel (50-100% EtOAc/hexanes). MS (EI) m/z=290.2 [M+1]⁺.

General Method C was applied to N,N-dimethyl-2-(4-(4,4,5,5-tetramethyl-1,3,2-dioxaborolan-2-yl)phenyl)propan-2-amine (109 mg, 0.38 mmol) and 6-(2-amino-5-bromopyridin-3-yl)-3,4-dihydroisoquinolin-1(2H)-one hydrobromide (125 mg, 0.31 mmol) to afford 6-(2-amino-5-(4-(2-(dimethylamino)propan-2-yl)phenyl)pyridin-3-yl)-3,4-dihydroisoquinolin-1(2H)-one (14 mg, 11% yield) as a white solid after purification by flash chromatography. $^1$H NMR (300 MHz, DMSO-$d_6$) δ ppm 8.32 (s, 1H), 7.81-8.11 (m, 2H), 7.37-7.79 (m, 7H), 5.87 (s, 2H), 3.41 (m, 2H), 2.85-3.10 (m, 2H), 2.11 (s, 6H), 1.30 (s, 6 H); MS (EI) m/z=401.5 [M+1]$^+$.

6.33. Synthesis of 4-(5-amino-6-(5-oxo-2,3,4,5-tetrahydrobenzo[f][1,4]oxazepin-8-yl)pyrazin-2-yl)-N-cyclopropyl-N-methylbenzenesulfonamide The captioned compound was prepared by the method shown below:

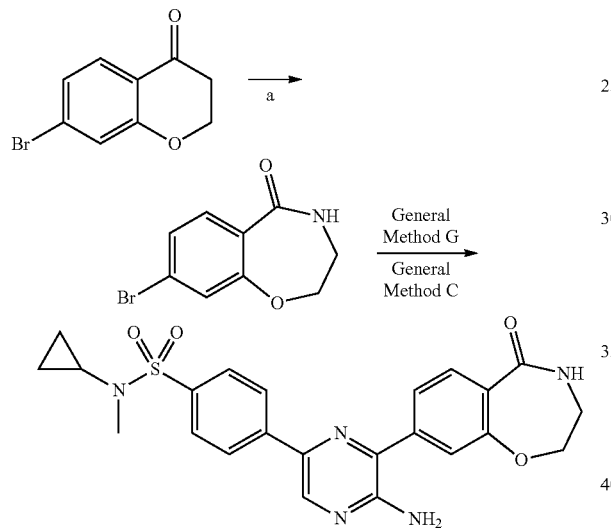

A solution of 7-bromochroman-4-one (340 mg, 1.5 mmol) and methanesulfonic acid (3 mL, 23.0 mmol) in DCM was cooled to 0° C. and treated with NaN$_3$ (146 mg, 2.25 mmol) portionwise, while maintaining the internal temperature below 5° C. The reaction was then stirred at 0° C. for 4 h. At completion, the reaction was slowly neutralized with 8 N aq. NaOH, then diluted with DCM (20 mL) and water (20 mL). The layers were separated and the organics were dried over MgSO$_4$, filtered and evaporated to afford 8-bromo-3,4-dihydrobenzo[f][1,4]oxazepin-5(2H)-one (370 mg, 100% yield). MS (EI) m/z=242.1 [M+1]$^+$.

General methods G and C were successively applied to 8-bromo-3,4-dihydrobenzo[f][1,4]oxazepin-5(2H)-one (370 mg, 1.5 mmol) to provide 4-(5-amino-6-bromopyrazin-2-yl)-N-cyclopropyl-N-methylbenzenesulfonamide (241 mg, 41% yield, 2 steps) after purification of the crude reaction mixture over silica gel (2-10% MeOH/DCM eluent). $^1$H NMR (400 MHz, DMSO-$d_6$) δ ppm 8.72 (s, 1H), 8.43 (dd, J=10.3, 4.8 Hz, 1H), 8.26 (d, J=8.8 Hz, 2H), 7.90 (d, J=8.0 Hz, 1H), 7.85 (d, J=8.3 Hz, 2H), 7.54 (dd, J=8.0, 1.8 Hz, 1H), 7.41 (d, J=1.5 Hz, 1H), 4.31-4.40 (m, 2H), 3.56 (s, 3H), 3.33-3.43 (m, 1H), 2.47-2.52 (m, 2 H), 0.65-0.79 (m, 4H); MS (EI) m/z=466.5 [M+1]$^+$.

6.34. Synthesis of 4-(5-amino-6-(1-oxo-3-hydro-4,4-dideutero-isoquinolin-6-yl)pyrazin-2-yl)-N-cyclopropyl-N-Trideuteromethylbenzenesulfonamide The captioned compound was prepared by the method shown below:

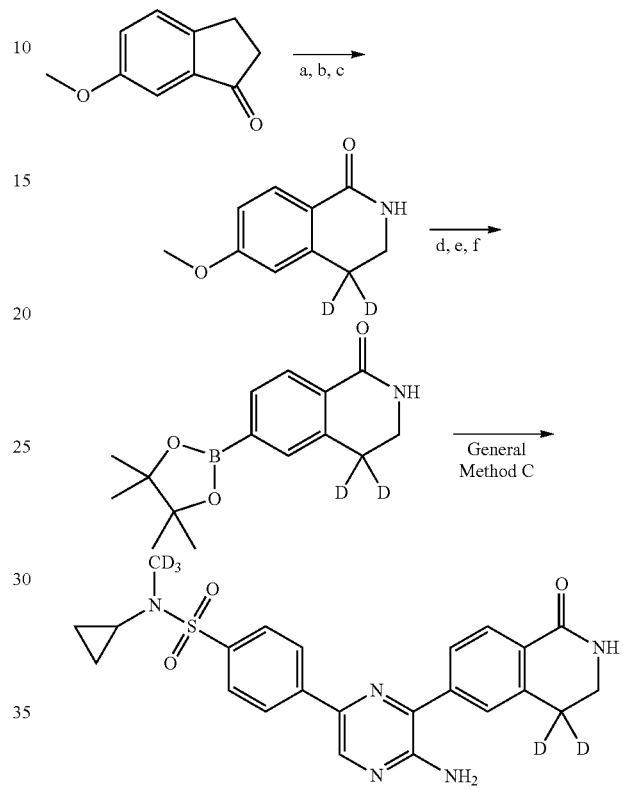

wherein:
a is LiAlD$_4$, AlCl$_3$, MeOH; b is CrO$_3$, HOAc, H$_2$O; c is NaN$_3$,MeSO$_3$H, DCM; d is BBr$_3$, DCM; e is PhNTf2, NaH, THF; and f is Pd(dppf)Cl$_2$, (Bpin)$_2$, KOAc, dioxane.

AlCl$_3$ (4.9 g, 36.7 mmol) and LiAlD$_4$ (770 mg, 18.4 mmol) were suspended in anhydrous Et$_2$O (50 mL) and cooled to 0° C. 6-methoxy-2,3-dihydro-1H-inden-1-one (744 mg, 4.59 mmol) was added slowly to the stirred slurry. The reaction was removed from the cold bath and stirred overnight while gradually warming to room temperature. At completion, the reaction was quenched sequentially by addition of water (5.6 mL), 15% aq. KOH (5.6 mL), and water (16.8 mL). Na$_2$SO$_4$ was added and the mixture was filtered. The organics were concentrated then purified by flash chromatography over silica gel (30% EtOAc/hexanes eluent) to provide 5-methoxy-3,3-dideutero-2-hydro-1H-indene as a clear oil (500 mg, 73% yield) $^1$H NMR (400 MHz, CHLOROFORM-d) δ ppm 7.38 (dd, J=9.00 Hz, 1H), 7.18-7.22 (m, 2H), 3.85 (s, 3H), 3.06-3.11 (m, 2H), 2.71-2.75 (m, 2H).

5-methoxy-3,3-dideutero-2-hydro-1H-indene (500 mg, 3.33 mmol) was dissolved in acetic acid (10 mL) and a solution of CrO$_3$ (1.33 g, 13.32 mmol) in 50% aq. acetic acid (10 mL) was slowly added. The reaction was stirred at 50° C. for 0.5 h, then cooled to 0° C. and quenched with isopropanol (3 mL). The reaction mixture was partitioned between 0.25 N aq. NaOH (50 mL) and EtOAc (50 mL). The layers were separated and the organics were washed with brine, dried over MgSO$_4$ and concentrated to afford 5-methoxy-3,3-dideutero- 2-dihydro-inden-1-one (545 mg, 100% yield). ¹H NMR (400 MHz, CHLOROFORM-d) δ ppm 7.70 (br. s., 1 H), 6.91 (br. s., 2H), 3.89 (br. s., 3H), 2.67 (br. s., 2H); MS (EI) m/z=165.4 [M+1]⁺.

Methanesulfonic acid (1.0 mL, 15.4 mmol) was added to a solution of 5-methoxy-3,3-dideutero-2-dihydro-inden-1-one (600 mg, 3.65 mmol) in DCM (40 mL), and the solution cooled to 0° C. Sodium azide (356 mg, 5.48 mmol) was slowly added portion-wise to the stirred solution. After 6 h at 0° C. the reaction was quenched with 8N aq. NaOH (20 mL). The layers were separated, and the aqueous layer was extracted with DCM (3×20 mL). The combined organics were washed with brine (30 mL), dried over Na₂SO₄ and concentrated to afford 6-methoxy-4,4-dideutero-3-hydroisoquinolin-1(2H)-one (500 mg, 76% yield). ¹H NMR (400 MHz, CHLOROFORM-d) δ ppm 7.99 (d, J=8.78 Hz, 1H), 6.88 (dd, J=8.78, 2.51 Hz, 1H), 6.74 (d, J=2.51 Hz, 1H), 3.88 (s, 3H), 3.60 (s, 2H); MS (EI) m/z=180.4 [M+1]⁺.

To a −78° C. solution of 6-methoxy-4,4-dideutero-3-hydroisoquinolin-1(2H)-one (2.9 g, 16.2 mmol) in DCM (150 mL) was added a freshly prepared 1.0 M solution of BBr₃ in DCM (32.4 mL, 32.4 mmol). The reaction was allowed to gradually warm to room temperature overnight. At completion, the reaction was cooled to 0° C. and carefully quenched with MeOH (10 mL) then concentrated and purified by flash chromatography over silica gel (10% MeOH/DCM eluent) to provide 6-hydroxy-4,4-dideutero-3-hydroisoquinolin-1 (2H)-one as a bright orange solid (2.33 g, 86% yield). ¹H NMR (400 MHz, DMSO-d₆) δ ppm 7.66 (d, J=8.53 Hz, 1H), 7.60 (br. s., 1H), 6.68 (dd, J=8.53, 2.51 Hz, 1H), 6.61 (d, J=2.26 Hz, 1H); MS (EI) m/z=166.4 [M+1]⁺.

A solution room temperature of 6-hydroxy-4,4-dideutero-3-hydroisoquinolin-1(2H)-one (2.75 g, 16.2 mmol) in THF (150 mL) was treated with NaH (1.62 g of 60 wt. % dispersion in mineral oil, 40.5 mmol). The reaction was stirred for 0.5 h, then treated with PhNTf2 (17.36 g, 48.6 mmol) and the reaction was maintained at room temperature for 2 h. At completion, the reaction was quenched with sat. aq. NH₄Cl (50 mL), then diluted with water (50 mL) and extracted with EtOAc (3×100 mL). The combined organics were washed with brine (100 mL), then dried over Na₂SO₄ and concentrated. The crude material was purified by flash chromatography over silica gel (2-10% MeOH/DCM eluent to provide 1-oxo-3-hydro-4,4-dideutero-isoquinolin-6-yl trifluoromethanesulfonate (3.31 g, 69% yield) as a slightly red solid. ¹H NMR (400 MHz, DMSO-d₆) δ ppm 8.14 (br. s., 1H), 7.99 (d, J=8.53 Hz, 1H), 7.52 (d, J=2.51 Hz, 1H), 7.45 (dd, J=8.66, 2.64 Hz, 1H), 3.38 (d, J=2.76 Hz, 2H); MS (EI) m/z=298.2[M+1]⁺.

A slurry of 1-oxo-3-hydro-4,4-dideutero-isoquinolin-6-yl trifluoromethanesulfonate (3.30 g, 11.1 mmol) diboron pinacol ester (8.45 g, 33.3 mmol), KOAc (1.63 g, 16.7 mmol) and Pd(dppf)Cl₂ (814 mg, 1.1 mmol) in dioxane (50 mL) was degassed then heated to 90° C. for 1.5 h. At completion, the reaction was filtered and concentrated, then purified by flash chromatography over silica gel (30% EtOAc/hexanes eluent) to provide 6-(4,4,5,5-tetramethyl-1,3,2-dioxaborolan-2-yl)-3-hydro-4,4-dideutero-isoquinolin-1(2H)-one (2.2 g, 72% yield). ¹H NMR (400 MHz, DMSO-d₆) δ ppm 7.99 (br. s, 1H), 7.80 (dd, J=1.00 Hz, 1H), 7.61 (dd, J=7.78, 5.77 Hz, 2H), 7.59 (dd, J=14.00 Hz, 2H), 3.34 (d, J=2.26 Hz, 2H), 1.29 (s, 12 H); MS (EI) m/z=276.4 [M+1]⁺. Method C was applied to 6-(4,4,5,5-tetramethyl-1,3,2-dioxaborolan-2-yl)-3-hydro-4,4-dideutero-isoquinolin-1(2H)-one (1.14 g, 4.15 mmol) and 3,5-dibromopyrazin-2-amine (1.0 g, 3.95 mmol). At completion, the crude reaction mixture was filtered then purified by flash chromatography over silica gel (5-10% MeOH/DCM eluent) to provide 4-(5-amino-6-(1-oxo-3-hydro-4,4-dideutero-isoquinolin-6-yl)pyrazin-2-yl)-N-cyclopropyl-N-Trideuteromethylbenzenesulfonamide (435 mg, 23% yield). ¹H NMR (400 MHz, DMSO-d₆) δ ppm 8.72 (s, 1H), 8.26 (d, J=8.53 Hz, 2H), 8.02 (br. s., 1H), 7.97 (d, J=8.03 Hz, 1H), 7.84 (d, J=8.53 Hz, 2H), 7.74 (dd, J=8.03, 1.76 Hz, 1H), 7.70 (d, J=1.51 Hz, 1H), 3.41 (d, J=2.51 Hz, 2H), 1.78-1.86 (m, 1H), 0.72-0.79 (m, 2H), 0.64-0.72 (m, 2H); MS (EI) m/z=455.1[M+1]⁺.

6.35. Synthesis of 4-(6-amino-5-(4,4-dimethyl-1-oxo-1,2,3,4-tetrahydroisoquinolin-6-yl)pyridin-3-yl)-N-cyclopropylbenzenesulfonamide The captioned compound was prepared by the method shown below:

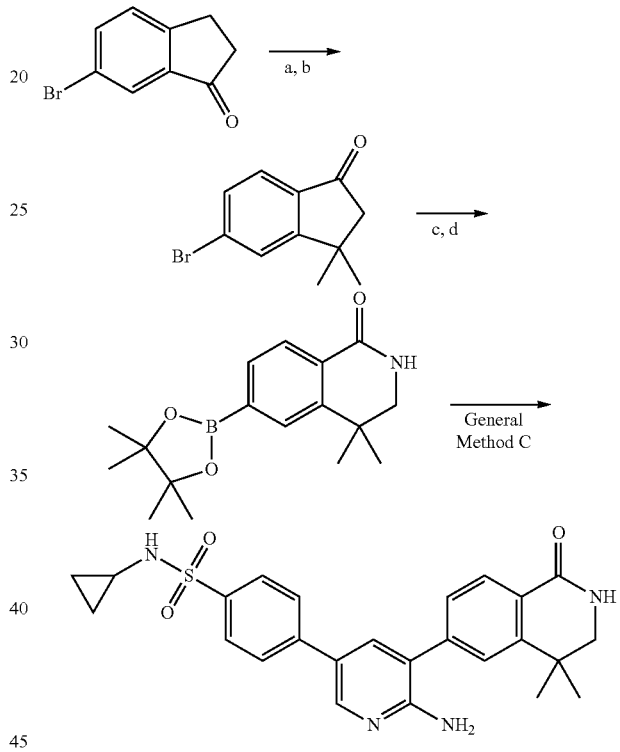

wherein:
a is TiCl₄, ZnMe₂, DCM; b is CrO₃, HOAc; c is NaN₃, MsOH, DCM; d is (Bpin)₂, Pd(dppf)Cl₂, KOAc, dioxane.

A 1.0 M solution of TiCl₄ in DCM (50 mL, 49.8 mmol) was added to a reaction vessel containing DCM (40 mL) cooled to −40° C. Then, a 2.0 M solution of dimethyl zinc in toluene (35.5 ml, 71.1 mmol) was added slowly and the solution was stirred for 20 minutes at −40° C. To this mixture was added a solution of 6-bromo-2,3-dihydro-1H-inden-1-one (5.0 g, 23.7 mmol) in DCM (40 ml) and the reaction was allowed to warm gradually to room temperature overnight. At completion, the reaction was cooled to 0° C. and quenched with MeOH (10 mL), then diluted with water (50 mL) and DCM (50 mL). The layers were separated and the organic layer was washed with brine (50 mL), dried over Na₂SO₄, filtered and concentrated. 6-bromo-1,1-dimethyl-2,3-dihydro-1H-indene (4.14 g, 78% yield) was isolated as a clear oil after purification by flash chromatography over silica gel (hexane eluent). ¹H NMR (400 MHz, CHLOROFORM-d) δ ppm 7.22-7.33 (m, 2H), 7.07 (d, J=8.5 Hz, 1H), 2.86 (t, J=7.3 Hz, 2H), 1.95 (t, J=7.3 Hz, 2H), 1.28 (s, 6H); MS (EI) m/z=226.2 [M+1]⁺.

To a solution of 6-bromo-1,1-dimethyl-2,3-dihydro-1H-indene (3.6 g, 16 mmol) in acetic acid (50 mL) was added to a solution of CrO₃ (9.6 g, 96.0 mmol) in 50% aqueous acetic acid (50 mL). This solution was heated for 3 h at 60° C. At completion, the reaction mixture was quenched by the addition of isopropanol (20 mL). The quenched reaction was partitioned between EtOAc (200 mL) and a 0.25 M aqueous NaOH (100 mL). The layers were separated and the organics were extracted with EtOAc (2×100 mL). The combined organics were washed with brine, dried over Na₂SO₄, filtered and concentrated. After purification by flash chromatography over silica gel (50% EtOAc/hexanes eluent), 5-bromo-3,3-dimethyl-2,3-dihydro-1H-inden-1-one (2.91 g, 76% yield) was isolated as a white solid. ¹H NMR (400 MHz, CHLOROFORM-d) δ ppm 7.65 (s, 1H), 7.47-7.58 (m, 2H), 2.58 (s, 2H), 1.42 (s, 6H); MS (EI) m/z=240.1 [M+1]⁺.

5-bromo-3,3-dimethyl-2,3-dihydro-1H-inden-1-one (1.6 g, 6.7 mmol) was dissolved in DCM (12 mL) and cooled to 0° C. Then MeSO₃H (1.83 ml, 28.1 mmol) was added, followed by the portion-wise addition of NaN₃ (653 mg, 10.1 mmol) over ~10 min, while maintaining the internal reaction temperature below 5° C. The reaction was allowed to warm to room temperature and was stirred 3 h under nitrogen. At completion, the reaction was cooled to 0° C. and quenched with 8 M aq. NaOH. After stirring 30 minutes at room temperature, the quenched reaction was partitioned between DCM (50 mL) and water (50 mL). The layers were separated and the aqueous layer was extracted with DCM (2×30 mL). The combined organics were washed with brine (50 mL), dried over Na₂SO₄, filtered and concentrated. 6-bromo-4,4-dimethyl-3,4-dihydroisoquinolin-1(2H)-one (711 mg, 40% yield) was isolated as a white solid after purification by flash chromatography over silica gel (eluting in 50-100% EtOAc/hexane). ¹H NMR (400 MHz, DMSO-d₆) δ ppm 8.02 (br. s., 1H), 7.77 (d, J=8.0 Hz, 1H), 7.46-7.64 (m, 2H), 3.16 (d, J=3.0 Hz, 2H), 1.27 (s, 6H); MS (EI) m/z=255.1 [M+1]⁺.

A solution of 6-bromo-4,4-dimethyl-3,4-dihydroisoquinolin-1(2H)-one (500 mg, 1.97 mmol), diboron pinacol ester (752 mg, 2.96 mmol), KOAc (773 mg, 7.88 mmol) and Pd(dppf)Cl₂ (43 mg, 0.06 mmol) in dioxane (7 mLl) was heated for 2 hours at 100° C. under reflux. At completion the reaction was cooled to room temperature, filtered and concentrated the purified by flash chromatography over silica gel, (2-5% DCM/MeOH eluent). The product containing fractions were concentrated, taken up in hexanes, sonicated and filtered to afford 4,4-dimethyl-6-(4,4,5,5-tetramethyl-1,3,2-dioxaborolan-2-yl)-3,4-dihydroisoquinolin-1(2H)-one (511 mg, 86% yield) as a white solid. ¹H NMR (300 MHz, CHLOROFORM-d) δ ppm 8.09 (d, J=7.6 Hz, 1H), 7.71-7.87 (m, 2H), 3.33 (d, J=3.1 Hz, 2H), 1.39 (m, J=8.0 Hz, 18H); MS (EI) m/z=302.2 [M+1]⁺.

General method C was applied to 4-(6-amino-5-bromopyridin-3-yl)-N-cyclopropylbenzenesulfonamide hydrobromide (92 mg, 0.25 mmol) and 4,4-dimethyl-6-(4,4,5,5-tetramethyl-1,3,2-dioxaborolan-2-yl)-3,4-dihydroisoquinolin-1(2H)-one (75 mg, 0.25 mmol) to give 4-(6-amino-5-(4,4-dimethyl-1-oxo-1,2,3,4-tetrahydroisoquinolin-6-yl)pyridin-3-yl)-N-cyclopropylbenzenesulfonamide (43 mg, 37% yield) as a white solid after purification by flash chromatography over silica gel (2-5% MeOH/DCM eluent). ¹H NMR (400 MHz, DMSO-d₆) δ ppm 8.61 (s, 1H), 8.06 (d, J=8.5 Hz, 2H), 7.96-8.02 (m, 2H), 7.80 (d, J=1.5 Hz, 1H), 7.75 (dd, J=7.5, 1.5 Hz, 1H), 7.62 (d, J=8.5 Hz, 2H), 6.00 (s, 2H), 3.20 (d, J=2.0 Hz, 2H), 2.06-2.18 (m, 1H), 1.33 (s, 6H), 0.33-0.55 (m, 4H); MS (EI) m/z=463.6 [M+1]⁺.

6.36. Synthesis of 1-(4-(5-amino-6-(1'-oxo-2',3'-dihydro-1'H-spiro[cyclopropane-1,4'-isoquinolin]-6'-yl)pyrazin-2-yl)phenyl)cyclopropanecarbonitrile The captioned compound was prepared by the method shown below:

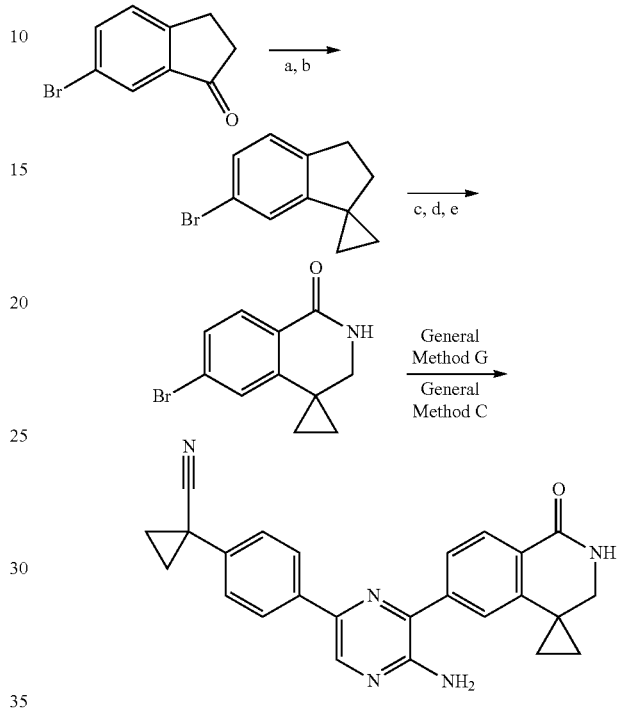

wherein:
a is Me₃SBr, n-BuLi, THF, 0° C.; b is Et₂Zn, TFA, CH₂I₂, DCM, 0° C.; c is KMnO₄, 1.5 M aq. MgSO₄, acetone; d is HONH₂—HCl, NaOAc, THF, then MsOH, TEA, THF; and e is BF₃MeOH, DCM, then TiCl₄.

A 2.5 M solution of n-BuLi in hexanes (23.6 mL, 59 mmol) was added dropwise to a 0° C. slurry of methyltriphenylphosphonium bromide (16.8 g, 47.0 mmol) in THF (200 mL). After 1 h, a solution of 6-bromo-2,3-dihydro-1H-inden-1-one (10.0 g, 47.0 mmol) in THF (50 mL) was added to the resulting solution and the reaction cold bath was removed. Upon completion, the reaction was quenched with water (40 mL). The layers were separated and the aqueous layer was extracted with EtOAc (2×40 mL). The combined organics were washed with brine (50 mL), dried over Na₂SO₄, filtered and concentrated to afford 6-bromo-1-methylene-2,3-dihydro-1H-indene (6.06 g, 62% yield) as a clear oil after purification by flash chromatography over silica gel (hexane eluent). ¹H NMR (400 MHz, CHLOROFORM-d) δ ppm 7.61 (d, J=1.5 Hz, 1H), 7.32 (dd, J=8.0, 1.8 Hz, 1H), 7.13 (d, J=8.0 Hz, 1H), 5.45 (t, J=2.5 Hz, 1H), 5.08 (t, J=2.1 Hz, 1H), 2.88-2.98 (m, 2H), 2.78-2.86 (m, 2H); MS (EI) m/z=210.1 [M+1]⁺.

A 1.1 M toluene solution of diethyl zinc (104.0 mL, 114.8 mmol) was added to a reaction vessel containing DCM (100 mL) and cooled to 0° C. TFA (8.9 ml, 114.8 mmol) was added to the resulting solution and the reaction was stirred at 0° C. for 15 min. To the cooled solution was added CH₂I₂ (9.26 mL, 114.8 mmol), and the reaction was stirred for an additional 15 minutes at 0° C. Then, a solution of 6-bromo-1-methylene-2,3-dihydro-1H-indene (6.0 g, 28.7 mmol) in DCM (90 mL) was added and the reaction was maintained 0° C. for another 15 min, then allowed to gradually warm to room temperature. Upon completion, the reaction was quenched with a sat. aq. NH$_4$Cl (100 mL) and diluted with DCM (200 mL). The layers were separated and the aqueous layer was washed with DCM (2×100 mL). The combined organics were washed with brine (100 mL), dried over Na$_2$SO$_4$, then filtered and concentrated. 6'-bromo-2',3'-dihydrospiro[cyclopropane-1,1'-indene] (5.9 g, 93% yield) was obtained after purification by flash chromatography (hexanes eluent) as a clear oil. $^1$H NMR (400 MHz, CHLOROFORM-d) δ ppm 7.22 (dd, J=7.9, 1.9 Hz, 1H), 7.05 (d, J=7.8 Hz, 1H), 6.78 (d, J=1.8 Hz, 1H), 2.99 (t, J=7.5 Hz, 2H), 2.06-2.20 (t, 2H), 0.83-1.03 (m, 4H); MS (EI) m/z=224.1 [M+1]$^+$.

To a solution of 6'-bromo-2',3'-dihydrospiro[cyclopropane-1,1'-indene] (5.7 g, 25.6 mmol) in acetone (78 mL) and 1.5 M aq. MgSO$_4$ (29 mL) was added KMnO$_4$ (4.46 g, 28.2 mmol). The reaction was stirred overnight at room temperature. Upon completion, the reaction was filtered over celite and concentrated. The residue was partitioned between water (100 mL) and EtOAc (200 mL), and the layers were separated. The organic was washed with brine, dried over Na$_2$SO$_4$, then filtered and concentrated. 6'-bromospiro[cyclopropane-1,1'-inden]-3'(2'H)-one (2.11 g, 39% yield) was isolated as a white solid after flash chromatography over silica gel (5% EtOAc/hexane eluent). $^1$H NMR (400 MHz, CHLOROFORM-d) δ ppm 7.59 (d, J=8.3 Hz, 1H), 7.45 (dd, J=8.0, 1.5 Hz, 1H), 7.14 (d, J=1.3 Hz, 1H), 2.76 (s, 2H), 1.15-1.34 (m, 4H); MS (EI) m/z=238.1 [M+1]$^+$.

A solution of 6'-bromospiro[cyclopropane-1,1'-inden]-3'(2'H)-one (2.1 g, 8.86 mmol), hydroxylamine HCl (1.23 g, 17.7 mmol) and NaOAc (4.32 g, 53.1 mmol) in MeOH (160 mL) was stirred overnight at room temperature. The reaction was concentrated, slurried water (40 mL), then sonicated and filtered. The precipitate was dried under high vacuum to give (E)-6'-bromospiro[cyclopropane-1,1'-inden]-3'(2'H)-one oxime (2.23 g, 100% yield) as a white solid. MS (EI) m/z=253.1[M+1]$^+$.

To a 0° C. solution of (E)-6'-bromospiro[cyclopropane-1,1'-inden]-3'(2'H)-one oxime (500 mg, 1.98 mmol) in THF (5 mL) was added triethylamine (332 μL, 2.38 mmol) followed by slow addition of MsCl (170 μL, 2.18 mmol). The reaction was stirred 10 minutes at 0° C. then concentrated. The residue was triturated from methanol (5 mL) to afford (E)-6'-bromospiro[cyclopropane-1,1'-inden]-3'(2'H)-one O-methylsulfonyl oxime (653 mg, 100% yield) as a white solid after drying under high vacuum. $^1$H NMR (300 MHz, CHLOROFORM-d) δ ppm 7.64 (d, J=8.4 Hz, 1H), 7.42 (dd, J=8.3, 1.6 Hz, 1H), 6.98 (d, J=1.5 Hz, 1H), 3.26 (s, 3H), 3.15 (s, 2H), 1.06-1.42 (m, 4H); MS (EI) m/z=331.2 [M+1]$^+$.

A solution of (E)-6'-bromospiro[cyclopropane-1,1'-inden]-3'(2'H)-one-O-methylsulfonyl oxime (653 mg, 1.98 mmol) in DCM (10 mL) was cooled to 0° C. BF$_3$MeOH (362 μL, 4.36 mmol) was added to the cooled solution, followed by slow addition of TiCl$_4$ (304 μL, 2.77 mmol) and the reaction was maintained at 0° C. for 4 h. At completion, the reaction was quenched with water (10 mL). The layers were separated and aqueous layer was washed with DCM (2×10 mL). The combined organics were dried over Na$_2$SO$_4$, filtered and concentrated. 6'-bromo-2',3'-dihydro-1'H-spiro[cyclopropane-1,4'-isoquinolin]-1'-one (228 mg, 0.90 mmol, 46% yield) was isolated as a white solid after purification by flash chromatography (50-100% EtOAc/hexane eluent). $^1$H NMR (400 MHz, CHLOROFORM-d) δ ppm 7.98 (d, J=8.3 Hz, 1H), 7.46 (dd, J=8.3, 1.8 Hz, 1H), 7.01 (d, J=1.8 Hz, 1H), 5.94 (br. s., 1H), 3.37 (d, J=2.8 Hz, 3H), 0.94-1.20 (m, 4H); MS (EI) m/z=253.1 [M+1]$^+$.

General Method G was applied to 6'-bromo-2',3'-dihydro-1'H-spiro[cyclopropane-1,4'-isoquinolin]-1'-one (228 mg, 0.90 mmol) to provide after purification by flash chromatography over silica gel (50-100% EtOAc/hexanes), 6'-(4,4,5,5-tetramethyl-1,3,2-dioxaborolan-2-yl)-2',3'-dihydro-1'H-spiro[cyclopropane-1,4'-isoquinolin]-1'-one (199 mg, 74% yield) as a white solid. $^1$H NMR (300 MHz, CHLOROFORM-d) δ ppm 8.12 (d, J=7.6 Hz, 1H), 7.77 (dd, J=7.6, 1.0 Hz, 1H), 7.30 (s, 1H), 3.37 (d, J=2.3 Hz, 2H), 1.36 (s, 12H), 0.94-1.22 (m, 4H); MS (EI) m/z=300.2[M+1]$^+$.

General method C was applied to 1-(4-(5-amino-6-bromopyrazin-2-yl)phenyl)cyclopropanecarbonitrile (95 mg, 0.30 mmol) and 6'-(4,4,5,5-tetramethyl-1,3,2-dioxaborolan-2-yl)-2',3'-dihydro-1'H-spiro][cyclopropane-1,4'-isoquinolin]1'-one (100 mg, 0.33 mmol) to provide 1-(4-(5-amino-6-(1'-oxo-2',3'-dihydro-1'H-spiro[cyclopropane-1,4'-isoquinolin]-6'-yl)pyrazin-2-yl)phenyl)cyclopropanecarbonitrile (44 mg, 36% yield) after flash chromatography over silica gel (2-5% MeOH/DCM eluent). $^1$H NMR (400 MHz, DMSO-d$_6$) δ ppm 0.76-1.07 (m, 4H) 1.08-1.35 (m, 4H) 1.44-1.63 (m, 2H) 1.65-1.86 (m, 2H) 6.37 (s, 1H) 7.10-7.51 (m, 3H) 7.68 (d, J=7.78 Hz, 1H) 7.83-8.28 (m, 4H) 8.57 (s, 1H). MS (EI) m/z: 408 [M+H]$^+$. HPLC (Sunfire C18 4.6 mm×50 mm, 10-90% MeCN:10 mM aq NH$_4$OAc, 2 min gradient) t$_R$=1.69 min, 100% integrated area.

6.37. Synthesis of 4-(5-amino-6-(3'-oxospiro[cyclopropane-1,1'-isoindolin]-6'-yl)pyrazin-2-yl)-N-cyclopropylbenzenesulfonamide The captioned compound was prepared by the method shown below:

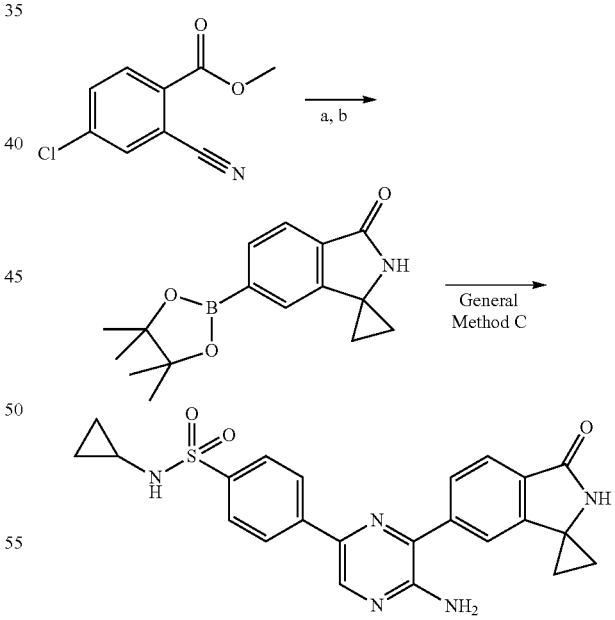

wherein:
a is Ti(OiPr)$_4$, EtMgBr, Et$_2$O; and b is (Bpin)$_2$, Pd(dba)$_3$, P(Cy)$_3$, dioxane.

To a solution of methyl 4-chloro-2-cyanobenzoate (2.0 g, 10.2 mmol) in Et$_2$O (40 mL) was added Ti(OiPr)$_4$ (3.43 ml, 11.7 mmol). After cooling to 0° C., a 3.0 M solution of EtMgBr in Et$_2$O (6.8 ml, 20.4 mmol) was added slowly. The reaction was warmed to room temperature and stirred for 3 h.

Upon completion, the reaction was quenched with 1.0 M HCl (20 mL) then filtered over celite. The layers were separated and the aqueous layer was washed with EtOAc (2×20 mL). The combined organics were dried over $Na_2SO_4$, then filtered and concentrated. The crude product was purified by flash chromatography over silica gel (2-5% MeOH/DCM eluent) to provide 6'-chlorospiro[cyclopropane-1,1'-isoindolin]-3'-one (400 mg, 21% yield) as a yellow solid. $^1$H NMR (400 MHz, DMSO-$d_6$) δ ppm 8.75 (br. s., 1H), 7.66 (d, J=8.5 Hz, 1H), 7.40-7.54 (m, 2H), 1.47 (dt, J=11.2, 2.8 Hz, 4H); MS m/z $C_{10}H_8ClNO$ [M+1]$^+$=194.6.

A solution of 6'-chlorospiro[cyclopropane-1,1'-isoindolin]-3'-one (380 mg, 1.96 mmol), bis(pinacolato)diboron (808 mg, 3.18 mmol), KOAc (677 mg, 6.9 mmol), $P(Cy)_3$ (137 mg, 0.49 mmol) and $Pd(dba)_3$ (180 mg, 0.20 mmol) in dioxane (8 ml) was heated overnight at 100° C. under a reflux condenser. At completion, the reaction was allowed to cool to room temperature, diluted in DCM (40 mL), sonicated and filtered. The filtrate was purified by flash chromatography over silica gel (50/100% EtOAc/hexane eluent). The product containing fractions were taken up in hexanes, then sonicated and filtered to afford 6'-(4,4,5,5-tetramethyl-1,3,2-dioxaborolan-2-yl)spiro[cyclopropane-1,1'-isoindolin]-3'-one (520 mg, 93% yield) as a yellow solid. $^1$H NMR (400 MHz, METHANOL-$d_4$) δ ppm 7.70-7.91 (m, 2H), 7.56 (s, 1H), 1.46-1.68 (m, 4H), 1.15-1.43 (m, 12H); MS (EI) m/z=286.1 [M+1]$^+$.

General method B was applied to 4-(5-amino-6-bromopyrazin-2-yl)-N-cyclopropyl-benzenesulfonamide (140 mg, 0.38 mmol) and 6'-(4,4,5,5-tetramethyl-1,3,2-dioxaborolan-2-yl)spiro[cyclopropane-1-1'-isoindolin]3'-one (120 mg, 0.42 mmol) to provide 4-(5-amino-6-(3'-oxospiro[cyclopropane-1,1'-isoindolin]-6'-yl)pyrazin-2-yl)-N-cyclopropylbenzenesulfonamide (58 mg, 34% yield) after purification by flash chromatography over silica gel (2-5% MeOH/DCM eluent). $^1$H NMR (400 MHz, DMSO-$d_6$) δ ppm 0.29-0.58 (m, 4H) 1.36-1.68 (m, 4H) 2.13 (d, J=2.51 Hz, 1H) 6.62 (s, 1H) 7.62 (s, 1H) 7.74-7.96 (m, 5H) 8.21 (d, J=8.53 Hz, 2H) 8.70 (s, 1H) 8.75 (s, 1H) 8.96-9.32 (m, 1H). MS (EI) m/z: 448 [M+H]$^+$. HPLC (Sunfire C18 4.6 mm×50 mm, 10-90% MeCN:10 mM aq $NH_4OAc$, 2 min gradient) $t_R$=1.47 min, 97% integrated area.

6.38. Synthesis of 5-(3-amino-6-(4-(N-cyclopropyl-N-methylsulfamoyl)phenyl)pyrazin-2-yl)-N-methylindoline-1-carboxamide The captioned compound was prepared by the method shown below:

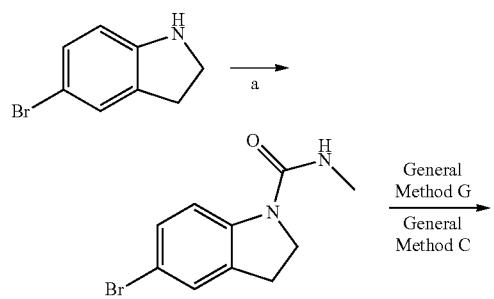

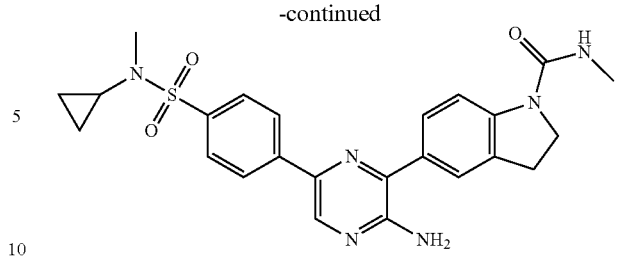

wherein:
a is methylisocyanate, DIEA, THF.

To a solution of 5-bromoindoline (1.0 g, 5.05 mmol) and DIEA (1.9 mL, 11.11 mmol) in THF (40 mL) was added methylisocyanate (346 mg, 6.06 mmol). The reaction was maintained at room temperature for 4 h. The resulting precipitate was filtered and dried under vacuum to afford 5-bromo-N-methylindoline-1-carboxamide (935 mg, 72% yield) as a white solid. $^1$H NMR (400 MHz, DMSO-$d_6$) δ ppm 7.75 (d, J=8.78 Hz, 1H), 7.17-7.31 (m, 2 H), 6.60 (d, J=4.27 Hz, 1H), 3.85 (t, J=8.78 Hz, 2H), 3.10 (t, J=8.66 Hz, 2H), 2.65 (d, J=4.27 Hz, 3H); MS (EI) m/z=255.1[M+1]$^+$.

General method G was applied to 5-bromo-N-methylindoline-1-carboxamide (935 mg, 3.67 mmol) to provide N-methyl-5-(4,4,5,5-tetramethyl-1,3,2-dioxaborolan-2-yl)indoline-1-carboxamide as a white foam (1.10 g, 100% yield) after purification by flash chromatography (5% MeOH/DCM). $^1$H NMR (400 MHz, CHLOROFORM-d) δ ppm 1.34 (s, 12H) 3.10-3.22 (m, 2H) 3.90 (s, 2H) 4.54-4.66 (m, 1H) 7.60 (br. s, 1H) 7.66 (br. d, J=1.00 Hz, 1H) 7.85 (br. d, J=1.00 Hz, 1H) 7.84-7.91 (m, 1H); MS (EI) m/z=301.0 [M−1]$^−$.

Method C was applied to N-methyl-5-(4,4,5,5-tetramethyl-1,3,2-dioxaborolan-2-yl)indoline-1-carboxamide (85 mg, 0.28 mmol) and 4-(5-amino-6-bromopyrazin-2-yl)-N-cyclopropyl-N-methylbenzenesulfonamide (100 mg, 0.26 mmol). The organic layer was decanted then triturated with $Et_2O$ to provide 5-(3-amino-6-(4-(N-cyclopropyl-N-methylsulfamoyl)phenyl)pyrazin-2-yl)-N-methylindoline-1-carboxamide as a yellow solid (35 mg, 28% yield). $^1$H NMR (400 MHz, DMSO-$d_6$) δ ppm 8.58-8.66 (m, 1H), 8.20-8.31 (m, 1H), 7.92-7.99 (m, 1H), 7.79-7.88 (m, 2H), 7.47-7.64 (m, 2H), 6.61-6.71 (m, 1H), 6.60-6.65 (m, 1H), 6.58-6.71 (m, 2H), 6.42-6.49 (m, 2H), 3.88-3.98 (m, 2H), 3.13-3.25 (m, 2H), 2.68 (s, 3H), 2.08 (s, 3H), 1.79-1.88 (m, 1H), 0.62-0.81 (m, 4H); MS (EI) m/z=479.1[M+1]$^+$.

6.39. Synthesis of 4-(5-amino-6-(8-oxo-5,6,7,8-tetrahydro-2,7-naphthyridin-3-yl)pyrazin-2-yl)-N-cyclopropylbenzenesulfonamide The captioned compound was prepared by the method shown below:

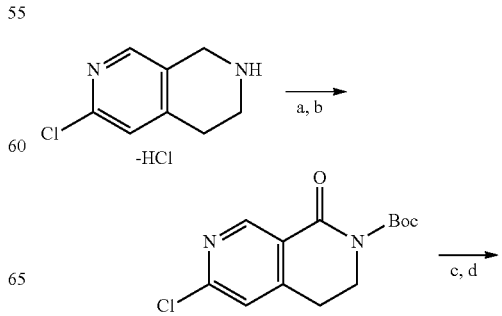

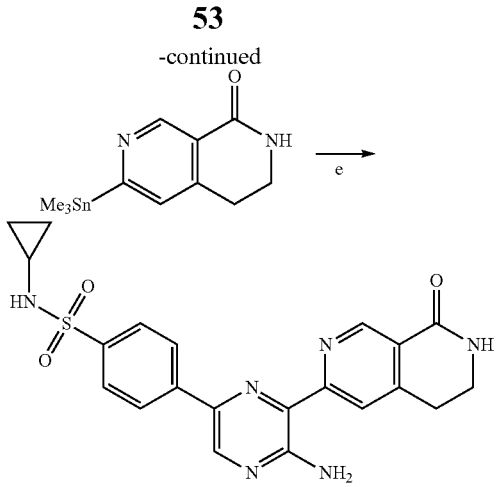

wherein:
a is Boc$_2$O, TEA, DCM; b is NaIO$_4$, RuCl$_3$, DCM, water, MeCN; c is HCl, dioxane; and d is Me$_6$Sn$_2$, Pd(PPh$_3$)$_4$, dioxane, 110° C.

To a solution of 6-chloro-1,2,3,4-tetrahydro-2,7-naphthyridine hydrochloride (5.0 g, 24.4 mmol) and ditertbutyl dicarbonate (8.0 g, 36.6 mmol) in DCM (100 mL) at room temperature was added triethylamine (10.2 mL, 73.2 mmol). Upon completion, the reaction was diluted in DCM (100 mL), washed with a sat. aq. NaHCO$_3$, dried over Na$_2$SO$_4$, filtered and concentrated. This residue was purified by flash chromatography over silica gel (20% EtOAc/hexane eluent) to afford tert-butyl 6-chloro-3,4-dihydro-2,7-naphthyridine-2(1H)-carboxylate (4.0 g, 61% yield) as a clear oil. $^1$H NMR (400 MHz, METHANOL-d$_4$) δ ppm 8.17 (s, 1H), 7.30 (s, 1H), 4.60 (s, 2H), 3.66 (t, J=5.9 Hz, 2H), 2.88 (t, J=5.8 Hz, 2H), 1.43-1.61 (m, 9H); MS (EI) m/z=269.7 [M+1]$^+$.

To a solution of NaIO$_4$ (9.56 g, 44.7 mmol) and RuCl$_3$ (927 mg, 4.47 mmol) in water (50 mL), DCM (50 mL) and MeCN (2 mL) was added a solution of tert-butyl 6-chloro-3,4-dihydro-2,7-naphthyridine-2(1H)-carboxylate (4.0 g, 14.9 mmol) in DCM (25 mL). This reaction was stirred at room temperature for 2 h. At completion, the reaction was and was quenched with isopropanol (10 mL), filtered over celite and the filter cake was washed with DCM (20 mL). The filtrate was partitioned in a separatory funnel and the layers were separated. The organic layer was extracted with DCM (2×20 mL) and the combined organics were dried over Na$_2$SO$_4$, then filtered and concentrated. The residue was purified by flash chromatography over silica gel (20-50% EtOAc/hexane eluent) to give tert-butyl 6-chloro-1-oxo-3,4-dihydro-2,7-naphthyridine-2(1H)-carboxylate (3.0 g, 71% yield) as a yellow crystalline solid. $^1$H NMR (400 MHz, METHANOL-d$_4$) δ ppm 8.92 (s, 1H), 7.47 (s, 1H), 4.03 (t, J=6.3 Hz, 2H), 3.09 (t, J=6.1 Hz, 2H), 1.54-1.62 (m, 9H); MS (EI) m/z=283.7 [M+1]$^+$.

To a solution of tert-butyl 6-chloro-1-oxo-3,4-dihydro-2,7-naphthyridine-2(1H)-carboxylate (3.0 g, 10.6 mmol) in DCM (20 mL) was added 4N HCl solution in dioxane (10 mL). After stirring 20 minutes at room temperature, the reaction was diluted with DCM (50 mL), then sonicated and filtered to give 6-chloro-3,4-dihydro-2,7-naphthyridin-1(2H)-one hydrochloride (2.22 g, 93% yield) as a white solid. $^1$H NMR (300 MHz, DMSO-d$_6$) δ ppm 8.70 (s, 1H), 8.23 (br. s., 1H), 7.57 (s, 1H), 3.40 (t, J=6.6, 2.8 Hz, 2H), 2.96 (t, J=6.6 Hz, 2H); MS (EI) m/z=183.6 [M+1]$^+$.

A solution of 6-chloro-3,4-dihydro-2,7-naphthyridin-1(2H)-one hydrochloride (800 mg, 3.7 mmol), hexamethylditin (1.83 g, 5.6 mmol) and Pd(PPh$_3$)$_4$ (214 mg, 0.19 mmol) in dioxane (40 mL) was degassed under bubbling nitrogen then heated at 110° C. for 4 h. At completion, the reaction was concentrated and purified by flash chromatography over neutral alumina (100% EtOAc eluent, then 5% MeOH/DCM eluent). This yielded 6-(trimethylstannyl)-3,4-dihydro-2,7-naphthyridin-1(2H)-one (1.22 g, 100% yield) as a brown oil that was used without further purification. MS (EI) m/z [M+1]$^+$=312.

A solution of 4-(5-amino-6-bromopyrazin-2-yl)-N-cyclopropylbenzenesulfonamide (150 mg, 0.41 mmol), 6-(trimethylstannyl)-3,4-dihydro-2,7-naphthyridin-1(2H)-one (150 mg, 0.48 mmol) and Pd(PPh$_3$)$_4$ (23 mg, 0.02 mmol) in dioxane (2 mL) was heated in the microwave 20 min at 150° C. At completion, the reaction mixture was purified by reverse phase preparatory HPLC to provide 4-(5-amino-6-(8-oxo-5,6,7,8-tetrahydro-2,7-naphthyridin-3-yl)pyrazin-2-yl)-N-cyclopropylbenzenesulfonamide (8 mg, 5% yield) as an orange solid after lyophilization. $^1$H NMR (400 MHz, DMSO-d$_6$) δ ppm 9.02 (s, 1H), 8.87 (s, 1H), 8.59 (s, 1H), 8.35 (d, J=8.5 Hz, 2H), 8.17 (br. s., 1H), 7.84-7.99 (m, 3H), 3.51 (t, 2H), (t, J=6.3 Hz, 2H), 0.29-0.57 (m, 4 H); MS (EI) m/z=437.5 [M+1]$^+$.

6.40. Synthesis of 4-(5-amino-6-(4-bromo-1-hydroxyisoquinolin-6-yl)pyrazin-2-yl)-N-cyclopropyl-N-methylbenzenesulfonamide The captioned compound was prepared by the method shown below:

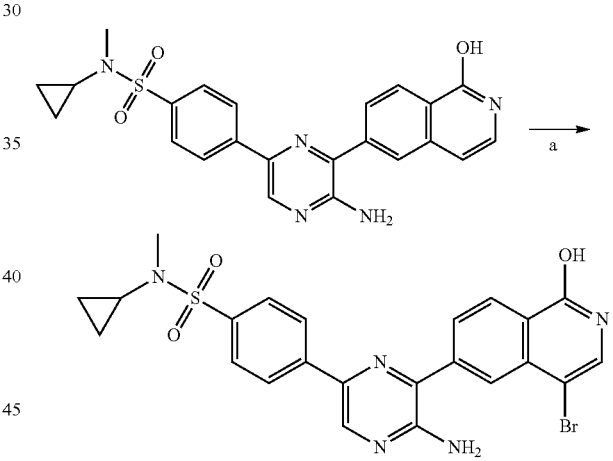

wherein:
a is DMF:DMF-DMA (10:1), NBS.

To a room temperature slurry of 4-(5-amino-6-(1-hydroxyisoquinolin-6-yl)pyrazin-2-yl)-N-cyclopropyl-N-methylbenzenesulfonamide hydrochloride (1.00 g, 2.07 mmoL, prepared by general method C) in DMF (10 mL) was added 1,1-dimethoxy-N,N-dimethylmethanamine (1 mL). Within minutes, the slurry discharged to a solution. Then, N-bromosuccinimide (386 mg, 2.17 mmol) was added in one portion. After 1 h the reaction was concentrated and flashed over silica gel (4-8% MeOH/DCM eluent) to provide 4-(5-amino-6-(4-bromo-1-hydroxyisoquinolin-6-yl)pyrazin-2-yl)-N-cyclopropyl-N-methylbenzenesulfonamide hydrochloride (480 mg, 43% yield). $^1$H NMR (400 MHz, DMSO-d$_6$) δ ppm 11.59-11.67 (br. s, 1H), 8.77 (s, 1H), 8.36 (d, J=8.3 Hz, 1H), 8.24-8.30 (m, 2H), 8.17 (d, J=1.5 Hz, 1H), 7.99 (dd, J=8.3, 1.5 Hz, 1H), 7.86 (d, J=8.5 Hz, 2H), 7.62 (d, J=6.0 Hz, 1H), 6.76 (br. s, 2H), 2.69 (s, 3H), 1.80-1.90 (m, 1H), 0.76 (s, 2H), 0.65-0.73 (m, 2H); MS (EI) m/z=527.4 [M+1]$^+$.

6.41. Additional Compounds

Numerous additional compounds were prepared, some of which are listed below in Table 1. Table 1 also provides in vitro test results, which were obtained using the assay described in Example 6.42, wherein "-" indicates that a measurement was not obtained; *=$IC_{50}$<0.15 µM; =$IC_{50}$<0.05 µM; and *=$IC_{50}$<0.01 µM.

TABLE 1

| Compound | $IC_{50}$ (µM) | |
| --- | --- | --- |
| | 1 µM ATP | 50 µM ATP |
| 4-(6-amino-6'-fluoro-[3,3'-bipyridin]-5-yl)benzamide | — | — |
| 4-(2-amino-5-(1H-pyrazol-4-yl)pyridin-3yl)benzamide | — | * |
| 4-(2-amino-5-(4-sulfamoylphenyl)pyridin-3-yl)benzamide | — | * |
| 4-(2-amino-5-(1-(N,N-dimethylsulfamoyl)-1H-imidazol-4-yl)pyridin-3-yl)benzamide | — | — |
| 4-(5-(4-(1H-imidazol-1-yl)phenyl)-2-aminopyridin-3-yl)benzamide | — | * |
| 4-(2-amino-5-(4-benzoylphenyl)pyridin-3-yl)benzamide | — | * |
| 4-(2-amino-5-(4-fluorophenyl)pyridin-3-yl)-2-ethoxybenzamide | — | * |
| 3-amino-N-(pentan-2-yl)-6-(3,4,5-trimethoxyphenyl)pyrazine-2-carboxamide | — | * |
| 3-amino-N-cyclohexyl-6-(3,4-dimethoxyphenyl)pyrazine-2-carboxamide | — | * |
| 4-(2-amino-5-(4-(2-oxo-2-(pyrrolidin-1-yl)ethyl)phenyl)pyridin-3-yl)benzamide | — | * |
| 4-(2-amino-5-(4-(N-methylsulfamoyl)phenyl)pyridin-3-yl)benzamide | — | * |
| 3-amino-N-cyclohexyl-6-(4-(methoxymethyl)phenyl)pyrazine-2-carboxamide | — | * |
| 4-(2-amino-5-(4-(benzylcarbamoyl)phenyl)pyridin-3-yl)-N-hydroxybenzamide | — | * |
| 6-(2-amino-5-(4-fluorophenyl)pyridin-3-yl)-3,4-dihydroisoquinolin-1(2H)-one | * | ** |
| 4-(6-amino-5-(4-hydroxyquinazolin-7-yl)pyridin-3-yl)-N,N-diethylbenzenesulfonamide | ** | *** |
| 4-(2-amino-5-(4-(N,N-diethylsulfamoyl)phenyl)pyridin-3-yl)-2-fluorobenzamide | — | ** |
| 4-(2-amino-5-(4-(N-cyclopropylsulfamoyl)phenyl)pyridin-3-yl)benzamide | ** | ** |
| 4-(6-amino-5-(3-hydroxy-1H-indazol-6-yl)pyridin-3-yl)-N,N-diethylbenzenesulfonamide | — | * |
| 3-amino-N-cyclohexyl-6-(4-(N-ethylsulfamoyl)phenyl)pyrazine-2-carboxamide | * | ** |
| 4-(6-amino-5-(2-oxo-2,3,4,5-tetrahydro-1H-benzo[b]azepin-7-yl)pyridin-3-yl)-N,N-diethylbenzenesulfonamide | — | * |
| 4-(6-amino-5-(1-oxo-1,2,3,4-tetrahydroisoquinolin-6-yl)pyridin-3-yl)-N-cyclopropylbenzenesulfonamide | *** | *** |
| 2'-amino-5'-(4-(N,N-diethylsulfamoyl)phenyl)-[2,3'-bipyridine]-5-carboxamide | ** | *** |
| 4-(6-amino-5-(3-oxo-2,3-dihydrobenzo[d]isoxazol-6-yl)pyridin-3-yl)-N,N-diethylbenzenesulfonamide | — | * |
| 4-(5-amino-6-(1-oxo-1,2,3,4-tetrahydroisoquinolin-6-yl)pyrazin-2-yl)-N,N-di(trideuteromethyl)benzenesulfonamide | *** | *** |
| 4-(5-(4-(N-acetylsulfamoyl)phenyl)-2-aminopyridin-3-yl)benzamide | — | * |
| 4-(6-amino-5-(4-hydroxyquinazolin-7-yl)pyridin-3-yl)-N-ethylbenzenesulfonamide | ** | *** |
| 2'-amino-5'-(4-(N-ethylsulfamoyl)phenyl)-[2,3'-bipyridine]-5-carboxamide | ** | *** |
| 4-(2-amino-5-(2-chloro-4-(N-cyclopropylsulfamoyl)phenyl)pyridin-3-yl)benzamide | — | * |
| 4-(2-amino-5-(4-(2-(dimethylamino)-2-oxoethoxy)phenyl)pyridin-3-yl)benzamide | — | * |
| 3-amino-N-(4-(aminomethyl)cyclohexyl)-6-(4-(N-cyclopropylsulfamoyl)phenyl)pyrazine-2-carboxamide | ** | *** |
| 4-(2-amino-5-(4-propoxyphenyl)pyridin-3-yl)benzamide | — | * |
| 4-(5-amino-6-(1-oxo-1,2,3,4-tetrahydroisoquinolin-6-yl)pyrazin-2-yl)-N-cyclopropyl-N-trideuteromethylbenzenesulfonamide | *** | *** |
| 6-(2-amino-5-(4-(ethylsulfonyl)phenyl)pyridin-3-yl)-3,4-dihydroisoquinolin-1(2H)-one | ** | ** |
| 4-(6-amino-6-(5-phenyl-1H-imidazol-2-yl)pyrazin-2-yl)-N-cyclopropylbenzenesulfonamide | — | ** |
| 5-(6-amino-5-(1-oxo-1,2,3,4-tetrahydroisoquinolin-6-yl)pyridin-3-yl)-N-(2,2,2-trifluoroethyl)thiophene-2-carboxamide | * | ** |
| 6-(2-amino-5-(5-methylthiophen-2-yl)pyridin-3-yl)-3,4-dihydroisoquinolin-1(2H)-one | ** | *** |
| 6-(5-amino-6-(1-oxo-1,2,3,4-tetrahydroisoquinolin-6-yl)pyrazin-2-yl)-N-cyclopropyl-N-trideuteromethylpyridine-3-sulfonamide | *** | *** |
| 6-(2-amino-5-(2-(dimethylamino)thiazol-4-yl)pyridin-3-yl)-3,4-dihydroisoquinolin-1(2H)-one | — | ** |
| (E)-4-(6-amino-5-(5-(hydroxyimino)-5,6,7,8-tetrahydronaphthalen-2-yl)pyridin-3-yl)-N-ethylbenzenesulfonamide | ** | *** |

TABLE 1-continued

| Compound | IC$_{50}$ (μM) | |
|---|---|---|
| | 1 μM ATP | 50 μM ATP |
| 4-(6-amino-5-(1-oxo-1,2,3,4-tetrahydroisoquinolin-6-yl)pyridin-3-yl)-N-cyclopropyl-N-methylbenzenesulfonamide | *** | *** |
| N-cyclopropyl-4-(3-(1-oxo-1,2,3,4-tetrahydroisoquinolin-6-yl)-1H-pyrrolo[2,3-b]pyridin-5-yl)benzenesulfonamide | ** | *** |
| methyl 2-(4-(6-amino-5-(1-oxo-1,2,3,4-tetrahydroisoquinolin-6-yl)pyridin-3-yl)-N-methylphenylsulfonamido)acetate | * | ** |
| 4-(6-amino-5-(1-oxo-1,2,3,4-tetrahydroisoquinolin-6-yl)pyridin-3-yl)-N-ethyl-N-methylbenzenesulfonamide | *** | *** |
| 4-(5-amino-6-(1-oxo-1,2,3,4-tetrahydroisoquinolin-6-yl)pyrazin-2-yl)-N-cyclopropyl-N-methylbenzenesulfonamide | *** | *** |
| 4-(5-amino-6-(1-oxo-1,2,3,4-tetrahydroisoquinolin-6-yl)pyrazin-2-yl)-N-ethyl-N-methylbenzenesulfonamide | *** | *** |
| 6'-amino-N-ethyl-N-methyl-5'-(1-oxo-1,2,3,4-tetrahydroisoquinolin-6-yl)-[2,3'-bipyridine]-5-sulfonamide | *** | *** |
| 6-(3-amino-6-(4-((cyclopropylmethyl)sulfonyl)phenyl)pyrazin-2-yl)-3,4-dihydroisoquinolin-1(2H)-one | ** | *** |
| 4-(5-amino-6-(1-oxo-1,2,3,4-tetrahydroisoquinolin-6-yl)pyrazin-2-yl)-N-cyclopropyl-N-ethylbenzenesulfonamide | ** | *** |
| 4-(5-amino-6-(1-oxo-1,2,3,4-tetrahydroisoquinolin-6-yl)pyrazin-2-yl)-N-(cyclopropylmethyl)-N-ethylbenzenesulfonamide | *** | *** |
| 4-(5-amino-6-(1-oxo-1,2,3,4-tetrahydroisoquinolin-6-yl)pyrazin-2-yl)-N-(2,2-difluoroethyl)-N-methylbenzenesulfonamide | ** | *** |
| 6-(5-(4-(4-azaspiro[2.4]heptan-4-ylsulfonyl)phenyl)-2-aminopyridin-3-yl)-3,4-dihydroisoquinolin-1(2H)-one | ** | *** |
| 5-(6-amino-5-(1-oxo-1,2,3,4-tetrahydroisoquinolin-6-yl)pyridin-3-yl)-N-ethyl-N-methylthiophene-2-sulfonamide | ** | *** |
| 4-(5-amino-6-(1-oxo-1,2,3,4-tetrahydroisoquinolin-6-yl)pyrazin-2-yl)-N-methyl-N-propylbenzenesulfonamide | *** | *** |
| 6-(2-amino-5-(1,1-dioxido-2,3-dihydrobenzo[d]isothiazol-5-yl)pyridin-3-yl)-3,4-dihydroisoquinolin-1(2H)-one | ** | *** |
| 4-(5-amino-6-(1-oxo-1,2-dihydroisoquinolin-6-yl)pyrazin-2-yl)-N-cyclopropyl-N-methylbenzenesulfonamide | *** | *** |
| 4-(5-amino-6-(1-hydroxyisoquinolin-6-yl)pyrazin-2-yl)-N-ethyl-N-methylbenzenesulfonamide | *** | *** |
| 6'-amino-N-cyclopropyl-N-methyl-5'-(1-oxo-1,2,3,4-tetrahydroisoquinolin-6-yl)-[2,3'-bipyridine]-5-sulfonamide | *** | *** |
| 4-(6-amino-5-(7-oxo-4,5,6,7-tetrahydrothieno[2,3-c]pyridin-2-yl)pyridin-3-yl)-N-ethyl-N-methylbenzenesulfonamide | ** | *** |
| 6-(3-amino-6-(4-(piperidin-1-ylsulfonyl)phenyl)pyrazin-2-yl)isoquinolin-1(2H)-one | *** | *** |
| 4-(6-amino-5-(1-oxo-1,2-dihydroisoquinolin-6-yl)pyridin-3-yl)-N-cyclopropyl-N-methylbenzenesulfonamide | *** | *** |
| 6'-amino-N-cyclopropyl-N-methyl-5'-(1-oxo-1,2,3,4-tetrahydroisoquinolin-6-yl)-[3,3'-bipyridine]-6-sulfonamide | *** | *** |
| 4-(3-amino-6-(4-(N-cyclopropyl-N-methylsulfamoyl)phenyl)pyrazin-2-yl)-2-isopropoxybenzamide | ** | *** |
| 4-(5-amino-6-(1-oxo-1,2,3,4-tetrahydroisoquinolin-6-yl)pyrazin-2-yl)-N-trideuteromethyl-N-(2-dideutero-propyl)benzenesulfonamide | *** | *** |
| N-(4-(6-amino-5-(1-oxo-1,2,3,4-tetrahydroisoquinolin-6-yl)pyridin-3-yl)phenyl)ethanesulfonamide | ** | *** |
| 6'-amino-N-cyclopropyl-5'-(1-oxo-1,2,3,4-tetrahydroisoquinolin-6-yl)-[2,3'-bipyridine]-5-sulfonamide | *** | *** |
| tert-butyl 6-amino-5-(1-oxo-1,2,3,4-tetrahydroisoquinolin-6-yl)-5',6'-dihydro-[3,4'-bipyridine]-1'(2'H)-carboxylate | * | ** |
| 4-(5-amino-6-(1-oxo-1,2,3,4-tetrahydroisoquinolin-6-yl)pyrazin-2-yl)-N-methyl-N-((1R,2R)-2-methylcyclopropyl)benzenesulfonamide | *** | *** |
| 6-(2-amino-5-(2-oxoindolin-5-yl)pyridin-3-yl)-3,4-dihydroisoquinolin-1(2H)-one | ** | ** |
| 6-(5-amino-6-(1-oxo-1,2,3,4-tetrahydroisoquinolin-6-yl)pyrazin-2-yl)-N-ethyl-N-methylpyridine-3-sulfonamide | *** | *** |
| 6-amino-N,N-dimethyl-5-(1-oxo-1,2,3,4-tetrahydroisoquinolin-6-yl)-5',6'-dihydro-[3,4'-bipyridine]-1'(2'H)-sulfonamide | * | ** |
| 4-(5-amino-6-(1-oxo-1,2,3,4-tetrahydroisoquinolin-6-yl)pyrazin-2-yl)-N-cyclopropyl-2-fluoro-N-methylbenzenesulfonamide | *** | *** |
| 4-(5-amino-6-(1-oxo-1,2,3,4-tetrahydroisoquinolin-6-yl)pyrazin-2-yl)-N-cyclobutyl-N-methylbenzenesulfonamide | *** | *** |
| 6-(5-amino-6-(1-oxo-1,2,3,4-tetrahydroisoquinolin-6-yl)pyrazin-2-yl)-N-cyclopropyl-N-methylpyridine-3-sulfonamide | *** | *** |
| 4-(2-amino-1'-(2-cyanoacetyl)-1',2',3',6'-tetrahydro-[3,4'-bipyridin]-5-yl)-N-cyclopropyl-N-methylbenzenesulfonamide | * | * |
| 5-(5-amino-6-(1-oxo-1,2,3,4-tetrahydroisoquinolin-6-yl)pyrazin-2-yl)-N-cyclopropyl-N-methylpyridine-2-sulfonamide | ** | *** |
| 6'-amino-N-methyl-5'-(1-oxo-1,2,3,4-tetrahydroisoquinolin-6-yl)-N-propyl-[2,3'-bipyridine]-5-sulfonamide | *** | *** |
| 4-(5-amino-6-(1-oxo-1,2,3,4-tetrahydroisoquinolin-6-yl)pyrazin-2-yl)-N-cyclopropylbenzenesulfonamide | *** | *** |

TABLE 1-continued

| Compound | IC$_{50}$ (μM) | |
|---|---|---|
| | 1 μM ATP | 50 μM ATP |
| 6-(5-amino-6-(1-oxo-1,2,3,4-tetrahydroisoquinolin-6-yl)pyrazin-2-yl)-N-((1S,2S)-2-(methoxymethyl)cyclopropyl)-N-methylpyridine-3-sulfonamide | * | ** |
| 4-(5-amino-6-(1-oxo-1,2,3,4-tetrahydroisoquinolin-6-yl)pyrazin-2-yl)-2-chloro-N-ethyl-N-methylbenzenesulfonamide | *** | *** |
| 4-(5-amino-6-(1-oxo-1,2,3,4-tetrahydroisoquinolin-6-yl)pyrazin-2-yl)-N-ethyl-N,2-dimethylbenzenesulfonamide | *** | *** |
| 4-(5-amino-6-(1-oxo-1,2,3,4-tetrahydroisoquinolin-6-yl)pyrazin-2-yl)-N-ethylbenzenesulfonamide | *** | *** |
| 4-(5-amino-6-(1-oxo-1,2,3,4-tetrahydroisoquinolin-6-yl)pyrazin-2-yl)benzonitrile | ** | *** |
| 4-(6-amino-5-(1-oxo-1,2,3,4-tetrahydroisoquinolin-6-yl)pyridin-3-yl)-N-cyclobutyl-N-(2,2,2-trifluoroethyl)benzenesulfonamide | ** | *** |
| 4-(6-amino-5-(1-oxo-1,2,3,4-tetrahydroisoquinolin-6-yl)pyridin-3-yl)-N-cyclobutylbenzenesulfonamide | *** | *** |
| 2-(4-(5-amino-6-(1-oxo-1,2,3,4-tetrahydroisoquinolin-6-yl)pyrazin-2-yl)phenyl)-2-methylpropanenitrile | ** | *** |
| 4-(6-amino-5-(1-oxo-1,2,3,4-tetrahydroisoquinolin-6-yl)pyridin-3-yl)-2-chloro-N-cyclopropylbenzenesulfonamide | *** | *** |
| 4-(6-amino-5-(1-oxo-1,2,3,4-tetrahydroisoquinolin-6-yl)pyridin-3-yl)-N-cyclopropyl-2-fluorobenzenesulfonamide | *** | *** |
| 6-(3-amino-6-(1-methyl-1H-pyrazol-4-yl)pyrazin-2-yl)-3,4-dihydroisoquinolin-1(2H)-one | * | ** |
| N-allyl-4-(6-amino-5-(1-oxo-1,2,3,4-tetrahydroisoquinolin-6-yl)pyridin-3-yl)-N-methylbenzenesulfonamide | *** | *** |
| 4-(6-amino-5-(1-oxo-1,2,3,4-tetrahydroisoquinolin-6-yl)pyridin-3-yl)-N-cyclopropyl-N,2-dimethylbenzenesulfonamide | *** | *** |
| 4-(5-amino-6-(1-oxo-1,2,3,4-tetrahydroisoquinolin-6-yl)pyrazin-2-yl)-2-chloro-N-methyl-N-propylbenzenesulfonamide | *** | *** |
| 6-(3-amino-6-(4-(2,2,2-trifluoroacetyl)phenyl)pyrazin-2-yl)-3,4-dihydroisoquinolin-1(2H)-one | * | ** |
| 4-(5-amino-6-(4,4-dideutero-1-oxo-1,2,3,4-tetrahydroisoquinolin-6-yl)pyrazin-2-yl)-N-cyclopropyl-N-trideuteromethyl-benzenesulfonamide | *** | *** |
| 4-(5-amino-6-((2-hydroxypyridin-4-yl)ethynyl)pyrazin-2-yl)-N-cyclopropyl-N-methylbenzenesulfonamide | * | ** |
| 6-(2-amino-5-(4-((cyclopropyl(methyl)amino)methyl)phenyl)pyridin-3-yl)-3,4-dihydroisoquinolin-1(2H)-one | ** | *** |
| 6'-amino-N-cyclopropyl-4-methyl-5'-(1-oxo-1,2,3,4-tetrahydroisoquinolin-6-yl)-[2,3'-bipyridine]-5-sulfonamide | *** | *** |
| 6-(3-amino-6-(4-(tert-butyl)phenyl)pyrazin-2-yl)-3,4-dihydroisoquinolin-1(2H)-one | ** | *** |
| 6-(5-amino-6-(1-oxo-1,2,3,4-tetrahydroisoquinolin-6-yl)pyrazin-2-yl)-N-ethyl-N,4-dimethylpyridine-3-sulfonamide | *** | *** |
| 1-(4-(5-amino-6-(1-oxo-1,2,3,4-tetrahydroisoquinolin-6-yl)pyrazin-2-yl)phenyl)cyclopentanecarbonitrile | *** | *** |
| 4-(6-amino-5-(1-oxo-2,3,4,5-tetrahydro-1H-benzo[c]azepin-7-yl)pyridin-3-yl)-N-cyclopropyl-N-methylbenzenesulfonamide | *** | *** |
| 1-(4-(5-amino-6-(1-oxo-1,2,3,4-tetrahydroisoquinolin-6-yl)pyrazin-2-yl)phenyl)cyclopropanecarbonitrile | ** | *** |
| 4-(5-amino-6-(1-oxo-2,3,4,5-tetrahydro-1H-benzo[c]azepin-7-yl)pyrazin-2-yl)-N-ethyl-N-methylbenzenesulfonamide | ** | *** |
| 1-(4-(6-amino-5-(1-oxo-1,2,3,4-tetrahydroisoquinolin-6-yl)pyridin-3-yl)phenyl)cyclopropanecarbonitrile | ** | ** |
| 2-(4-(5-amino-6-(1-oxo-1,2-dihydroisoquinolin-6-yl)pyrazin-2-yl)phenyl)-2-methylpropanenitrile | ** | *** |
| 6-(3-amino-6-(4-(1-cyclopropylethoxy)phenyl)pyrazin-2-yl)-3,4-dihydroisoquinolin-1(2H)-one | ** | *** |
| 6-(2-amino-5-(4-(2-(dimethylamino)propan-2-yl)phenyl)pyridin-3-yl)-3,4-dihydroisoquinolin-1(2H)-one | ** | *** |
| 2-(4-(5-amino-6-(1-oxo-1,2,3,4-tetrahydroisoquinolin-6-yl)pyrazin-2-yl)phenoxy)-2-methylpropanamide | ** | *** |
| ethyl 2-(4-(5-amino-6-(1-oxo-1,2,3,4-tetrahydroisoquinolin-6-yl)pyrazin-2-yl)phenyl)acetate | * | ** |
| 2-(4-(5-amino-6-(1-oxo-1,2,3,4-tetrahydroisoquinolin-6-yl)pyrazin-2-yl)-1H-pyrazol-1-yl)acetonitrile | * | ** |
| 4-(6-amino-6-(1-oxo-2,3,4,5-tetrahydro-1H-benzo[c]azepin-7-yl)pyrazin-2-yl)-N-cyclopropyl-N-methylbenzenesulfonamide | *** | *** |
| 2-(4-(5-amino-6-(1-oxo-1,2,3,4-tetrahydroisoquinolin-6-yl)pyrazin-2-yl)-2-methylphenyl)-2-methylpropanenitrile | ** | *** |
| 2-(6'-amino-5'-(1-oxo-1,2,3,4-tetrahydroisoquinolin-6-yl)-[3,3'-bipyridin]-6-yl)-2-methylpropanenitrile | ** | ** |
| 2-(4-(5-amino-6-(1-oxo-1,2,3,4-tetrahydroisoquinolin-6-yl)pyrazin-2-yl)phenoxy)acetonitrile | * | ** |
| 4-(5-amino-6-(5-oxo-2,3,4,5-tetrahydrobenzo[f][1,4]oxazepin-8-yl)pyrazin-2-yl)-N-cyclopropyl-N-methylbenzenesulfonamide | *** | *** |

TABLE 1-continued

| Compound | IC$_{50}$ (μM) | |
|---|---|---|
| | 1 μM ATP | 50 μM ATP |
| 4-(6-amino-5-(2-oxo-1,2,3,4,5,6-hexahydrobenzo[b]azocin-8-yl)pyridin-3-yl)-N-cyclopropyl-N-methylbenzenesulfonamide | * | ** |
| 4-(4-(5-amino-6-(1-oxo-1,2,3,4-tetrahydroisoquinolin-6-yl)pyrazin-2-yl)phenyl)tetrahydro-2H-pyran-4-carbonitrile | ** | *** |
| 4-(5-amino-6-(3-methyl-1-oxo-1,2,3,4-tetrahydrophthalazin-6-yl)pyrazin-2-yl)-N-cyclopropyl-N-methylbenzenesulfonamide | ** | *** |
| 6-(3-amino-6-(4-(2-hydroxypropan-2-yl)phenyl)pyrazin-2-yl)-3,4-dihydroisoquinolin-1(2H)-one | ** | *** |
| 4-(5-amino-6-(2-methyl-1-oxo-1,2,3,4-tetrahydroisoquinolin-6-yl)pyrazin-2-yl)-N-cyclopropyl-N-methylbenzenesulfonamide | * | ** |
| 4-(5-amino-6-(5-oxo-2,3,4,5-tetrahydro-1H-benzo[e][1,4]diazepin-8-yl)pyrazin-2-yl)-N-cyclopropyl-N-methylbenzenesulfonamide | *** | *** |
| 4-(6-amino-5-(5-oxo-2,3,4,5-tetrahydro-1H-benzo[e][1,4]diazepin-8-yl)pyridin-3-yl)-N-cyclopropyl-N-methylbenzenesulfonamide | *** | *** |
| 1-(4-(5-amino-6-(1-oxo-1,2-dihydroisoquinolin-6-yl)pyrazin-2-yl)phenyl)cyclopropanecarbonitrile | ** | *** |
| 2-(5-(5-amino-6-(1-oxo-1,2,3,4-tetrahydroisoquinolin-6-yl)pyrazin-2-yl)thiophen-2-yl)acetonitrile | ** | *** |
| 5-(5-amino-6-(1-oxo-1,2,3,4-tetrahydroisoquinolin-6-yl)pyrazin-2-yl)-1-methyl-2,3-dihydro-1H-indene-1-carbonitrile | ** | *** |
| 4-(6-amino-5-(1-oxo-1,2,3,4-tetrahydroisoquinolin-6-yl)pyridazin-3-yl)-N-cyclopropyl-N-methylbenzenesulfonamide | ** | *** |
| 1-(4-(6-amino-5-(1-oxo-1,2,3,4-tetrahydroisoquinolin-6-yl)pyridazin-3-yl)phenyl)cyclopropanecarbonitrile | * | * |
| 4-(5-amino-6-(4,4-dideutero-1-oxo-1,2,3,4-tetrahydroisoquinolin-6-yl)pyrazin-2-yl)-N-cyclopropyl-N-methylbenzenesulfonamide | *** | *** |
| 2-(5-(5-amino-6-(1-oxo-1,2,3,4-tetrahydroisoquinolin-6-yl)pyrazin-2-yl)thiophen-2-yl)-2-methylpropanenitrile | ** | *** |
| (1R,5S,6s)-6-(4-(5-amino-6-(1-oxo-1,2,3,4-tetrahydroisoquinolin-6-yl)pyrazin-2-yl)phenyl)-3-oxabicyclo[3.1.0]hexane-6-carbonitrile | ** | *** |
| N-(4-(6-amino-5-(1-oxo-1,2,3,4-tetrahydroisoquinolin-6-yl)pyridin-3-yl)benzyl)acetamide | ** | *** |
| 6-(3-amino-6-(4-(4-hydroxytetrahydro-2H-pyran-4-yl)phenyl)pyrazin-2-yl)-3,4-dihydroisoquinolin-1(2H)-one | ** | *** |
| 4-(6-amino-5-(2-(2-cyanoethyl)-1-oxo-1,2,3,4-tetrahydroisoquinolin-6-yl)pyridin-3-yl)-N-cyclopropyl-N-methylbenzenesulfonamide | * | ** |
| (R)-4-(6-amino-5-(3-methyl-5-oxo-2,3,4,5-tetrahydrobenzo[f][1,4]oxazepin-8-yl)pyridin-3-yl)-N-cyclopropyl-N-methylbenzenesulfonamide | *** | *** |
| 6-(2-amino-5-(4-(2-morpholinopropan-2-yl)phenyl)pyridin-3-yl)-3,4-dihydroisoquinolin-1(2H)-one | ** | *** |
| 4-(6-amino-5-(5-oxo-2,3,4,5-tetrahydrobenzo[f][1,4]oxazepin-8-yl)pyridin-3-yl)-N-cyclopropyl-N-methylbenzenesulfonamide | *** | *** |
| 5-(6-amino-5-(1-oxo-1,2,3,4-tetrahydroisoquinolin-6-yl)pyridin-3-yl)-1-methyl-2,3-dihydro-1H-indene-1-carbonitrile | * | *** |
| 4-(4-(5-amino-6-(5-oxo-2,3,4,5-tetrahydro-1H-benzo[e][1,4]diazepin-8-yl)pyrazin-2-yl)phenyl)tetrahydro-2H-pyran-4-carbonitrile | ** | *** |
| 4-(5-amino-6-(3-methyl-5-oxo-2,3,4,5-tetrahydro-1H-benzo[e][1,4]diazepin-8-yl)pyrazin-2-yl)-N-cyclopropyl-N-methylbenzenesulfonamide | *** | *** |
| 2-(4-(5-amino-6-(1-oxo-1,2,3,4-tetrahydroisoquinolin-6-yl)pyrazin-2-yl)phenyl)cyclopropanecarbonitrile | ** | *** |
| 6-(3-amino-6-(4-propionylphenyl)pyrazin-2-yl)-3,4-dihydroisoquinolin-1(2H)-one | ** | *** |
| 4-(5-amino-6-(4,4-dimethyl-1-oxo-1,2,3,4-tetrahydroisoquinolin-6-yl)pyrazin-2-yl)-N-cyclopropyl-N-methylbenzenesulfonamide | *** | *** |
| 4-(5-amino-6-(5-oxo-2,3,4,5-tetrahydro-1H-benzo[e][1,4]diazepin-8-yl)pyrazin-2-yl)-N-cyclopropylbenzenesulfonamide | *** | *** |
| 4-(6-amino-5-(5-oxo-2,3,4,5-tetrahydrobenzo[f][1,4]oxazepin-8-yl)pyridin-3-yl)-N-cyclopropylbenzenesulfonamide | *** | *** |
| 4-(5-amino-6-(5-oxo-2,3,4,5-tetrahydrobenzo[f][1,4]oxazepin-8-yl)pyrazin-2-yl)-N-cyclopropylbenzenesulfonamide | *** | *** |
| 4-(6-amino-5-(1-oxo-2,3,4,5-tetrahydro-1H-benzo[c]azepin-7-yl)pyridin-3-yl)-N-cyclopropylbenzenesulfonamide | *** | *** |
| 6-(3-amino-6-(4-(1-(methylamino)cyclopropyl)phenyl)pyrazin-2-yl)-3,4-dihydroisoquinolin-1(2H)-one | *** | *** |
| 4-(6-amino-5-(4,4-dimethyl-1-oxo-1,2,3,4-tetrahydroisoquinolin-6-yl)pyridin-3-yl)-N-cyclopropylbenzenesulfonamide | *** | *** |
| 1-(4-(5-amino-6-(4,4-dimethyl-1-oxo-1,2,3,4-tetrahydroisoquinolin-6-yl)pyrazin-2-yl)phenyl)cyclopropanecarbonitrile | *** | *** |
| 4-(5-amino-6-(4,4-dimethyl-1-oxo-1,2,3,4-tetrahydroisoquinolin-6-yl)pyrazin-2-yl)-N-cyclopropylbenzenesulfonamide | *** | *** |
| 6-(3-amino-6-(4-(pentafluorosulfanyl)phenyl)pyrazin-2-yl)-3,4-dihydroisoquinolin-1(2H)-one | * | ** |

TABLE 1-continued

| Compound | IC$_{50}$ (μM) | |
|---|---|---|
| | 1 μM ATP | 50 μM ATP |
| (S)-4-(6-amino-5-(3-methyl-5-oxo-2,3,4,5-tetrahydrobenzo[f][1,4]oxazepin-8-yl)pyridin-3-yl)-N-cyclopropyl-N-methylbenzenesulfonamide | ** | *** |
| 4-(4-(5-amino-6-(4,4-dimethyl-1-oxo-1,2,3,4-tetrahydroisoquinolin-6-yl)pyrazin-2-yl)phenyl)tetrahydro-2H-pyran-4-carbonitrile | *** | *** |
| 4-(4-(5-amino-6-(1-oxo-2,3,4,5-tetrahydro-1H-benzo[c]azepin-7-yl)pyrazin-2-yl)phenyl)tetrahydro-2H-pyran-4-carbonitrile | ** | *** |
| 4-(6-amino-5-(4,4-dimethyl-1-oxo-1,2,3,4-tetrahydroisoquinolin-6-yl)pyridin-3-yl)phenyl)tetrahydro-2H-pyran-4-carbonitrile | *** | *** |
| (R)-4-(6-amino-5-(3-((benzyloxy)methyl)-5-oxo-2,3,4,5-tetrahydrobenzo[f][1,4]oxazepin-8-yl)pyridin-3-yl)-N-cyclopropyl-N-methylbenzenesulfonamide | * | *** |
| (S)-4-(6-amino-5-(3-(hydroxymethyl)-5-oxo-2,3,4,5-tetrahydrobenzo[f][1,4]oxazepin-8-yl)pyridin-3-yl)-N-cyclopropyl-N-methylbenzenesulfonamide | *** | *** |
| 4-(5-amino-6-(1'-oxo-2',3'-dihydro-1'H-spiro[cyclopropane-1,4'-isoquinolin]-6'-yl)pyrazin-2-yl)-N-cyclopropyl-N-methylbenzenesulfonamide | *** | *** |
| 1-(4-(5-amino-6-(1'-oxo-2',3'-dihydro-1'H-spiro[cyclopropane-1,4'-isoquinolin]-6'-yl)pyrazin-2-yl)phenyl)cyclopropanecarbonitrile | *** | *** |
| 4-(5-amino-6-(5-oxo-2,3,4,5-tetrahydrobenzo[f][1,4]oxazepin-8-yl)pyrazin-2-yl)-N-cyclopropyl-2-methylbenzenesulfonamide | ** | *** |
| 4-(5-amino-6-(4,4-dimethyl-1-oxo-1,2,3,4-tetrahydroisoquinolin-6-yl)pyrazin-2-yl)-N-cyclopropyl-2-methylbenzenesulfonamide | *** | *** |
| 4-(5-amino-6-(1'-oxo-2',3'-dihydro-1'H-spiro[cyclopropane-1,4'-isoquinolin]-6'-yl)pyrazin-2-yl)-N-cyclopropyl-2-methylbenzenesulfonamide | *** | *** |
| 4-(5-amino-6-(1'-oxo-2',3'-dihydro-1'H-spiro[cyclopropane-1,4'-isoquinolin]-6'-yl)pyrazin-2-yl)-N-cyclopropylbenzenesulfonamide | *** | *** |
| 4-(6-amino-5-(1'-oxo-2',3'-dihydro-1'H-spiro[cyclopropane-1,4'-isoquinolin]-6'-yl)pyridin-3-yl)-N-cyclopropylbenzenesulfonamide | *** | *** |
| 4-(6-amino-5-(1'-oxo-2',3'-dihydro-1'H-spiro[cyclopropane-1,4'-isoquinolin]-6'-yl)pyridin-3-yl)-N-cyclopropyl-N-methylbenzenesulfonamide | *** | *** |
| (S)-4-(5-amino-6-(3-methyl-5-oxo-2,3,4,5-tetrahydro-1H-benzo[e][1,4]diazepin-8-yl)pyrazin-2-yl)-N-cyclopropyl-N-methylbenzenesulfonamide | *** | *** |
| (S)-4-(6-amino-5-(3-methyl-5-oxo-2,3,4,5-tetrahydro-1H-benzo[e][1,4]diazepin-8-yl)pyridin-3-yl)-N-cyclopropyl-N-methylbenzenesulfonamide | *** | *** |
| (S)-4-(6-amino-5-(3-methyl-5-oxo-2,3,4,5-tetrahydro-1H-benzo[e][1,4]diazepin-8-yl)pyridin-3-yl)-N-cyclopropylbenzenesulfonamide | *** | *** |
| 4-(4-(6-amino-5-(1'-oxo-2',3'-dihydro-1'H-spiro[cyclopropane-1,4'-isoquinolin]-6'-yl)pyridin-3-yl)phenyl)tetrahydro-2H-pyran-4-carbonitrile | *** | *** |
| 4-(6-amino-5-(3'-oxospiro[cyclopropane-1,1'-isoindolin]-6'-yl)pyridin-3-yl)-N-cyclopropyl-N-methylbenzenesulfonamide | *** | *** |
| 4-(4-(5-amino-6-(3'-oxospiro[cyclopropane-1,1'-isoindolin]-6'-yl)pyrazin-2-yl)phenyl)tetrahydro-2H-pyran-4-carbonitrile | ** | *** |
| 4-(6-amino-5-(3'-oxospiro[cyclopropane-1,1'-isoindolin]-6'-yl)pyridin-3-yl)-N-cyclopropylbenzenesulfonamide | *** | *** |
| 4-(5-amino-6-(3'-oxospiro[cyclopropane-1,1'-isoindolin]-6'-yl)pyrazin-2-yl)-N-cyclopropylbenzenesulfonamide | ** | *** |
| 4-(4-(6-amino-5-(3'-oxospiro[cyclopropane-1,1'-isoindolin]-6'-yl)pyridin-3-yl)phenyl)tetrahydro-2H-pyran-4-carbonitrile | ** | *** |
| 4-(5-amino-6-(4,4-dideutero-1-oxo-1,2,3,4-tetrahydroisoquinolin-6-yl)pyrazin-2-yl)-N-cyclopropylbenzenesulfonamide | *** | *** |
| 5-(3-amino-6-(4-(N-cyclopropyl-N-methylsulfamoyl)phenyl)pyrazin-2-yl)-N-methylindoline-1-carboxamide | ** | *** |
| 1-(4-(5-amino-6-(3'-oxospiro[cyclopropane-1,1'-isoindolin]-6'-yl)pyrazin-2-yl)phenyl)cyclopropanecarbonitrile | ** | *** |
| 6'-(3-amino-6-(4-fluorophenyl)pyrazin-2-yl)-2',3'-dihydro-1'H-spiro[cyclopropane-1,4'-isoquinolin]-1'-one | * | *** |
| 4-(5-amino-6-(1'-oxo-2',3'-dihydro-1'H-spiro[cyclopropane-1,4'-isoquinolin]-6'-yl)pyrazin-2-yl)benzonitrile | ** | *** |
| 4-(5-amino-6-(8-oxo-5,6,7,8-tetrahydro-2,7-naphthyridin-3-yl)pyrazin-2-yl)-N-cyclopropylbenzenesulfonamide | *** | *** |
| 4-(5-amino-6-(3,3-dimethyl-1-oxoisoindolin-5-yl)pyrazin-2-yl)-N-cyclopropylbenzenesulfonamide | ** | *** |
| 4-(6-amino-5-(3,3-dimethyl-1-oxoisoindolin-5-yl)pyridin-3-yl)-N-cyclopropyl-N-methylbenzenesulfonamide | *** | *** |
| 4-(5-amino-6-(4-bromo-1-hydroxyisoquinolin-6-yl)pyrazin-2-yl)-N-cyclopropyl-N-methylbenzenesulfonamide | *** | *** |
| 4-(6-amino-5-(8-oxo-5,6,7,8-tetrahydro-2,7-naphthyridin-3-yl)pyridin-3-yl)benzonitrile | ** | *** |

TABLE 1-continued

| Compound | IC$_{50}$ (µM) | |
|---|---|---|
| | 1 µM ATP | 50 µM ATP |
| 4-(5-amino-6-(8-oxo-5,6,7,8-tetrahydro-2,7-naphthyridin-3-yl)pyrazin-2-yl)benzonitrile | *** | *** |
| 4-(5-amino-6-(4,4-dimethyl-1,3-dioxo-1,2,3,4-tetrahydroisoquinolin-6-yl)pyrazin-2-yl)-N-cyclopropylbenzenesulfonamide | * | * |
| 4-(6-(1-acetyl-3,3-dimethylindolin-5-yl)-5-aminopyrazin-2-yl)-N-cyclopropyl-N-methylbenzenesulfonamide | ** | *** |
| 6-(2-amino-5-(4-fluorophenyl)pyridin-3-yl)-3,4-dihydro-2,7-naphthyridin-1(2H)-one | ** | ** |
| 4-(6-amino-5-(8-oxo-5,6,7,8-tetrahydro-2,7-naphthyridin-3-yl)pyridin-3-yl)-N-cyclopropyl-N-methylbenzenesulfonamide | *** | *** |
| 4-(5-amino-6-(8-oxo-5,6,7,8-tetrahydro-2,7-naphthyridin-3-yl)pyrazin-2-yl)-N-cyclopropyl-N-methylbenzenesulfonamide | *** | *** |
| 6-(3-amino-6-(4-fluorophenyl)pyrazin-2-yl)-3,4-dihydro-2,7-naphthyridin-1(2H)-one | *** | *** |

6.42. In Vitro Measurement of MST1 Inhibition

Assays were performed in low-volume 384-well black proxiplates (Perkin Elmer, PE-Blk-Proxi-6008269). Eight compounds were first diluted into LDV (Echo) plates using a Multiprobe, at a starting concentration of 1 mM compound in 100% DMSO. Using the ECHO, 75 nl compound was pinged into 384-well proxiplates. The starting concentration of compound in each assay plate is 7.5 uM, followed by 3-fold dilutions, to give quadruplicate ten-point concentration curves. A 3× solution of MST1 enzyme in kinase buffer (Invitrogen, PR4940C) was added to wells containing compound or DMSO controls, followed by a 10 minute preincubation step. Reactions were initiated by adding 5 µL of a mixture of ATP and Z'-Lyte S/T Pep 7 (Invitrogen, PV3180) and proceeded at RT for 1 hour. The final concentration of key reagents in the kinase reactions were 1 µM substrate, 1 nM enzyme, and either 50 µM ATP or 1 mM ATP. At the end of the kinase reaction, 10 ul of developing solution (Invitrogen, catalog #PR4876B; development buffer A diluted 150,000+ in development buffer B) was added to each well and incubated at RT for 1 hr. All wells were read on a Tecan at 400 nm excitation and 460 nm/530 nm emission. Plus and minus enzyme controls were used to calculate percent inhibition and IC$_{50}$ curves were generated using Excel.

6.43. Cell-Based Assay

A cell-based assay that monitors autophosphorylation of intracellular MST1 was also used to characterize compounds of the invention. In this assay, HEK293F cells were transfected with a plasmid coding for full-length human MST1. The cells were grown in cell media (DMEM, 10% FBS, 1×GPS) to 80-90% confluency in 24-well issue culture plates. On day one, ~2×10^7 cells were trypsinized and resuspended in 20 mL cell media minus the GPS. One mL of this cell suspension was transferred to a Vi-cell sample cup and cells were counted on a Beckman Coulter Vi-Cell XR. Cells were then diluted to 3×10^5/per mL in DMEM+10% FBS, enough for 12 mls for one 24-well plate. Each well of a 24-well plate received 500 µl of this cell suspension for a final concentration of 1.5×10^5 cells per well. Cells were then incubated overnight at 37° C. and 5% CO$_2$.

On day two, each well was transfected with 0.5 µg DNA and 1.5 µl Lipofectamine 2000 (Invitrogen; cat. #11668-019). The DNA mix is comprised of 5 ng MST1 T183E, 50 ng MEKK1, 445 ng pcDNA3.1, and 50 ul OPTI-MEM. The Lipofectamine 2000 is comprised of 1.5 µl lipofectamine 2000 and 50 ul OPTI-MEM. The DNA mixture was first pipetted into 15 ml tubes and incubated at RT for 5 minutes, followed by addition of the lipofectamine mix and incubation at RT for 20 minutes. 100 µl of DNA transfection mixture was added to cells in each well of a 24-well plate, followed by incubation overnight at 37° C. and 5% CO$_2$.

On day 3, compounds were serially diluted with 100% DMSO and one µL was transferred to wells of a 1 mL deep 96-well plate. Plates were then transferred to a TC hood and 1 ml of DMEM+0.5% FBS was added to each well containing 1 µl compound. (0.1% DMSO final concentration). Next, media/transfection mix was aspirated from each well of the 24-well plate containing the cells, followed by addition of 300 µl from each compound dilution (remaining compound dilutions kept at 4° C. for later use). Plates were then incubated at 37° C. and 5% CO$_2$ for 4 hours. One µl of 225 µM okadaic acid in 100% DMSO was then pipetted into a new 1 ml deep 96-well plate, followed by addition of 300 µl compound dilution (stored at 4° C. in the previous step) to give a final concentration of 0.75 µM okadaic acid. The media/compound mixture was then aspirated from 24-well plate containing cells and then replaced with the media/compound/okadaic acid mixture. Cells were incubated at 37° C. and 5% CO$_2$ for 2 more hours. Cells were detached by simple pipetting and cell suspensions from each well were transferred into new 1.5 ml tubes. Tubes containing media were centrifuged at 1000×g for 5 minutes to pellet the cells and supernatants were carefully removed and discarded. Cell pellets were usually frozen at −80° C. until the next step.

On day 4, cells were lysed and prepared for Western Blot analysis as follows. Cell pellets were thawed on ice. Lysis buffer consisted of the following components: Tris, pH 7.5, 150 mM NaCl, 1 mM Na$_2$EDTA, 1 mM EGTA, 1% Triton, 2.5 mM sodium pyrophosphate, 1 mM β-glycerophosphate, 1 mM Na$_3$VO$_4$, 1 ug/ml leupeptin, 10 mM EDTA, 2× Halt protease & phosphatase inhibitor cocktail (Thermo Scientific; cat. #1861284). 100 µL of freshly made lysis buffer was added per sample, followed by incubation on ice for 15 min, vortexing for 10-15 seconds, and centrifuging at 12,000×g for 30 sec. Supernatant were carefully removed and mixed with 4×LDS Sample Buffer from Invitrogen (cat. #NP0008; with 50 mM DTT added fresh). Samples were denatured at 70° C. for 10 minutes on a PCR machine, and 10 µl were loaded per lane on 2× Criterion 26-well gels (Biorad; cat. #345-0034).

After SDS-PAGE, samples were transferred from gel to PVDF membrane, blocked for one hour in TBST+5% milk, and washed 3× for 5-10 min with TBST. One membrane was probed with rabbit anti-MST1 (1:3000; Millipore, cat. #07-061) diluted in TBST+5% milk, and another membrane was probed with rabbit anti-phospho-MST1 (T183; Cell Signaling, cat. #3681) (1:2000) diluted in TBST+5% BSA, followed by incubate overnight at 4° C.

On day 5, Western Blots were washed 3× for 5-10 minutes with TBST, probe with anti-rabbit-HRP (1:3000; Biorad, cat. #170-6515) diluted in TBST+5% milk for 1 hour at RT, and washed 3× for 10 minutes with TBST. Blots were developed with ECL reagent (GE Healthcare; cat. #RPN2132) on a Biorad Versadoc Imagin System (Model 5000) and volume analysis performed on each band to obtain density values.

Figures 2A, 2B:
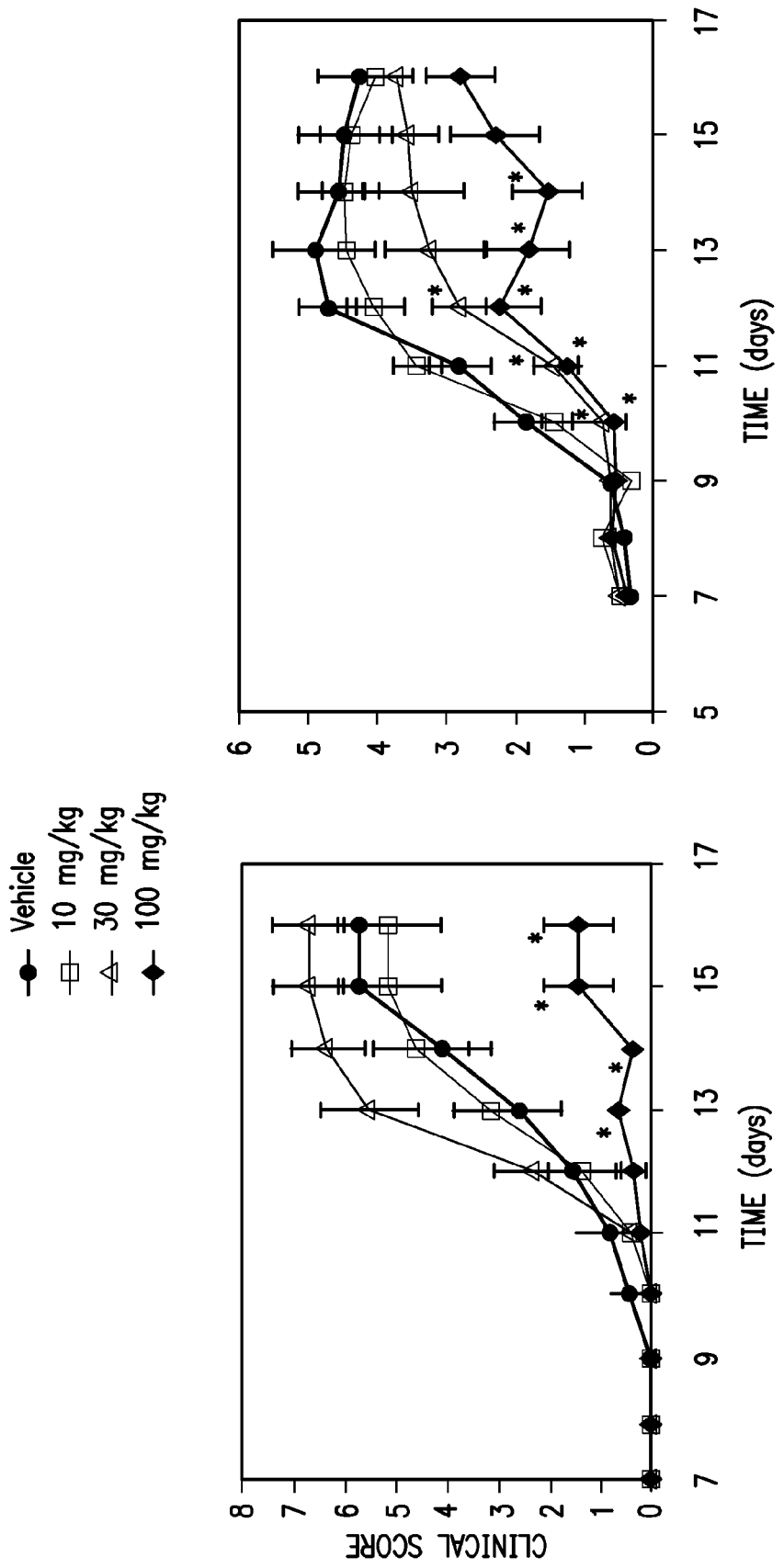
FIG. 2 shows the effect of different doses of a compound of the invention when administered prophylactically (FIG. 2A) and therapeutically (FIG. 2B) to mice in an experimental autoimmune encephalomyelitis (EAE) disease model.

6.44. Pharmacology of 4-(6-amino-5-(1-oxo-1,2,3,4-tetrahydroisoquinolin-6-yl)pyridin-3-yl)-N-cyclopropyl-N-methylbenzenesulfonamide The compound 4-(6-amino-5-(1-oxo-1,2,3,4-tetrahydroisoquinolin-6-yl)pyridin-3-yl)-N-cyclopropyl-N-methylbenzenesulfonamide was tested in the EAE disease model described above. In a first study, the prophylactic effect of the compound was measured: mice were generally dosed PO, bid, for 22 days, starting on Day (−1) before MOG peptide immunization (in the 100 mpk group, compound was dosed BID on days-1-9, and QD on days 10-21.) Four groups of mice (n=10 per group) were tested: vehicle control; 10 mg/kg, 30 mg/kg, and 100 mg/kg compound. Results are shown in FIG. 2A, wherein * indicates $p<0.05$ versus control.

A second study examined the therapeutic effect of the compound. Here, mice were generally dosed PO, BID, for 14 days, starting on Day 9 after MOG peptide immunization (in the 100 mpk group, compound was dosed BID on days 9-13, and QD on days 14-23). Results are shown in FIG. 2B, wherein * indicates $p<0.05$ versus control.

Figure 3:
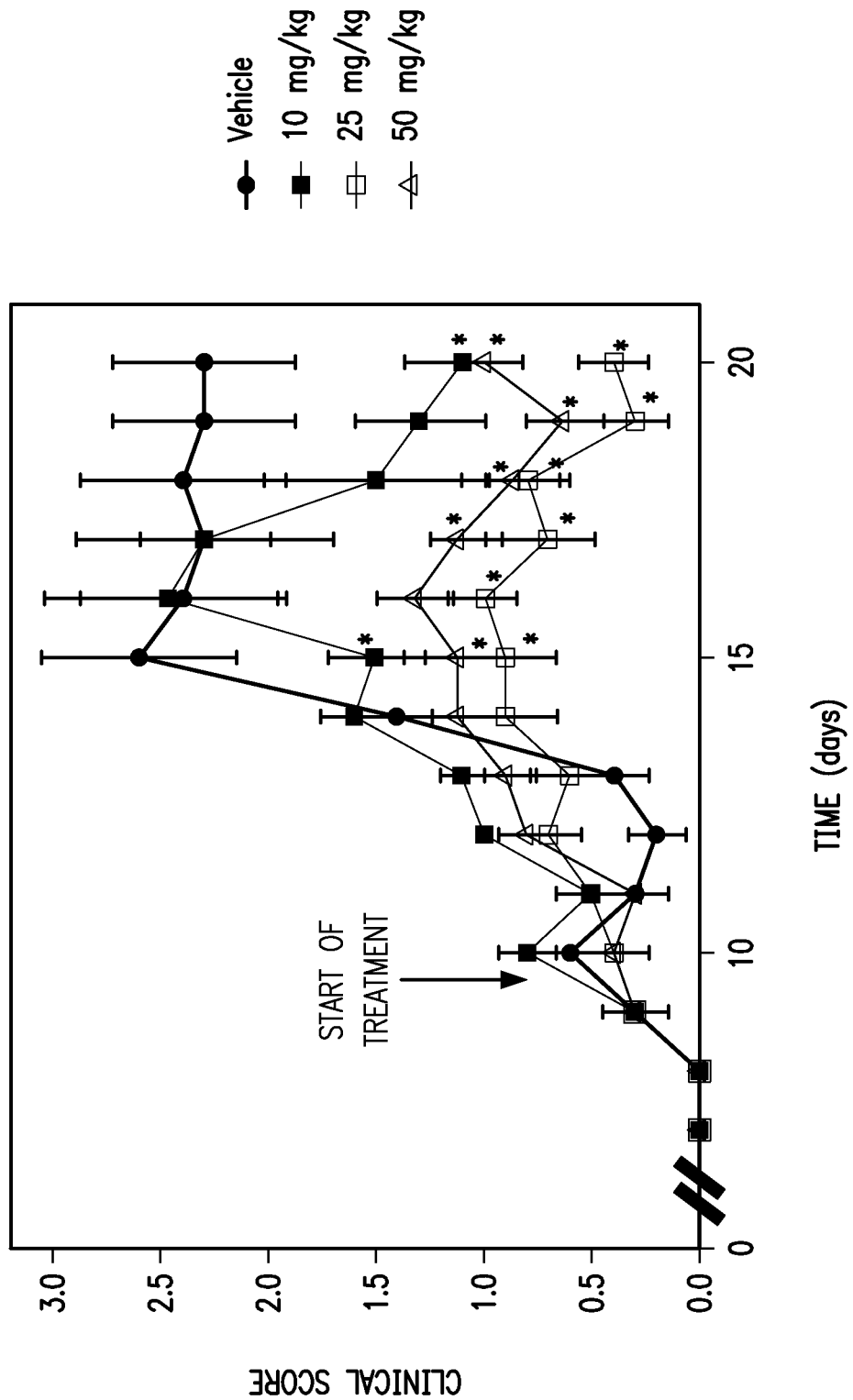
FIG. 3 shows the effect of different doses of a compound of the invention when administered therapeutically to rats in an EAE disease model.

The compound was also studied in a rat EAE model. Here, four groups of rats (n=10 per group) were administered vehicle control, 10 mg/kg, 25 mg/kg, or 50 mg/kg doses, PO, BID. Dosing began on Day 9 after immunization. As shown in FIG. 3, the compound again exhibited a dose-dependent reduction in severity of clinical score (* indicates $p<0.05$ versus control).

FIG. 4 shows results obtained from a study of the compound in a CIA disease model. In this test, mice were dosed PO, bid, for 21 days, starting on Day 20 after immunization. Four groups of mice were used (n=10 per group): vehicle control, 10 mg/kg, 30 mg/kg, and 100 mg/kg. A clear benefit versus control was observed (* indicates $p<0.05$ versus control).

The compound was further studied in a rat CIA disease model, using four groups of rats (n=10 per group): vehicle control, 10 mg/kg, 25 mg/kg, and 50 mg/kg. The rats were dosed PO, BID (10 and 25 mg/kg groups) or QD (50 mg/kg group) beginning on Day 11 after immunization. As shown in FIG. 5, the compound again showed a therapeutic effect. FIG. 5A shows the cumulative arthritis score as a function of time and dose; FIG. 5B shows the change in ankle thickness as a function of time and dose (* indicates $p<0.05$ versus control). Here, ankle thickness was measured by volume (water displacement).

FIG. 6 shows the effect of the compound on liver enzyme and cytokine response in a Con-A induced hepatitis model. Four groups of mice were used (n=10 per group): vehicle control, 10 mg/kg, 30 mg/kg, and 100 mg/kg. The mice were dosed 16 h and 1 h before, and 8 h after, the Con-A challenge. A clear effect in TNF-α, IL-6, MCP-1, IFN-γ, ALT and AST was observed (* indicates $p<0.05$ versus control; ** indicates $p<0.1$ versus control).

6.45. Pharmacology of 1-(4-(5-amino-6-(1-oxo-1,2,3,4-tetrahydroisoquinolin-6-yl)pyrazin-2-yl)phenyl)cyclopropanecarbonitrile The compound I-(4-(5-amino-6-(1-oxo-1,2,3,4-tetrahydroisoquinolin-6-yl)pyrazin-2-yl)phenyl)cyclopropanecarbonitrile was studied in a rat EAE model. Here, five groups of rats (n=10 per group) were administered vehicle control, 0.3 mg/kg, 1 mg/kg, 3 mg/kg, or 10 mg/kg doses, PO, QD, starting on Day 10 after immunization. As shown in FIG. 7A, the compound exhibited a dose-dependent reduction in severity of clinical score (* indicates $p<0.05$ versus control). The effect is also seen in FIG. 7B, which shows the disease development as a function of test group.

FIG. 8 shows the effect of the compound on liver enzyme and cytokine response in a Con-A induced hepatitis model. Five groups of mice were used (n=10 per group): vehicle control, 1 mg/kg, 3 mg/kg, 10 mg/kg, and 30 mg/kg. The mice were dosed PO 16 h and 1 h before, and 8 h after, the Con-A challenge. A clear effect in TNF-α, IL-6, MCP-1, IFN-γ, ALT and AST was observed (* indicates $p<0.05$ versus control).

6.46. Pharmacology of 4-(5-amino-6-(1-oxo-1,2,3,4-tetrahydroisoquinolin-6-yl)pyrazin-2-yl)-N-cyclopropyl-N-methylbenzenesulfonamide The compound 4-(5-amino-6-(1-oxo-1,2,3,4-tetrahydroisoquinolin-6-yl)pyrazin-2-yl)-N-cyclopropyl-N-methylbenzenesulfonamide was studied in a mouse EAE model. Here, four groups of mice (n=10 per group) were administered vehicle control, 3 mg/kg, 10 mg/kg, or mg/kg doses BID for 12 days, starting on Day 9 after MOG peptide immunization. FIG. 9A shows the effect of subcutaneous dosing: a clear dose-dependency in clinical score was observed (* indicates $p<0.05$ versus control). FIG. 9B shows the effect of oral (PO) dosing.

The effect of the compound in a mouse CIA model was also observed as a function of dose and method of delivery. FIGS. 10A and 10B show the effect of the compound on cumulative scores and change in ankle thickness when administered subcutaneously (* indicates $p<0.05$ versus control) to three groups of mice (n=10 per group). The groups were administered vehicle control, 10 mg/kg, or 30 mg/kg doses BID for three weeks, starting on Day 20 after collagen immunization. FIGS. 10C and 10D show results obtained when the compound was administered orally (* indicates $p<0.05$ versus control) to four groups of mice (n=10 per group). The groups were administered vehicle control, 10 mg/kg, 30 mg/kg, or 50 mg/kg doses BID for three weeks, starting on Day 20 after collagen immunization.

All references (e.g., patents and published patent applications) cited above are incorporated herein by reference.

What is claimed is:

1. A compound of the formula:

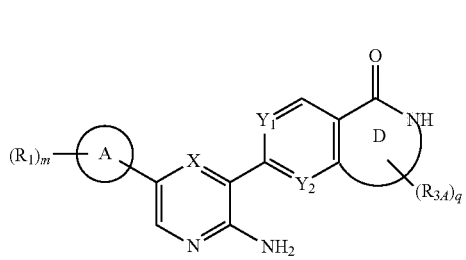

or a pharmaceutically acceptable salt thereof, wherein:
A is aryl or 4-7-membered heterocycle;
D is a 4-7-membered heterocycle;
X is N or CH;
$Y_1$ and $Y_2$ are each independently S, N or CH, provided that at least one of $Y_1$ and $Y_2$ is N or CH;
each $R_1$ is independently $R_{1A}$, $-(R_{1B})_n SO_p R_{1C}$, $-(R_{1B})_n SO_p N(R_{1C})_2$, $-(R_{1B})_n NR_{1C} SO_p R_{1C}$, $-(R_{1B})_n C(O)N(R_{1C})_2$, or $-(R_{1B})_n NR_{1C} C(O)R_{1C}$, or optionally substituted $C_{1-12}$ hydrocarbyl or 2-12-membered heterocarbyl, which optional substitution is with one or more of $R_{1A}$;
each $R_{1A}$ is independently amino, alkoxyl, carboxyl, cyano, halo, or hydroxyl;
each $R_{1B}$ is independently $C_{1-12}$ hydrocarbyl optionally substituted with one or more of amino, alkoxyl, carboxyl, cyano, halo, or hydroxyl;
each $R_{1C}$ is independently hydrogen or optionally substituted $C_{1-12}$ hydrocarbyl or 2-12-membered heterocarbyl, which optional substitution is with one or more of amino, alkoxyl, carboxyl, cyano, halo, or hydroxyl;
each $R_{3A}$ is independently amino, alkoxyl, carboxyl, cyano, halo, or hydroxyl;
m is 0-3;
n is 0 or 1;
p is 0-2; and
q is 0-2.

2. The compound of claim 1, which is of the formula:

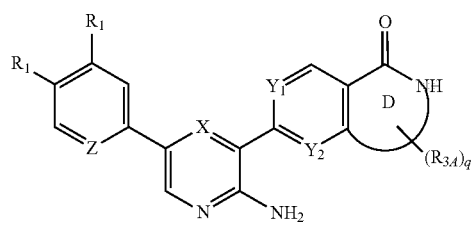

wherein Z is N or $CR_1$.

3. The compound of claim 2, which is of the formula:

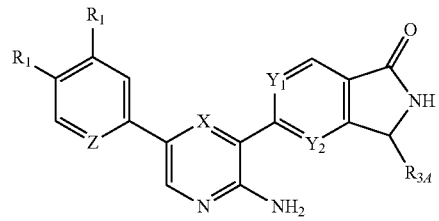

wherein $Y_1$ and $Y_2$ are each independently N or OH.

4. The compound of claim 2, which is of the formula:

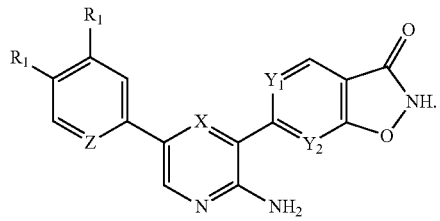

5. The compound of claim 2, which is of the formula:

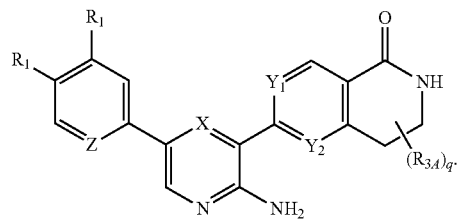

6. The compound of claim 2, which is of the formula:

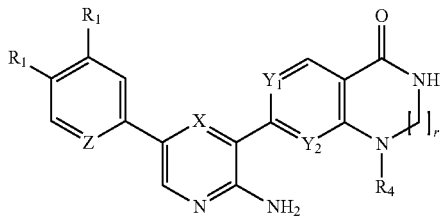

wherein:
R is hydrogen or alkyl; and
r is 1 or 2.

7. The compound of claim 2, which is of the formula:

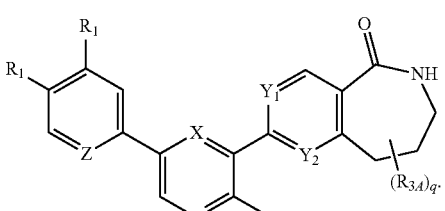

8. The compound of claim 1, wherein X is N.
9. The compound of claim 1, wherein $Y_1$ is CH.
10. The compound of claim 1, wherein $Y_2$ is CH.
11. The compound of claim 2, wherein Z is N.
12. The compound of claim 2, wherein Z is $CR_1$.
13. The compound of claim 1, wherein $R_1$ is —$(R_{1B})_n$SO$_p$R$_{1C}$, —$(R_{1B})_n$SO$_p$N(R$_{1C}$)$_2$, —$(R_{1B})_n$NR$_{1C}$SO$_p$R$_{1C}$, —$(R_{1B})_n$C(O)N(R$_{1C}$)$_2$, or —$(R_{1B})_n$NR$_{1C}$C(O)R$_{1C}$.
14. The compound of claim 13, wherein n=0.
15. The compound of claim 13, wherein p=2.
16. The compound of claim 13, which is of the formula:

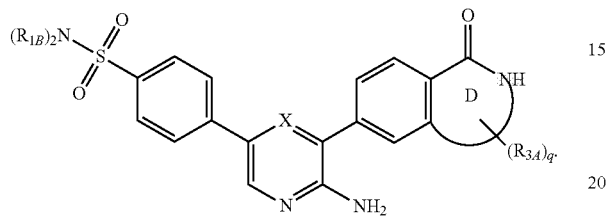

17. A pharmaceutical composition comprising a compound of claim 1 and a pharmaceutically acceptable excipients or diluent.

* * * * *